United States Patent
Uckun et al.

(10) Patent No.: US 11,066,421 B1
(45) Date of Patent: Jul. 20, 2021

(54) SYNTHETIC CINCHONA ALKALOIDS AGAINST CANCER

(71) Applicant: Ares Pharmaceuticals, LLC, White Bear Lake, MN (US)

(72) Inventors: Fatih M. Uckun, White Bear Lake, MN (US); Taracad Venkatachalam, Mississagua (CA)

(73) Assignee: Ares Pharmaceuticals, LLC, White Bear Lake, MN (US)

( * ) Notice: Subject to any disclaimer, the term of this patent is extended or adjusted under 35 U.S.C. 154(b) by 0 days.

(21) Appl. No.: 17/171,601

(22) Filed: Feb. 9, 2021

(51) Int. Cl.
*C07D 519/00* (2006.01)
*A61P 35/04* (2006.01)

(52) U.S. Cl.
CPC ............ *C07D 519/00* (2013.01); *A61P 35/04* (2018.01)

(58) Field of Classification Search
CPC ............................... C07D 519/00; A61P 35/04
USPC ........................................................ 514/274
See application file for complete search history.

(56) References Cited

U.S. PATENT DOCUMENTS

| | | | |
|---|---|---|---|
| 5,635,515 | A | 6/1997 | Chauffert et al. |
| 6,528,524 | B2 | 3/2003 | Genne et al. |
| 9,301,956 | B2 | 4/2016 | Celewicz et al. |
| 2005/0112199 | A1 | 5/2005 | Padval et al. |

FOREIGN PATENT DOCUMENTS

| | | |
|---|---|---|
| CA | 2891633 A1 | 3/2015 |
| EP | 1477488 A1 | 11/2004 |
| PL | 215451 B1 | 5/2012 |

OTHER PUBLICATIONS

Bodkin, J. A. and McLeod, M. D. "The Sharpless asymmetric aminohydroxylation" (2002) J. Chem. Soc., Perkin Trans. 1, 2733-2746.
Boratyński, P. J. "Dimeric Cinchona alkaloids" (2015) Mol Divers 19: 385-422.
Brown, R. T. and Curless, D. "Stereospecific Synthesis of Erythro Cinchona Alkaloids from Secologanin" (1986) Tetrahedron Letters 27(49): 6005-6008.
Chavez, K. J. et al. "Triple Negative Breast Cancer Cell Lines: One Tool in the Search for Better Treatment of Triple Negative Breast Cancer" (2010) Breast Dis. 32(1-2): 35-48.
Chemler, S. R. "Phenanthroindolizidines and Phenanthroquinolizidines: Promising Alkaloids for Anti-Cancer Therapy" (2009) Curr Bioact Compd. 5(1): 2-19.
Cuendet, M. and Pezzuto, J. M. "Antitumor Alkaloids in Clinical Use or in Clinical Trials" (2007) Modern Alkaloids: Structure, Isolation, Synthesis and Biology, 25-52.

Global Burden of Disease Cancer Collaboration "Global, Regional, and National Cancer Incidence, Mortality, Years of Life Lost, Years Lived With Disability, and Disability-Adjusted Life-Years for 29 Cancer Groups, 1990 to 2017" (2019) JAMA Oncol. 5(12): 1749-1768.
Rosenkranz, V. and Wink, M. "Alkaloids Induce Programmed Cell Death in Bloodstream Forms of Trypanosomes (Trypanosoma b. brucei)" (2008) Molecules 13: 2462-2473.
Kolb, H. C. et al. "Catalytic Asymmetric Dihydroxylation" (1994) Chem. Rev. 94: 2483-2547.
Lee, A. and Lee, F. C. "Medical oncology management of advanced hepatocellular carcinoma 2019: a reality check" (2020) Front. Med. 14(3): 273-283.
Lee, S. Y. et al. "Hydrocinchonine, Cinchonine, and Quinidine Potentiate Paclitaxel-Induced Cytotoxicity and Apoptosis via Multidrug Resistance Reversal in MES-SA/DX5 Uterine Sarcoma Cells" (2011) Environ Toxicol. 26(4): 424-431.
Martirosyan, A. R. et al. "Differentiation-inducing quinolines as experimental breast cancer agents in the MCF-7 human breast cancer cell model" (2004) Biochemical Pharmacology 68(9):1729-1738.
Myers, D. E. et al. "CD19-antigen specific nanoscale liposomal formulation of a SYK P-site inhibitor causes apoptotic destruction of human B-precursor leukemia cells" (2014) Integr Biol (Camb). 6(8): 766-780.
Rafei, H. et al. "Targeted therapy paves the way for the cure of acute lymphoblastic leukaemia" (2020) British Journal of Haematology 188: 207-223.
Vaddepally, R. K. et al. "Review of Indications of FDA-Approved Immune Checkpoint Inhibitors per NCCN Guidelines with the Level of Evidence" (2020) Cancers 12: 738(1-19).

(Continued)

*Primary Examiner* — Kahsay Habte
(74) *Attorney, Agent, or Firm* — Volpe Koenig

(57) ABSTRACT

Novel cinchona alkaloid compounds have been synthesized and discovered to have potent cytotoxic activity against cancer cells both in vitro and in vivo.

Cinchona alkaloids, including trimeric cinchona alkaloids as well as their polymers can be used as catalysts of complex chemical reactions in organic chemistry, for example for the enantioselective desymmetrization of cyclic anhydrides, asymmetric synthesis of amino acids (Ayyanar Siva, Eagambaram Murugan. Synthesis 2005; 17:2927-2933; Hyeunggeun Park et al. Tetrahedron Letters, Volume 42, Issue 28, 2001, Pages 4645-4648; Shohei Takata et al., RSC Adv., 2016, 6, 72300-72305; Masud Parvez et al., Macromolecules 2014, 47, 6, 1922-1928; Marcelli, T. 2007, UvA-DARE (Digital Academic Repository). https://pure.uva.nl/ws/files/4416997/52576_marcelli_thesis.pdf Compounds described herein exhibit broad-spectrum therapeutic efficacy against different cancer types, including leukemias/lymphomas, prostate cancer, breast cancer, malignant melanoma, aggressive brain tumor/glioblastoma multiforme (GBM), non-small cell lung cancer. The chemical structure of the compounds includes a trimeric cinchona alkaloid and derivatives containing various groups attached in their structure.

18 Claims, 19 Drawing Sheets

(56) References Cited

OTHER PUBLICATIONS

Rosenkranz, V. and Wink, M. "Induction of Apoptosis by Alkaloids, Non-Protein Amino Acids, and Cardiac Glycosides in Human Promyelotic HL-60 Cells" (2007) Z Naturforsch C J Biosci. 62: 458-466.

Sahin, T. K. et al. "Anti-prostate cancer activity of a nanoformulation of the spleen tyrosine kinase (SYK) inhibitor C61" (2020) Anti-Cancer Drugs 31(6): 609-616.

Solary, E. et al. "Phase I study of cinchonine, a multidrug resistance reversing agent, combined with the CHVP regimen in relapsed and refractory lymphoproliferative syndromes" (2000) Leukemia 14: 2085-2094.

Tao, H. et al. "Alkaloids as Anticancer Agents: A Review of Chinese Patents in Recent 5 Years" (2020) Recent Patents on Anti-Cancer Drug Discovery 15: 2-13.

Uckun, F. M. et al. "STAT3 is a substrate of SYK tyrosine kinase in B-lineage leukemia/lymphoma cells exposed to oxidative stress" (2010) PNAS 107(7): 2902-2907.

Uckun, F. M. et al. "Targeting SYK kinase-dependent anti-apoptotic resistance pathway in B-lineage acute lymphoblastic leukaemia (ALL) cells with a potent SYK inhibitory pentapeptide mimic" (2010) British Journal of Haematology 149: 508-517.

Uckun, F. M. et al. "Nanoscale liposomal formulation of a SYK P-site inhibitor against B-precursor leukemia" (2013) BLOOD 121(21): 4348-4354.

Uckun, F. M. et al. "Liposomal Nanoparticles of a Spleen Tyrosine Kinase P-Site Inhibitor Amplify the Potency of Low Dose Total Body Irradiation Against Aggressive B-Precursor Leukemia and Yield Superior Survival Outcomes in Mice" (2015) EBioMedicine 2(6): 554-562.

Uckun, F. M. et al. "Inducing apoptosis in chemotherapy-resistant B-lineage acute lymphoblastic leukaemia cells by targeting HSPA5, a master regulator of the anti-apoptotic unfolded protein response signalling network" (2011) British Journal of Haematology 153(6):741-752.

Uckun, F. M. et al. "Recombinant human CD19L-sTRAIL effectively targets B cell precursor acute lymphoblastic leukemia" (2015) J Clin Invest. 125(3): 1006-1018.

Uckun, F. M. et al. "Contemporary patient-tailored treatment strategies against high risk and relapsed or refractory multiple myeloma" (2019) EBioMedicine. 39: 612-620.

Uckun, F. M. et al. "Recurrent or Refractory High-Grade Gliomas Treated by Convection-Enhanced Delivery of a TGFβ2-Targeting RNA Therapeutic: A Post-Hoc Analysis with Long-Term Follow-Up" (2019) Cancers (Basel) 11(12): 1892 (1-21).

Narla, R. K. et al. "4-(3'-Bromo-4' hydroxylphenyl)-amino-6,7-dimethoxyquinazoline: A Novel Quinazoline Derivative with Potent Cytotoxic Activity against Human Glioblastoma Cells" (1998) Clinical Cancer Research 4: 1405-1414.

Uckun, F. M. et al. "CD22 EXON 12 deletion as a pathogenic mechanism of human B-precursor leukemia" (2010) PNAS 107(39): 16852-16857.

Uckun, F. M. et al. "Serine phosphorylation by SYK is critical for nuclear localization and transcription factor function of Ikaros" (2012) PNAS 109(44): 18072-18077.

Uckun, F. M. et al. "Vinorelbine-based salvage chemotherapy for therapy-refractory aggressive leukaemias" (2006) Br J Haematol 135(4): 500-508.

Narla, R. K. et al. "In Vivo Antitumor Activity of Bis(4,7-dimethyl-1,10-phenanthroline) Sulfatooxovanadium(IV) {METVAN [VO(SO4)(Me2-Phen)2]}" (2001) Clinical Cancer Research 7: 2124-2133.

Li, H. Y. et al. "The Tumor Microenvironment Regulates Sensitivity of Murine Lung Tumors to PD-1/PD-L1 Antibody Blockade" (2017) Cancer Immunol Res. 5(9): 767-777.

Deskin, B. et al. "Inhibition of HDAC6 Attenuates Tumor Growth of Non-Small Cell Lung Cancer" (2020) Translational Oncology 13(2): 135-145.

Dibirdik, I. et al. "In vivo Anti-Cancer Activity of a Liposomal Nanoparticle Construct of Multifunctional Tyrosine Kinase Inhibitor 4-(4'-Hydroxyphenyl)-Amino-6,7-Dimethoxyquinazoline" (2010) J Nanomedic Nanotechnolo 1: 101 (2-4).

Uckun, F. M. et al. "Anti-breast cancer activity of LFM-A13, a potent inhibitor of Polo-like kinase (PLK)" (2007) Bioorganic & Medicinal Chemistry 15: 800-814.

Kellar, A. et al. "Preclinical Murine Models for Lung Cancer: Clinical Trial Applications" (2015) Biomed Res Int. 2015: 621324 (1-17).

Richmond, A. and Su, Y. "Mouse xenograft models vs GEM models for human cancer therapeutics" (2008) Disease Models & Mechanisms 1: 78-82.

Xu, C. et al. "Patient-derived xenograft mouse models: A high fidelity tool for individualized medicine (Review)" (2019) Oncology Letters 17: 3-10.

Siva, A. and Murugan, E. et al. "A New Trimeric Cinchona Alkaloid as a Chiral Phase-Transfer Catalyst for the Synthesis of Asymmetric a-Amino Acids" (2005) Synthesis 17: 2927-2933.

Park, H. G. et al. "Trimeric Cinchona alkaloid phase-transfer catalyst: α,α',α"-tris[O(9)-allylcinchonidinium]mesitylene tribromide" (2001) Tetrahedron Letters 42: 4645-4648.

Takata, S. et al. "Synthesis of cinchona alkaloid sulfonamide polymers as sustainable catalysts for the enantioselective desymmetrization of cyclic anhydrides" (2016) RSC Adv. 6: 72300-72305.

Parvez, M. et al. "Synthesis of Cinchona Alkaloid-Derived Chiral Polymers by Mizoroki-Heck Polymerization and Their Application to Asymmetric Catalysis" (2014) Macromolecules 47: 1922-1928.

Marcelli, T. "Cinchona-derived organocatalysts for asymmetric carbon-carbon bond formation" (2007) Thesis, University of Amsterdam.

Descriptive Data Summary

|  | AP-5 | DEX | ADR | ETO | MTX | ARA-C | GEM | 2-CDO | FLU | VCR |
|---|---|---|---|---|---|---|---|---|---|---|
| Number of values | 26 | 25 | 25 | 26 | 26 | 23 | 25 | 26 | 26 | 26 |
| Minimum (% apoptosis) | 79.9 | 0.0 | 0.0 | 0.0 | 0.0 | 0.0 | 0.0 | 0.0 | 0.0 | 14.0 |
| Maximum (% apoptosis) | 99.6 | 82.0 | 95.9 | 95.6 | 58.9 | 65.2 | 72.2 | 83.9 | 93.7 | 93.3 |
| Mean (% apoptosis) | 93.5 | 21.5 | 55.2 | 50.3 | 5.9 | 26.8 | 20.7 | 35.8 | 51.7 | 61.1 |
| SE (% apoptosis) | 1.1 | 5.0 | 6.9 | 6.2 | 2.5 | 4.0 | 4.1 | 5.4 | 5.5 | 5.6 |

Descriptive Data Summary

|  | AP-5 | Other Drugs |
|---|---|---|
| Number of values | 26 | 228 |
| Minimum (% apoptosis) | 79.0 | 0.0 |
| Median (% apoptosis) | 96.1 | 32.0 |
| Maximum (% apoptosis) | 99.6 | 96.0 |
| Mean (% apoptosis) | 93.5 | 36.7 |
| SE (% apoptosis) | 1.1 | 2.1 |

C. Descriptive Data Summary

|  | CON | 1μM AP-5 | 3μM AP-5 |  | CON | 1μM AP-5 | 3μM AP-5 |
|---|---|---|---|---|---|---|---|
| Number of mice | 9 | 8 | 8 | Number of mice | 9 | 8 | 8 |
| Minimum | 1.7 | 1.2 | 1.3 | Minimum | 12.5 | 3.7 | 3.0 |
| 25% Percentile | 2.9 | 1.4 | 1.4 | 25% Percentile | 357.0 | 4.8 | 3.2 |
| Median | 3.5 | 1.4 | 1.5 | Median | 564.0 | 8.2 | 5.9 |
| 75% Percentile | 3.6 | 1.6 | 1.5 | 75% Percentile | 740.5 | 10.5 | 6.5 |
| Maximum | 4.0 | 1.8 | 1.5 | Maximum | 940.0 | 12.7 | 12.4 |
|  |  |  |  |  |  |  |  |
| Mean | 3.2 | 1.5 | 1.5 | Mean | 536.4 | 7.9 | 5.8 |
| SE | 0.2 | 0.1 | 0.0 | SE | 94.4 | 1.1 | 1.1 |

| (C) Descriptive Data Summary | | | | | |
|---|---|---|---|---|---|
| Day 14 | Vehicle | AP-1 | Day 16 | Vehicle | AP-1 |
| Number of mice | 9 | 9 | Number of values | 9 | 8 |
| Tumor volume (mm$^3$), Minimum | 106.0 | 124.0 | Minimum | 394.0 | 278.0 |
| Tumor volume (mm$^3$), Maximum | 689.0 | 453.0 | Maximum | 2261 | 935.0 |
| Tumor volume (mm$^3$), Mean | 329.0 | 222.6 | Mean | 1008 | 484.3 |
| Tumor volume (mm$^3$), SE | 61.40 | 37.39 | SE | 195.2 | 76.54 |

(C) Descriptive Data Summary

|  | Day 10 | | Day 14 | |
| --- | --- | --- | --- | --- |
|  | Vehicle | AP-1 | Vehicle | AP-1 |
| Number of Mice | 10 | 20 | 10 | 18 |
| Tumor volume, Minimum, mm³ | 72 | 0 | 144 | 0 |
| Tumor volume, Maximum, mm³ | 220 | 128 | 616 | 192 |
| Tumor volume, Mean (mm³) | 137 | 49 | 290 | 77 |
| Tumor volume SE of Mean (mm³) | 14 | 11 | 48 | 13 |

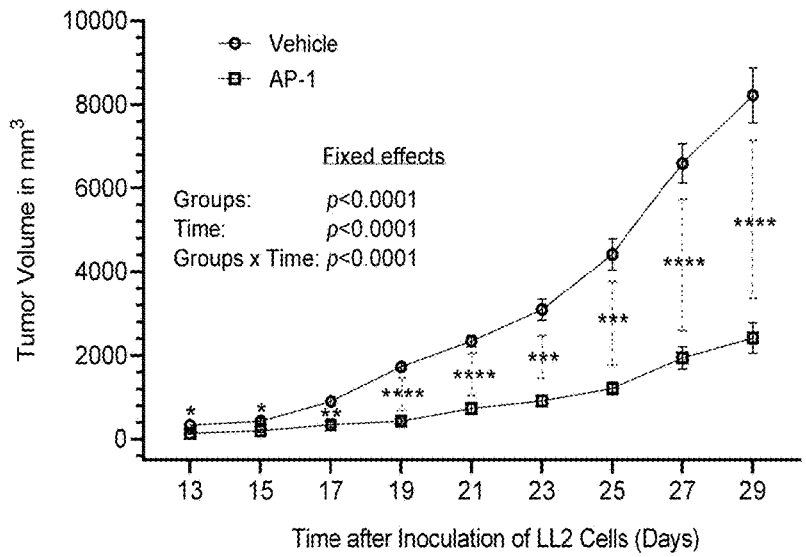

Descriptive Data Summary: LL2 Tumor Growth Rates in C57BL/6 Mice Treated with AP-1 versus Vehicle

| Vehicle | Day 13 | Day 15 | Day 17 | Day 19 | Day 21 | Day 23 | Day 25 | Day 27 | Day 29 |
|---|---|---|---|---|---|---|---|---|---|
| Number of mice | 10 | 10 | 9 | 8 | 8 | 8 | 8 | 8 | 8 |
| Tumor volume, Minimum, $mm^3$ | 72 | 105 | 160 | 1485 | 1560 | 1872 | 2850 | 4224 | 6156 |
| Tumor volume, Maximum, $mm^3$ | 490 | 672 | 1144 | 2240 | 2772 | 3840 | 6000 | 8640 | 10948 |
| Tumor volume Mean ($mm^3$) | 329 | 432 | 900 | 1727 | 2340 | 3091 | 4410 | 6591 | 8221 |
| Tumor volume SE of the mean ($mm^3$) | 45 | 61 | 101 | 87 | 134 | 252 | 380 | 474 | 654 |
| | | | | | | | | | |
| AP-1 | Day 13 | Day 15 | Day 17 | Day 19 | Day 21 | Day 23 | Day 25 | Day 27 | Day 29 |
| Number of mice | 18 | 18 | 17 | 17 | 17 | 17 | 17 | 17 | 16 |
| Tumor volume Minimum, $mm^3$ | 0 | 0 | 48 | 100 | 168 | 336 | 384 | 540 | 486 |
| Tumor volume Maximum, $mm^3$ | 378 | 560 | 990 | 960 | 1950 | 2080 | 2970 | 4284 | 5280 |
| Tumor volume Mean ($mm^3$) | 127 | 183 | 342 | 430 | 728 | 911 | 1213 | 1938 | 2413 |
| Tumor volume SE to the mean ($mm^3$) | 20 | 34 | 60 | 61 | 117 | 121 | 152 | 270 | 364 |
| P-value | <0.05 | <0.05 | <0.01 | <00001 | <0.0001 | <0001 | <0.001 | <0.0001 | <0.0001 |

FIGURE 13

Descriptive Data Summary. LL2 Tumor Growth Rate in C57BL/6 Mice Treated with AP-8 versus Vehicle

| Groups | Vehicle | | | | | | AP-8 | | | | | |
|---|---|---|---|---|---|---|---|---|---|---|---|---|
| Days | 14 | 16 | 18 | 21 | 23 | 25 | 14 | 16 | 18 | 21 | 23 | 25 |
| Number of mice | 10 | 10 | 10 | 10 | 8 | 8 | 10 | 10 | 10 | 10 | 10 | 10 |
| Tumor volume Minimum, mm$^3$ | 409 | 627 | 1308 | 1635 | 2232 | 2265 | 88 | 107 | 279 | 499 | 787 | 1000 |
| Tumor volume Maximum, mm$^3$ | 929 | 1345 | 1860 | 3711 | 4639 | 4948 | 361 | 369 | 841 | 1045 | 2359 | 2532 |
| Tumor volume Mean (mm$^3$) | 639 | 885 | 1525 | 2650 | 3346 | 3803 | 180 | 195 | 506 | 748 | 1580 | 1812 |
| Tumor volume SE to the mean (mm$^3$) | 45 | 68 | 71 | 229 | 291.6 | 365 | 26 | 26 | 55 | 50 | 125 | 151 |
| P-value (AP-8 vs. Vehicle) | | | | | | | <0.0001 | <0.0001 | <0.0001 | <0.0001 | <0.01 | <0.01 |

B

| Normalized Tumor Volume | Vehicle | Taxol | Gemcitabine | AP-8 |
|---|---|---|---|---|
| Week 2 (Day 14) | 2.95±0.44 | 1.72±0.26*, ## | 1.42±0.21**, # | 0.86±0.10**** |
| Week 4 (Day 28) | 5.24±0.92 | 2.50±0.53*, ## | 2.05±0.29***, ## | 1.01±0.12**** |
| Week 8 (Day 56) | 11.44±3.37 | 4.94±1.09# | 3.35±0.58** | 1.98±0.23** |

SYNTHETIC CINCHONA ALKALOIDS AGAINST CANCER

FIELD

The invention relates to novel trimeric cinchona alkaloid compounds, as potent anti-cancer agents.

BACKGROUND

Cancer continues as one of the leading causes of death at any age (C. Fitzmaurice et at, 2019, *JAMA Oncol.*, 5:1749-1768). Cancer is associated with high morbidity and mortality and is the second leading cause of death in the US. In 2017, there were 24.5 million incident cancer cases worldwide and 9.6 million cancer deaths (C. Fitzmaurice et al., 2019, *JAMA Oncol.*, 5:1749-1768). The most common causes of cancer deaths for men were tracheal, bronchus, and lung (TBL) cancer (1.3 million deaths and 1.5 million incident cases), including non-small cell lung cancer (NSCLC). The leading cause of cancer deaths for women was breast cancer (601,000 deaths), which was the second most incident cancer (1.9 million incident cases). There is an urgent need for the development and analysis of novel, effective anti-cancer agents. Considerable efforts are underway to develop new chemotherapeutic agents for more effective anti-cancer therapy (H. Rafei et al., 2020, Br J. Haematol., 188: 207-223; A. Lee, F-C Lee, 2020, Front Med. 14: 273-283; R. K. Vaddepaly, et al., 2020, Cancers 12: 738; F. M. Uckun, et al., EBioMedicine 39:612-620; F. M Uckun et al., 2019, Cancers 1:12; F. M. Uckun et al., J. Clin. Invest. 2015, 125:1006-18; F. M. Uckun et al., 2015, EBiomedicine 2:554-62; F. M. Uckun et al., 2011, Brit J. Hematol. 153: 741-752; F. M. Uckun et al., 2013, Blood 121:4348; F. M. Uckun, 2010, Brit J. Hematol. 149:508-17; F. M. Uckun et al., 2010, Proc Natl Acad Sci. USA 107:2902-7).

B-lineage acute lymphoblastic leukemia (B-ALL) is the most common form of cancer in children and adolescents (1-3). A number of new therapies have been approved by the US Food and Drug Administration in the past 5 years, including blinatumomab in 2014, inotuzumab ozagamicin in 2017 and tisagenlecleucel in 2017 for relapsed/refractory ALL. This has led to tremendous improvement in long-term survival of more than 50% in patients with precursor B-ALL [50-70% in patients with Philadelphia chromosome (Ph)-positive ALL)], 50-60% in T-ALL and 80% in mature B-ALL. Research is ongoing to optimize the benefit of targeted therapeutics with the goal of decreasing the use of cytotoxic therapies (H. Rafei et al., 2020, Br J. Haematol., 188: 207-223).

Currently, the major challenge in the treatment of B-ALL is to cure patients who have relapsed despite intensive frontline chemotherapy (F. M. Uckun et al., 2011, Br. J. Haematol., 153:741-752; F. M. Uckun et al., 2015, J Clin Invest., 125:1006-18). Chemotherapy resistance at relapse is a major obstacle to the success of contemporary "salvage" regimens, since only a minority of relapsed BPL patients become long-term disease-free survivors even after very intensive radiochemotherapy in the context of hematopoietic stem cell transplantation. There is an urgent and unmet need to identify new drug candidates capable of destroying chemotherapy-resistant B-ALL cells. Likewise, patients with relapsed T-lineage ALL (T-ALL) have less than 25% event-free and overall survival rates on contemporary treatments.

Prostate cancer, the most common type of cancer among men, is the second leading cause of cancer-related deaths (C. Fitzmaurice et at, 2019, JAMA Oncol., 5:1749-1768). Advanced prostate cancer has a dismal outcome, and patients with metastatic disease are in urgent need for therapeutic innovations. Treatment of androgen deprivation by both chemical and surgical castration is initially useful in the treatment of metastatic prostate cancer (PC), but patients ultimately enter into the metastatic, castration-resistant prostate cancer (mCRPC) stage, where there is no effective treatment available.

Likewise, advanced and metastatic breast cancer patients, especially those with triple-negative breast cancer (TNBC) are in urgent need for therapeutic innovations (K. J. Chavez et al., 2010, Breast Dis., 32: 35-48).

The prognosis of high-grade gliomas (HGG) has not significantly improved despite recent advances in neurosurgery, chemotherapy, immune-oncology, and radiation therapy (F. M. Uckun, et at, 2019, Cancers (Basel) 11(12). pii: E1892. doi: 10.3390/cancers11121892). The average overall survival of patients with glioblastoma multiforme (GBM) is merely 10-12 months. Most patients experience the recurrence or progression of their disease within 12 months after frontline therapy and face a dismal outcome with no effective therapy available. Therefore, effective salvage therapies are needed for recurrent/refractory HGG patients who have failed their first line standard therapy.

The bark of various Cinchona species contains 4 major quinoline alkaloids, namely quinine (QN), quinidine (QD), cinchonidine (CD), and cinchonine (CN) (P. J. Boratynski, 2015, Mol Divers, 19:385-422; R. T. Brown and D. Curless, 1986, Tetrahedron Letters, 27: 6005-6008; M. Ihara et at, 1988, J. Chem. Soc. Perkin Trans 1, 1277-1281; M. M. Mattock and P. Peters, 1975, Annals of Tropical Medicine and Parasitology, 69: 449-462). Cinchona alkaloids have been used in organic chemistry to catalyze chemical reactions (H. C. Kolb et al., 1994, Chem. Rev. 94, 2483-2547; J. A. Baldwin, M. D. McLeod, 2002, J. Chem Soc. Perkin Trans. 1: 2733-2746). It has been known that many of the alkaloids affect a broad spectrum of cellular targets and metabolic pathways leading to cytotoxicity (S. Schläger, B. Drager, 2016, Curr Opin Biotechnol., 37: 155-64; S. R. Chemler, 2009, Curr Bioact Compd. 5: 2-19; H. Tao, et al., 2020, Recent Patents on Anticancer Drug Discovery, 15: 2-13; M. Cuendet, J. M. Pezuto 2007, [In] Modern Alkaloids: Structure, Isolation, Synthesis and Biology, pp. 25-52). Rosenkranz et al (V. Rosenkranz, M. Winke, 2008, Molecules, 13, 2462-2473) reported the influence of alkaloids on the programmed cell death in blood stream forms of trypanosomes. They concluded that the pro-apoptotic activity of these alkaloids is related to the inhibition of protein synthesis, to intercalate DNA, to disturb membrane fluidity or to inhibit microtubule formation. They also reported that alkaloids induce apoptosis in a human promyelocytic leukemia cell line (V. Rosenkranz, M. Z. Winke, 2007, Naturforsch., 62c: 458-466).

Hydrochinconine, cinchonine and quinidine have been shown to reverse multi-drug resistance and enhance chemotherapy sensitivity of human cancer cells (E. Solary et al. 2000, Leukemia 14, 2085-2094; S. Y. Lee et al., 2011, Environmental Toxicology, 26: 424-431). Other studies have shown that quinolones can cause terminal differentiation of undifferentiated cancer cells (A R Martirosyan, A. R. et al., 2004, Biochemical Pharmacology, 68, 1729-1738). The stereoisomers QN and QD as well as their reduced forms, dihydroquinidine (DHQD) and dihydroquinine (DHQ) are naturally occurring cinchona alkaloids that lack anti-cancer activity (F. M. Uckun, et al., 2010, *Proc. Natl. Acad. Sci. USA* 107: 2902-2007). The modification of these cinchona alkaloids at their $C_9$-OH moiety yielded derivatives with varying levels of cytotoxic activity against human cancer cells. Uckun et al. recently reported a C2-symmetric cinchona alkaloid derivative, 1,4-Bis (9-0 dihydroquinidinyl) phthalazine/hydroquinidine 1,4-phathalazinediyl diether (C-61), as a first-in-class anti-leukemic compound capable of inhibiting the anti-apoptotic SYK-STAT3 signaling in leukemia cells (F. M. Uckun, F. M. et al., 2010, Proc. Natl. Acad. Sci. USA 107(7): 2902-7; F. M. Uckun, F. M. et al., 2010, British Journal of Haematology 149(4): 508-17). A liposomal nanoformulation of C61 exhibited potent anti-leukemic activity both in vitro and in vivo (F. M. Uckun, F. M. et al., 2013, Blood. 121:4348-54; D. E. Myers et al., 2014, Integr Biol (Camb), 6:766-80; F. M. Uckun, et al., 2015, EBioMedicine. 2:554-62). The identification of novel cinchona alkaloids with potent cytotoxicity against a broad spectrum of cancer types, including TNBC, CRPC, GBM, melanoma, lung cancer, and leukemia/lymphoma may through lead optimization and translational research lead to the development of a new class of potent new anti-cancer agents for difficult to treat forms of cancer.

We are now reporting the discovery, synthesis and anti-cancer cell activity of eight novel trimeric cinchona alkaloid compounds, namely 2,4,6-Tri(9-O-cinchoninyl)pyrimidine (AP-1), 2,4,6-Tri(9-O-cinchonidinyl)pyrimidine (AP-2), 2,4,6-Tri(9-O-quininyl)pyrimidine (AP-3), 2,4,6-Tri (9-O-quinidinyl)pyrimidine (AP-4), 2,4,6-Tri (9-O-dihydrocinchoninyl)pyrimidine (AP-5), 2,4,6-Tri (9-O-dihydrocinchonidinyl)pyrimidine (AP-6), 2,4,6-Tri (9-O-dihydroquininyl)pyrimidine (AP-7), and 2,4,6-Tri (9-O-dihydroquinidinyl)pyrimidine (AP-8). These discoveries establish for the first time trimeric cinchona alkaloid compounds as a new class of anti-cancer drugs with broad-spectrum and potent activity against cancer cells. The examples presented herein demonstrate the clinical impact potential of trimeric cinchona alkaloids as a new class of potent new anti-cancer agents for difficult to treat forms of cancer.

Furthermore, Cinchona alkaloids, including trimeric cinchona alkaloids as well as their polymers can be used as catalysts of complex chemical reactions in organic chemistry, for example for the enantioselective desymmetrization of cyclic anhydrides, asymmetric synthesis of amino acids (Ayyanar Siva, Eagambaram Murugan. Synthesis 2005; 17:2927-2933; Hyeung-geun Park et al. Tetrahedron Letters, Volume 42, Issue 28, 2001, Pages 4645-4648; Shohei Takata et al., RSC Adv., 2016, 6, 72300-72305; Masud Parvez et al., Macromolecules 2014, 47, 6, 1922-1928; Marcelli, T. 2007, UvA-DARE (Digital Academic Repository). https://pure.uva.nl/ws/files/4416997/52576_marcelli_thesis.pdf

SUMMARY

Synthetic trimeric cinchona alkaloid compounds having the chemical structure Formula I and II were synthesized and examined for their cytotoxic effects on cancer cells, including human leukemia/lymphoma, breast cancer, prostate cancer, skin cancer/melanoma and brain cancer/glioblastoma cells. Synthetic lead compounds of Formula II, AP-1, AP-5, and AP-8 were found to exhibit potent cytotoxic activity against cancer cells at nanomolar to low micromolar concentrations in vitro. They also were found to be capable of arresting tumor growth in vivo in multiple animal models.

COMPOUNDS

The invention provides a trimeric cinchona alkaloid compound of Formula I that can be synthesized by coupling three molecules of cinchona alkaloids to one molecule of linker, for example trichloro pyrimidine. The compounds of the invention have the general structure shown in Formula I, wherein R is, independent of R', H, Me, Et, Pr, Bu, tBu, Ph, PhCH$_2$, OH, OMe, OEt, OPr, OBu, OtBu, OPh, OCH$_2$Ph; R' is, independent of R and R' CH=CH$_2$, Me, Et, Pr, Bu, tBu, Ph, PH CH$_2$, OH, OMe, OEt, OPr, OBu, OtBu, OPh, or OCH$_2$Ph; (see abbreviation list) or a pharmaceutically acceptable salt thereof.

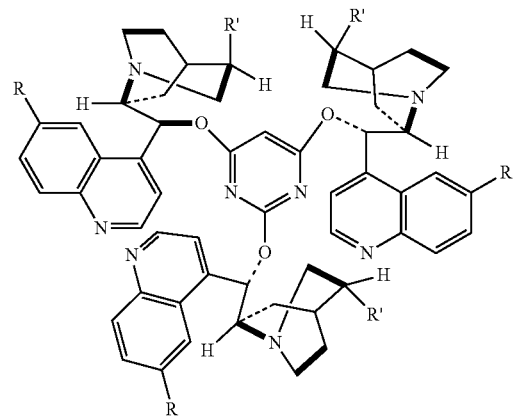

| R | R' | Cinchona alkaloid | Product |
|---|---|---|---|
| H | CH=CH$_2$ | Cinchonidine | AP-2 |
| OCH$_3$ | CH=CH$_2$ | Quinine | AP-3 |
| H | CH$_2$CH$_3$ | Hydrocinchonine | AP-6 |
| OCH$_3$ | CH$_2$CH$_3$ | Hydroquinicline | AP-7 |
| H | CH=CH$_2$ | Cinchonine | AP-1 |
| OCH$_3$ | CH=CH$_2$ | Quinicline | AP-4 |
| H | CH$_2$CH$_3$ | Hydro cinchonine | AP-5 |
| OCH$_3$ | CH$_2$CH$_3$ | Hydro Quinicline | AP-8 |

Another embodiment of the present invention provides compositions formulated for delivery of the cytotoxic cinchona alkaloid compounds to a subject as a pharmaceutical composition. The compounds of the invention are combined with a suitable carrier to form compositions suitable for use in cancer therapy.

A further embodiment of the present invention provides methods to inhibit the growth or induce apoptosis of cancer cells, by administering to a subject or contacting cancer cells with an effective amount of a compound or composition of the present invention.

A further embodiment of the present invention provides a method for the synthesis of novel trimeric cinchona alkaloid derivatives as described in the Examples herein below.

The above summary of the present invention is not intended to describe each disclosed embodiment or every implementation of the present invention. The drawings and the detailed description which follow more particularly exemplify these embodiments.

The invention provides a trimeric cinchona alkaloid compound of Formula I that can be synthesized by coupling three molecules of cinchona alkaloids to one molecule of linker, for example trichloro pyrimidine. The compounds of the invention have the general structure shown in Formula I, wherein R is, independent of R', H, Me, Et, Pr, Bu, tBu, Ph, PhCH$_2$, OH, OMe, OEt, OPr, OBu, OtBu, OPh, OCH$_2$Ph; R' is, independent of R and R' CH=CH$_2$, Me, Et, Pr, Bu, tBu, Ph, PH CH$_2$, OH, OMe, OEt, OPr, OBu, OtBu, OPh, or OCH$_2$Ph; (see abbreviation list) or a pharmaceutically acceptable salt thereof.

Formula I

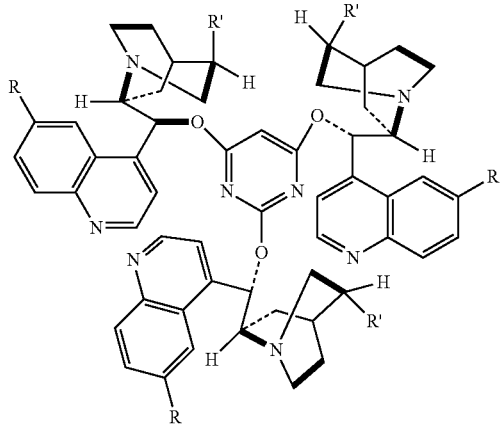

One preferred compound of the present invention is Compound AP-1 or a pharmaceutically acceptable salt thereof:

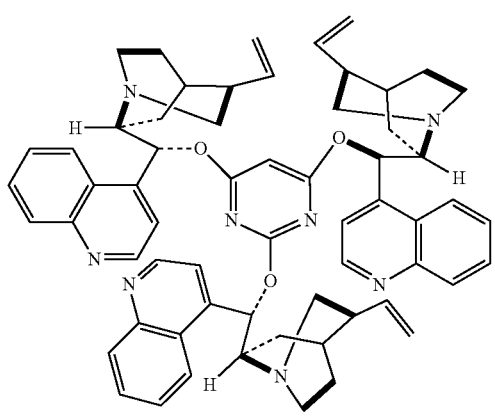

One preferred compound of the present invention is Compound AP-5 or a pharmaceutically acceptable salt thereof:

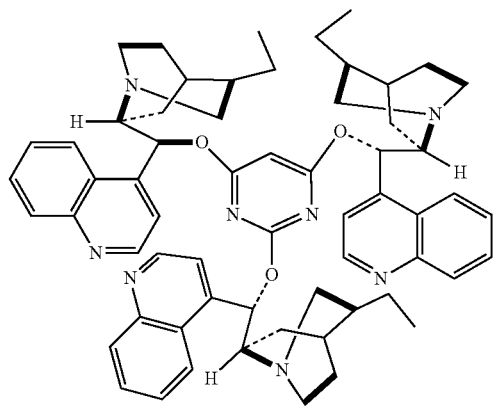

One preferred compound of the present invention is Compound AP-8 or a pharmaceutically acceptable salt thereof:

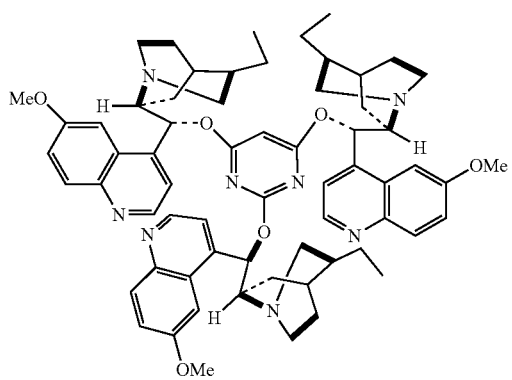

The invention also provides compounds wherein the alkaloid moiety may be chosen independently from any one of the following compounds, or any appropriately substituted heterocyclic derivative or a pharmaceutically acceptable salt thereof: Cinchonidine, Quinine, Cinchonine, Quinidine.

The invention also provides trimeric cinchona alkaloid compounds of Formula II wherein the linker moiety L may be chosen independently from any one of the following compounds; (see linker list) and any appropriately substituted heterocyclic derivative or a pharmaceutically acceptable salt thereof Formula II

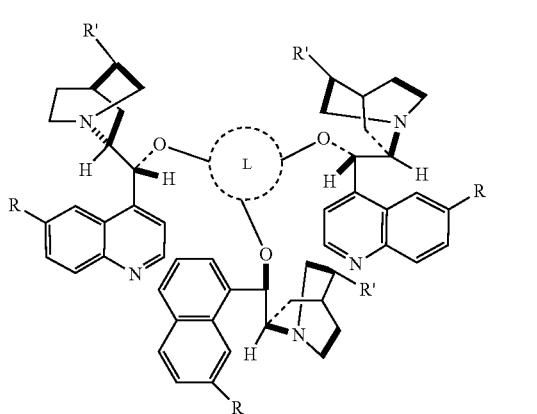

"L" represents the linker moiety (see linker list) which may comprise of halo substituted heterocycles not limited to the following:

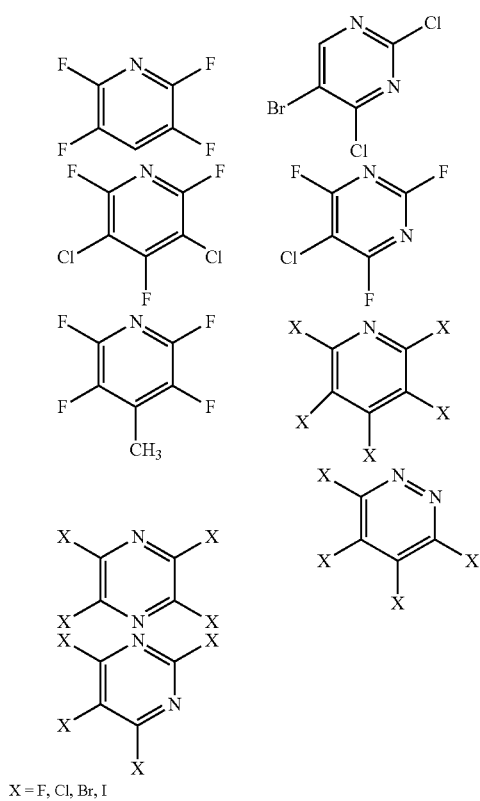

X = F, Cl, Br, I

This invention also provides compounds of Formula II, wherein the linker moiety L are (i) molecules that contain bicyclic, tricyclic and tetracyclic ring attached heterocycles or (ii) molecules that contain hetero atoms including but not limited to N, O, S, Se, Te; or (iii) molecules that contain halogen atoms including F, Cl, Br, or I; or pharmaceutically acceptable salts thereof The invention also provides a pharmaceutical composition comprising a compound of Formula I, or a compound of Formula II or their salts and a pharmaceutically acceptable carrier, including but not limited to liposomes, fusion proteins, target-specific ligands or monoclonal antibodies.

The invention provides a method for treating cancer in a mammal comprising administering to the mammal in need of such treatment an effective amount of a compound in Formula I, Formula II, or a pharmaceutically acceptable salt thereof, or a pharmaceutical composition thereof The invention provides a method for treating a human cancer patient, especially a patient with breast cancer, prostate cancer, glioblastoma multiforme, non-small cell lung cancer, leukemia, or lymphoma with an effective amount of a compound in Formula I or Formula II; or a pharmaceutically acceptable salt thereof, or a pharmaceutical composition thereof Particular embodiments of the claimed compounds, for example Compound Formula I are described below in the Detailed Description, Examples, and Claims. Particularly preferred compounds of the invention are Formula I compounds and derivatives.

Additional Embodiments of the invention are described more fully below:

BRIEF DESCRIPTION OF THE DRAWINGS

The invention may be more completely understood in consideration of the following detailed description of various embodiments of the invention in connection with the accompanying Figures, in which:

FIG. 13 further demonstrates that AP-1 exhibits potent anti-cancer activity in a syngeneic mouse model of K-Ras mutant non-small cell lung cancer (NSCLC). As evidenced by the depicted tumor growth curves and the descriptive summary data table for the $3^{rd}$ experiment, the average tumor volume in mice treated with AP-1 injections remained significantly smaller than the average tumor volume in vehicle-treated control mice. A two-way analysis of variance (ANOVA) model was used with Geisser-Greenhouse correction to evaluate the statistical significance of the overall effect of drug treatment across all time points and demonstrated a pronounced overall inhibitory effect of AP-1 on tumor growth. The P-value for each time point was computed using Sidak's multiple comparisons test and confirmed the statistical significance of the differences in the average tumor volume for each time point (*$p<0.05$; $p<0.01$; *$p<0.001$; ****$p<0.0001$).

DETAILED DESCRIPTION

Figure 1:
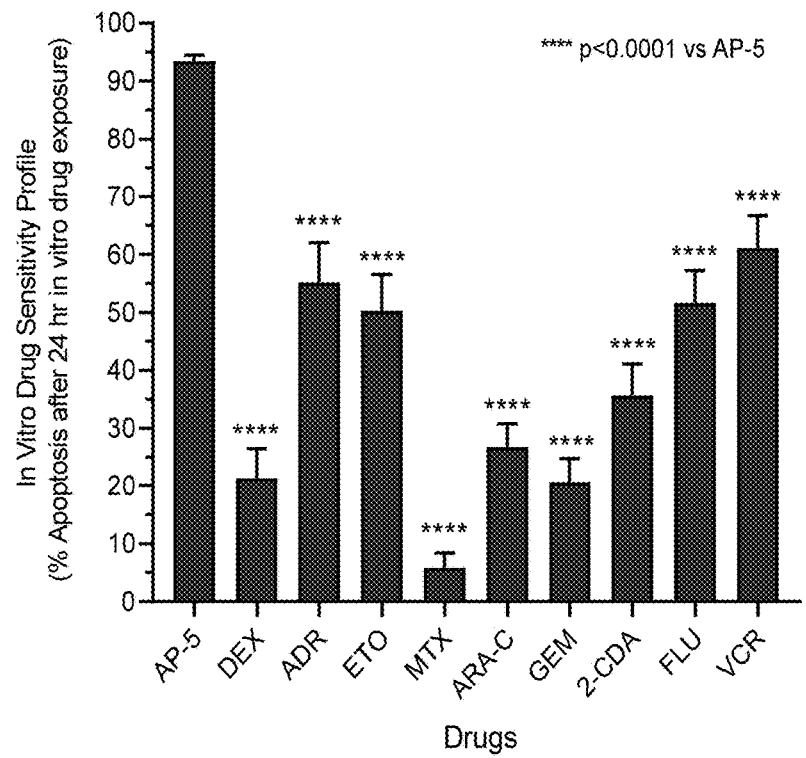
FIG. 1: This figure demonstrates that AP-5 induces apoptosis in primary leukemia and lymphoma cells. The depicted bars represent the mean and standard error values for the % Apoptosis in primary leukemia cells from 26 patients achieved after 24 hour in vitro exposure to each of the drugs tested. Statistical significance between the two groups is shown by the depicted superscripts above the plots were computed using the independent samples T-test (**** $p<0.0001$). Also depicted is a descriptive data summary.

The present invention includes synthetic trimeric cinchona alkaloids having the structure II shown above, as a cytotoxic compound, useful in pharmaceutical compositions to arrest tumor growth and induce cell death or apoptosis in cancer cells. The examples below establish synthetic trimeric cinchona alkaloids as useful therapeutic agents against cancer.

The invention also provides novel trimeric cinchona alkaloid derivatives having potent activity as cytotoxic agents against cancer cells, including leukemia, prostate cancer, breast cancer and brain cancer cells, and particularly against multi-drug resistant cancer cells, for example, human B-lineage acute lymphoblastic leukemia cells, glioblastoma cells, and BT-20 human breast cancer cells. In addition, specific novel cinchona alkaloid derivatives of the invention are potent inhibitors of tumor clonogenic growth necessary for tumor progression and for tumor cell metastases. While the present invention is not so limited, an appreciation of various aspects of the invention will be gained through the description and the Examples provided below.

Definitions

All scientific and technical terms used in this application have meanings commonly used in the art unless otherwise specified. As used in this application, the following words or phrases will have the meanings:

As used herein, "pharmaceutically acceptable salt or carrier" includes any material which, when combined with a compound of the invention, allows the compound to retain biological activity, for example the ability to induce apoptosis of cancer cells, and is non-reactive with the subjects immune system. Examples include, but not limited to, any of the standard pharmaceutical carriers, for example a phosphate buffered saline solution, water, emulsions (for example) oil/water emulsions, and various types of wetting agents. Also included are PEG'ylation, and liposome systems as useful carriers of the compositions of the invention. In addition, carrier molecules, for example specific anti-cancer antigen antibodies, and ligands, for example EGF, can be used to carry the compound to the target cells. Compositions comprising such carriers, including composite molecules, are formulated by well-known conventional methods (see for example, Remington's Pharmaceutical Sciences, Chapter 43, $14^{th}$ Ed., Mack Publishing Co., Easton, Pa.).

"Treating", Treatment or "to treat" in the context of this invention means to inhibit or block at least one symptom that characterizes a pathologic condition., in a mammal threatened by, or afflicted with, the condition. In context of cancer therapy, treatments include prevention of tumor cell death, and increased apoptosis. Treatment also includes the prevention of cancer cell adhesion and migration into tissues. "Inhibit" means to reduce by a measurable amount, or to prevent entirely.

"Multi-Drug Resistant Cancer Cells" means one or more type of cancer cell which is resistant to treatment with one or more chemotherapeutic agent. "Therapeutically effective amount" is a dose which provides some therapeutic benefit on administration, including in the context of the invention, inhibition of cancer cell growth and/or proliferation, prevention or inhibition of apoptosis, reduction in tumor mass, prevention of cancer cell adhesion and/or migration; and increase in patient longevity.

Cytotoxic Compounds

As shown in the Examples below, synthetic trimeric cinchona alkaloids were tested for cytotoxic activity against cancer cells using MTT and apoptosis assays using confocal microscopy or flow cytometry. Trimeric cinchona alkaloid compounds inhibited growth of cancer cells and caused their apoptotic destruction at nanomolar to low micromolar concentrations.

Useful compounds of the invention are tested for cytotoxicity as described in the Examples below. The test methods are well known as standard methods in the field of cancer therapeutics, and have been well established as effective assays for predicting useful pharmaceutical agents for the treatment of cancer.

In the method of the invention, cancer cells are contacted with approximately nanomolar-micromolar concentrations of the compounds in vitro to cause cytotoxicity to cancer cells. In another method of invention, animal models of cancer are used to evaluate the therapeutic anti-cancer efficacy of the compounds.

Prodrug

The term "prodrug" is meant to define a conjugate molecule, where the two molecular species are a hydroxy-substituted cinchona alkaloid derivative and a moiety which renders the conjugate biologically inert, yet which has pharmacological activity upon bioactivation. Prodrugs include, for example, the ethoxy derivatives of the trimeric cinchona alkaloid compounds, as shown below (see Formula Prodrug-I and Prodrug-II), covalently attached to an ethoxy group which can be cleaved, for example, enzymatically by esterases or though acid or base catalyzed hydrolysis Prodrug-I

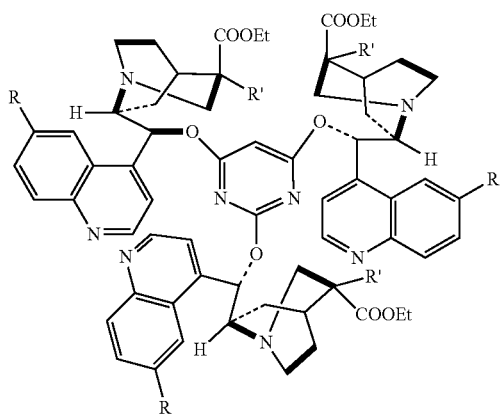

Prodrug-II

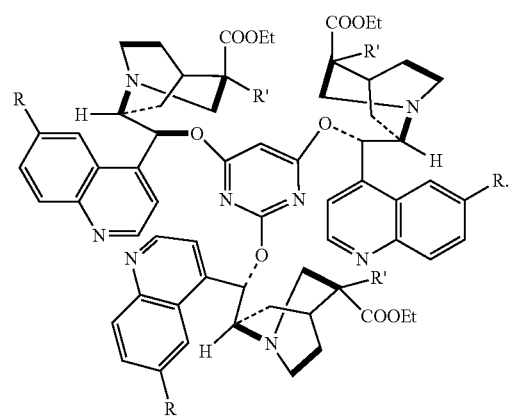

Prodrugs useful in the invention include those that contain, for example, an ester or amide, acyl derivative. The corresponding prodrug of AP-5 is shown below as an example:

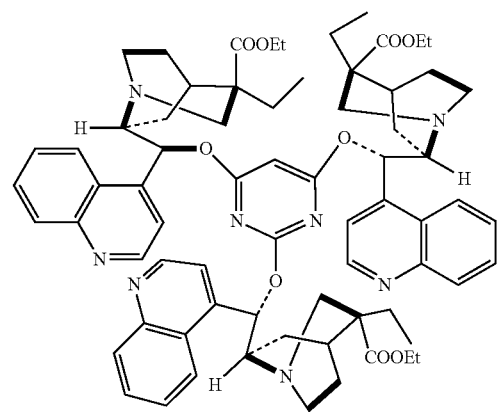

Administration Methods

The compounds in the present invention as well as their conjugates can be formulated as pharmaceutical compositions and administered to a mammalian host, including a human patient in a variety of forms adapted to the chosen route of administration and suitable for administration of the small molecule or its conjugate. The compounds are preferably administered in combination with a pharmaceutically acceptable carrier, and may be combined with or conjugated to specific delivery agents, including targeting antibodies and/or cytokines. It is preferred that the compositions of the present invention be administered parenterally, i.e., intravenously or intraperitoneally, by the infusion or injection. The compounds can also be administered intratumorally for example using convection enhanced delivery systems for brain tumors (F. Uckun et al., Cancers 2019; 1(12). pii: E1892. doi: 10.3390/cancers11121892).

In one embodiment of the invention, the compounds may be administered directly to a tumor by tumor injection; by injecting the compound into the brain, e.g., into ventricular fluid; or by systemic delivery by intravenous injection. The compounds of the invention, including the conjugates, are of a size and composition expected to have ready access to the brain across the blood-brain barrier.

The compounds can be administered by known techniques, for example orally, parentally (including subcutaneous injection, intravenous, intramuscular, intraarterial injection or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, for example sterile injectable aqueous or oleaginous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, for example sterile oils, including synthetic mono- or diglycerides, and fatty acids, including oleic acid.

For rectal administration as suppositories, the compositions can be prepared by mixing with a suitable non-irritating excipient, for example cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes. More preferably, the compounds of the present invention are administered parenterally, i.e., intravenously or intraperitoneally, by infusion or injection. In one embodiment of the invention, the compounds may be administered directly to a tumor by tumor injection; or by systemic delivery by intravenous injection.

Solutions or suspensions of the compound and their conjugates can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions, or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage.

The liquid carrier or vehicle can be a solvent or liquid dispersion medium comprising, for example, water, ethanol, a polyol for example glycerol, propylene glycol, or liquid polyethylene glycols and the like, vegetable oils, non-toxic glyceryl esters, and suitable mixtures thereof. The proper fluidity can be maintained, for example, by the formation of liposomes, by the maintenance of the required particle size, in the case of dispersion, or by the use of nontoxic surfactants.

The prevention of the action of microoganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monostearate hydrogels and gelatin.

Sterile injectable solutions are prepared by incorporating the compound or conjugate derivatives in the required amount in the appropriate solvent with various other ingredients as enumerated above and, as required, followed by filer sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Conjugation to a Targeting Moiety

The compound of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated. The term "conjugate" means a complex formed with two or more compounds.

The phrase "targeting moiety" means a compound which serves to deliver the compound of the invention to a specific site for the desired activity. Targeting moieties include, for example, molecules which specifically bind molecules present on a cell surface. Such targeting moieties useful in the invention include antibodies (example: monoclonal antibodies, recombinant antibodies, bispecific antibodies or fragments thereof) directed to a cancer associated cell surface antigen. Cytokines, including interleukins, factors for example epidermal growth factor (EGF), and the like, are also specific targeting moieties known to bind cancer cells expressing high levels of their receptors. Particularly useful targeting moieties for targeting the compounds of the invention to cells for therapeutic activity include those ligands that bind antigens or receptors present on the tumor cells to be treated. For example, antigens present on B-lineage cancer cells, for example CD19, can be targeted with anti-CD19 antibodies. Antibody fragments, including single chain fragments, can also be used. IL4 can also be used to target B-cells. Cancer cells expressing EGF or IGF receptors can for example be targeted with the binding ligand EGF or IGF. Other such ligand-receptor binding pairs are known in the scientific literature for specific cancers. Methods for producing conjugates of the compounds of the invention and the targeting moieties are known.

Useful Dose

When used in vivo to selectively kill cancer cells or to inhibit cancer cell growth or metastasis, the administered dose is that effective to have the desired effect, e.g., sufficient to reduce or eliminate cancer cells, or sufficient to inhibit growth of tumor cells. Appropriate amounts can be determined by those skilled in the art, extrapolating using known methods and relationships, from the in vitro data provided in the examples.

In general, the dose of the novel cinchona alkaloids effective to achieve cancer cell apoptosis, inhibition of cancer cell growth, and increased subject survival time, is that which administers nanomolar to micromolar amounts of the compound to the cells, preferably 100 nanomolar or greater. The required dose can be lessened by conjugation of the compound to a targeting moiety for example, to preferably 50 nanomolar or greater concentrations.

The effective dose to be administered will vary with conditions specific to each patient. In general, factors such as the disease burden, tumor location (exposed or remote), host age, metabolism, sickness, prior exposure to drugs, and the like contribute to the expected effectiveness of a drug. One skilled in the art will use standard procedures and patient analysis to calculate the appropriate dose, extrapolating from the data provided in the examples.

In general, a dose which delivers about 0.01-100 mg/kg body weight is expected to be effective, although more or less may be useful. In addition, the compositions of the invention may be administered in combination with other anti-cancer therapies. In such combination therapy, the administered dose of the trimeric alkaloid derivatives would be less than for single drug therapy.

Cancer Treatment

For the purposes of this invention, a method of treating cancer includes contacting cancer cells with a compound of the invention in order to achieve an inhibition of cancer cell growth, a killing of cancer cells, an/or increased patient survival time. Treatment of cancer, by the method of the invention, also includes the prevention of the growth of cancer cells, thereby inhibiting metastases.

The cytotoxic and tumor growth-inhibiting compound of the invention is suitable for use in mammals. As used herein, "mammals" means any class of higher vertebrates that nourish their young with milk secreted by mammary glands, including, for example, humans, rabbits, and monkeys.

Apoptosis

Apoptosis, or programmed cellular death, is an active process requiring new protein synthesis. Typically, the process requires ATP, involves new RNA and protein synthesis, and culminates in the activation of endogenous endonucleases that degrade the DNA of the cell, thereby destroying the genetic template required for cellular homeostasis. Apoptosis is observed in controlled deletion of cells during metamorphosis, differentiation, and general cell turnover and appears normally to be regulated by receptor-coupled events. For these reasons, apoptosis has been called "programmed cell death" or "cell suicide." While every cell likely has the genetic program to commit suicide, it is usually suppressed. Under normal circumstances, only those cells no longer required by the organism activate this self-destruction program.

Apoptotic cell death is characterized by plasma membrane bleeding, cell volume loss, nuclear condensation, and endonucleolytic degradation of DNA at nucleosome intervals. Loss of plasma membrane integrity is a feature of late stage apoptosis.

Embodiment list. The following list includes particular exemplary embodiment, but does not exclude any other embodiment listed herein.

1. A compound having the structure of Formula I or II, or a pharmaceutically acceptable salt of Formula I or Formula II, the compound of Formula I comprising three alkaloid moieties substituted with R and R' and bound to pyrimidine as a linker, and the compound of Formula II comprising three alkaloid moieties substituted with R and R' and bound to L:

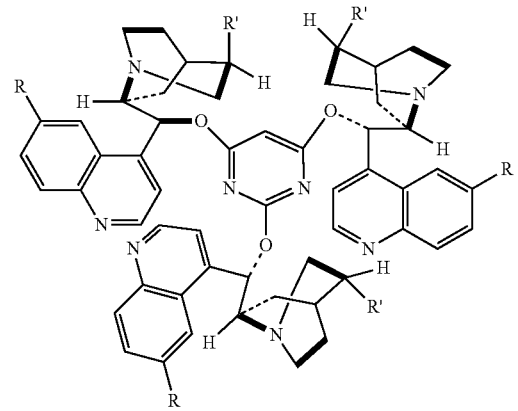

Formula I

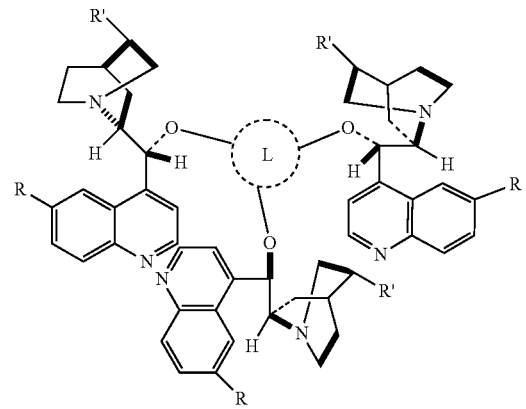

Formula II wherein each R is, independent of R', independently selected from the group consisting of H, Me, Et, Pr, Bu, tBu, Ph, PhCH$_2$, OH, OMe, OEt, OPr, OBu, OtBu, OPh, OCH$_2$Ph; each R' is, independent of R, independently selected from the group consisting of CH=CH$_2$, Me, Et, Pr, Bu, tBu, Ph, PhCH$_2$, OH, OMe, OEt, OPr, OBu, OtBu, OPh, or OCH$_2$Ph; and L represents a linker moiety selected from heterocyclic organic compounds, for example pyrazine, pyridazine, pyrimidine, phthalazine, and their respective derivatives.

2. A compound of embodiment 1, wherein the alkaloid moiety may be chosen independently from any one of the following compounds, or any appropriately substituted heterocyclic derivative or a pharmaceutically acceptable salt thereof: Cinchonidine, Quinine, Cinchonine, Quinidine.

3. The compound of embodiment 1 comprising the structure of Formula II having a tri-substituted cinchona alkaloid, wherein L is chosen independently from any one of the following compounds

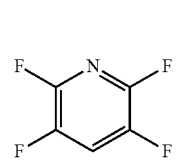 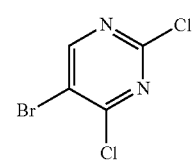

-continued

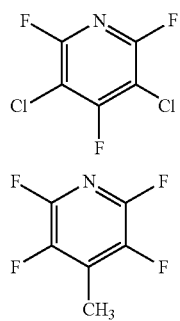

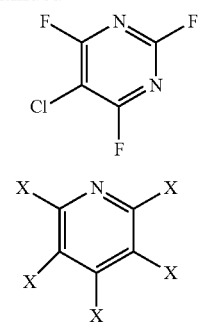

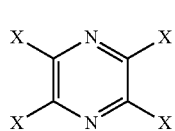

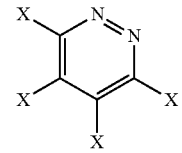

X = F, Cl, Br, I

4. The compound of embodiment 1 comprising the structure of Formula II, wherein the linker moiety L is (i) a molecule that contains a bicyclic, tricyclic or tetracyclic ring attached heterocycle (see linker list) or (ii) a molecule that contains hetero atoms selected from the group consisting of N, O, S, Se, and Te; or (iii) a molecule that contains a halogen atom selected from the group consisting of F, Cl, Br, and I; or a pharmaceutically acceptable salt thereof.

5. The compound of embodiment 1, wherein the compound is 2,4,6-Tri(9-O-cinchoninyl) pyrimidine (AP-1)

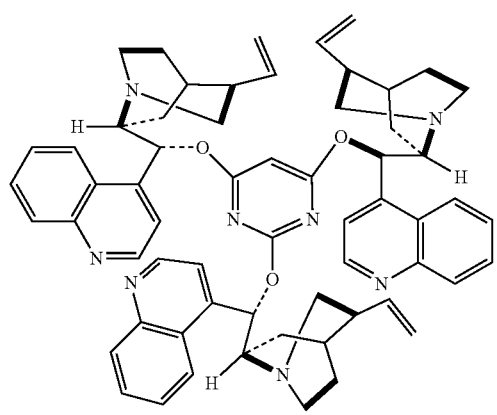

or a pharmaceutically acceptable salt thereof.

6. The compound of embodiment 1, wherein the compound is 2,4,6-Tri(9-O-cinchonidinyl)pyrimidine (AP-2)

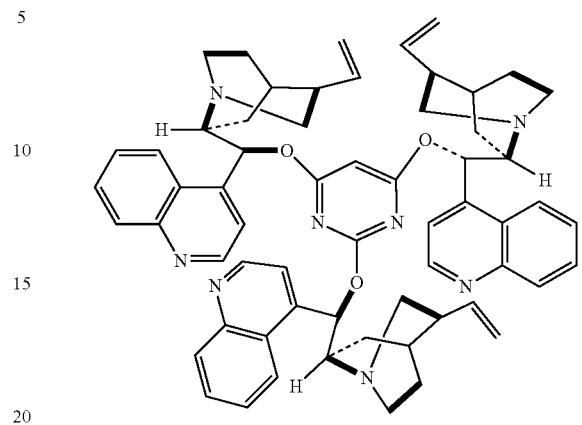

or a pharmaceutically acceptable salt thereof.

7. The compound of embodiment 1, wherein the compound is 2,4,6-Tri(9-O-quininyl)pyrimidine (AP-3)

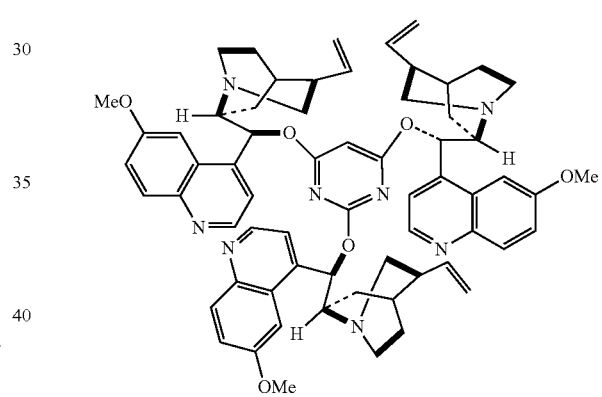

or a pharmaceutically acceptable salt thereof.

8. The compound of embodiment 1, wherein the compound is 2,4,6-Tri (9-O-quinidinyl)pyrimidine (AP-4)

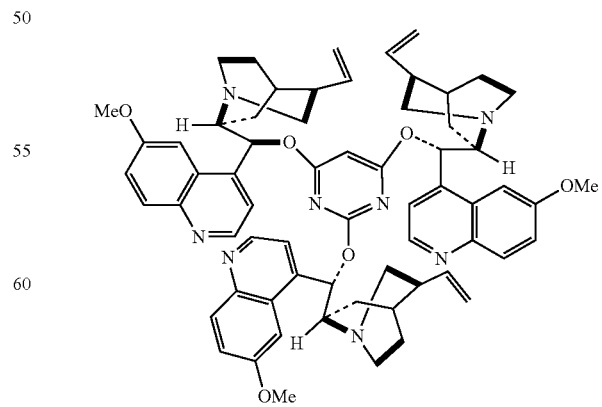

or a pharmaceutically acceptable salt thereof.

9. The compound of embodiment 1, wherein the compound is 2,4,6-Tri (9-O-dihydrocinchoninyl)pyrimidine (AP-5)

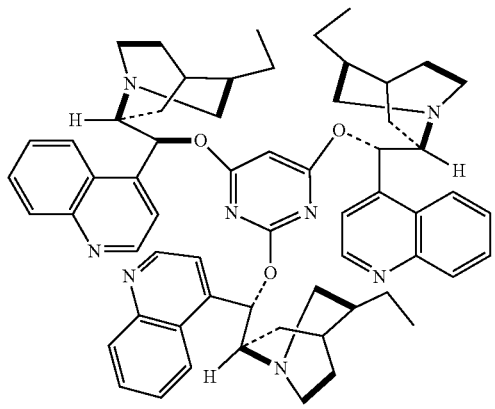

or a pharmaceutically acceptable salt thereof.

10. The compound of embodiment 1, wherein the compound is 2,4,6-Tri (9-O-dihydrocinchonidinyl)pyrimidine (AP-6)

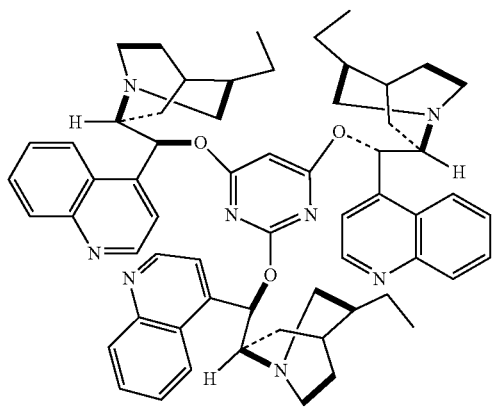

or a pharmaceutically acceptable salt thereof.

11. The compound of embodiment 1, wherein the compound is 2,4,6-Tri (9-O-dihydroquininyl)pyrimidine (AP-7)

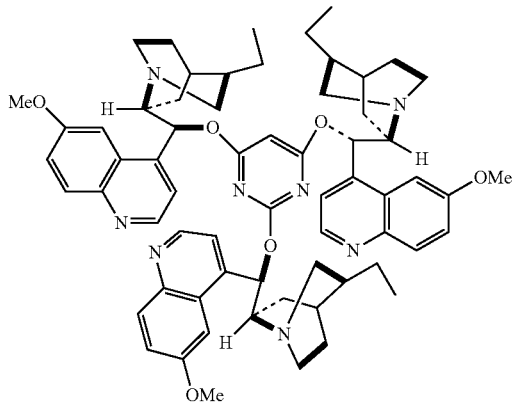

or a pharmaceutically acceptable salt thereof.

12. The compound of embodiment 1, wherein the compound is 2,4,6-Tri (9-O-dihydroquinidinyl)pyrimidine (AP-8)

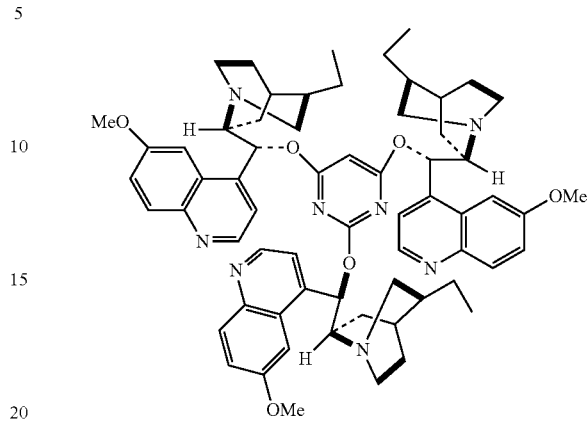

or a pharmaceutically acceptable salt thereof.

13. A pharmaceutical composition comprising effective therapeutic amount of a compound of any one of embodiments 1-12 and a pharmaceutically acceptable carrier.

14. The pharmaceutical composition of embodiment 13, wherein the pharmaceutically acceptable carrier is selected from the group consisting of liposomes, fusion proteins, target-specific ligands or monoclonal antibodies.

15. A composition comprising the compound of embodiment 4 formulated as a prodrug.

16. A method for treating cancer in a mammal comprising administering to the mammal in need of such treatment an effective amount of a compound of any one of claims 1-12 or a pharmaceutically acceptable salt thereof, or a pharmaceutical composition thereof 17. The method of embodiment 16, wherein the mammal is a human cancer patient, preferably a patient with breast cancer, prostate cancer, glioblastoma multiforme, non-small cell lung cancer, leukemia, or lymphoma.

18. A method for treating cells comprising contacting said cells with an effective amount of any compound of embodiments 1-12, a pharmaceutically acceptable salt thereof, or a pharmaceutical composition thereof.

19. The method of embodiment 18, wherein the method of is a method of inducing apoptosis or inhibition of growth of leukemia cells, lymphoma cells, breast cancer cells, prostate cancer cells, or brain tumor cells, and said effective amount is an effective apoptosis-inducing or proliferation-inhibiting amount of the compound, the pharmaceutically acceptable salt thereof, or the pharmaceutical composition thereof 20. The method of embodiment 18, wherein the method is for inhibiting the growth of leukemia cells, breast cancer cells, prostate cancer cells, or brain tumor cells, and said effective amount is an effective inhibitory dose of the compound, the pharmaceutically acceptable salt thereof, or the pharmaceutical composition thereof.

Methods

Medicinal Chemistry. Dihydroquinidine, hydroquinine, quinidine, quinine and cinchonine, trihalosubstituted heterocycles and other cinchona alkaloid derivatives were purchased from Aldrich Chemical Company and used as such without further purification. Solvents and chemicals were purchased from Aldrich, Fluka, or EM Science. Anhydrous solvents were used in moisture sensitive reactions. All air-sensitive reactions were performed in dry glassware under nitrogen atmosphere. All reaction mixtures were stirred magnetically. NMR spectra were recorded on a 300 MHz Varian NMR spectrometer equipped with an auto probe assembly, using $CDCl_3$ with tetramethylsilane as the internal standard for $^1H$ (300 MHz) or solvent as the internal standard for $^{13}C$ (75 MHz). NMR spectra were acquired in $CDCl_3$ at room temperature. Infrared spectra were done in Perkin Elmer 410 portage model instrument using potassium bromide pellets. Mass spectra were taken using a fast atom bombardment mode and high-resolution mass spectra were also acquired to confirm the purity of the materials for biological study. Optical rotation values were obtained from a Polarimeter using sodium lamp line.

Melting points were determined with a Mel-Temp II (Laboratory Devices, Inc., USA) capillary melting point apparatus in open glass capillaries. The values are uncorrected. Analytical thin-layer chromatography (TLC) was performed on Merck precoated glass plates (silica gel 60, $F_{254}$, 250-μm thick), and visualized under 254-nm UV light. Preparative column chromatography was performed using EM silica gel 60, 230-400 mesh. Mass spectral data (MALDI-TOF) were obtained on a G2025A LD-TOF system (Hewlett Packard). MS samples were prepared with 1:1=matrix (30-mM α-cyano-4-hydroxycinnamic acid in 50: 30: 20=acetonitrile: methanol: water): NMR sample in $CDCl_3$. HPLC was carried out with HP 1100 series under the following conditions: a Zorbax SB-C3 column (5 μm, 4.6× 150 mm), mobile phase: buffer (50 mM $NH_4H_2PO_4/H_3PO_4$, pH 2.5)/acetonitrile, flow rate: 1.0 mL/min, wavelength: 235 nm. The yields quoted are isolated yields.

Cell lines and Apoptosis Assays. We used human leukemia/lymphoma cell lines, patient-derived primary leukemia/lymphoma cells as targets to evaluate the anti-leukemic activity of cinchona alkaloids. In vivo leukemia initiating xenograft clones capable of causing disseminated and fatal leukemia in NOD-SCID mice, derived from primary leukemia cells of a patient with relapsed ALL were also used (F. M. Uckun et al., 2015, J Clin Invest 125:1006-18). The triple negative breast cancer cell line BT-20 (K. K. Chavez et al., 2010, Breast Dis. 32:35-48; ATCC HTB-19), the prostate cancer cell line PC-3 (T. K. Shain et al., 2020, Anticancer Drugs; ATCC-CRL 1435), the glioblastoma cell line U87 (R. K. Narla et al., 1998, Clin Cancer Res. 4:1405-14; R. K. Narla et al., 2001, Clin Cancer Res. 2124-33; ATCC-HTB-14), and the melanoma cell line MT24-MET (ATCC CRL-12270) were also used. In addition, the murine non-small cell lung cancer (NSCLC) cell line LL/2 (B. Deskin et al., 2020, Translational Oncology 13:135-45; H. Y. Li et al., 2017, Cancer Immunol. Res. 5:767-77) was used in in vivo experiments.

Apoptotic death was monitored using multiparameter flow cytometry, as previously reported (F. M. Uckun, et al., 2011, British Journal of Haematology, 153:741-752; F. M. Uckun et al., 2015, J Clin Invest., 125:1006-18). Controls included vehicle (PBS) treated cells (CON). Cells were analyzed for apoptosis using the standard quantitative flow cytometric apoptosis assay using the Annexin V-FITC Apoptosis Detection Kit from Sigma. The labeled cells were analyzed on a flow cytometer. The percent apoptosis was calculated using the formula: 100-100×(Percentage of non-apoptotic cells in test sample/Percentage of non-apoptotic cells in untreated control sample). The percentages for Annexin V FITC$^-$PI$^-$ viable cells and Annexin V-FITC$^+$PI$^+$ advanced apoptotic cells for each sample are indicated in the respective quadrants of the depicted two-color fluorescence dot plots. The ability of anti-cancer drugs to cause apoptosis of leukemia cells derived from patients was shown to be predictive of the effectiveness of the same drugs in clinical settings (F. M. Uckun, et al., 2011, British Journal of Haematology, 153:741-752).

Confocal Laser Scanning Microscopy. Cells were treated with cinchona alkaloids or PBS in culture medium for 48 hours. After 48 hr of culture, cells were co-stained with a rabbit polyclonal antitubulin antibody (Green Fluorescence) and the DNA-specific dye Toto-3 (Blue Fluorescence) and examined by laser scanning confocal microscopy using a Bio-Rad MRC-1024 Laser Scanning Confocal Microscope equipped with a Kr/Ar laser (Bio-Rad, Hercules, Calif., USA) mounted on a Nikon Eclipse E800 upright microscope with high numerical aperture objectives (Nikon, Melville, N.Y., USA), as described (F. M. Uckun, et al., 2010, Proc. Natl. Acad. Sci. USA, 107: 2902-7; F. M. Uckun., et al., 2010, British Journal of Haematology, 149: 508-17; F. M. Uckun, et al., 2013, Blood. 121:4348-54; F. M. Uckun et al., 2010, Proc. Natl Acad. Sci. USA 107:16852-57; F. M. Uckun et al., 2012, Proc. Natl Acad. Sci. USA 109:18072-77).

EXAMPLES

The invention may be further clarified by reference to the following examples, which serve to exemplify some of the preferred embodiments, and not to limit the invention in any way.

The invention may be further clarified by reference to the following examples, which serve to exemplify some of the preferred embodiments, and not to limit the invention in any way.

Example 1. Parallel Synthesis of Novel Cinchona Alkaloid-Trisubstituted Pyrimidines Eight cinchona alkaloid-trisubstituted pyrimidines were synthesized in parallel. The cinchona alkaloids used include: cinchonine, cinchonidine, quinine, quinidine, hydrocinchonine, hydrocinchonidine, hydroquinine, and hydroquinidine. Deprotonated cinchona alkaloids substitute the chlorides of 2,4,6-trichloropyrimidine to afford the desired compounds.

Chemistry

Eight cinchona alkaloids were deprotonated by sodium hydride, forming corresponding sodium. alkoxides in butyronitrile in parallel reaction. vessels (Quest 205, Argonaut Technologies). The alkoxides substituted chlorides in 2,4,6-trisubstituted pyrimidine under reflux (bp 117° C.) for two days. The solutions were drained out through the micro-frit (7 μm) bottom of reaction vessels, with concomitant separation from the solids (molecular sieves and unreacted NaH, etc.), After ether extraction and concentration, eight desired compounds, AP-1 to AP-8 (Scheme 1a-b), were obtained in quantitative yields. Two compounds (AP-1 and AP-5) were >95% pure by HPLC. The other six compounds were purified by flash chromatography.

General Procedure for the Synthesis. A round-bottom flask was charged with appropriately chosen alkaloid (3.15 eq), chloro-substituted heterocycle (2 mmol), NaH (6 mol. eq), molecular sieves (4A, 2 g) and acetonitrile or butyronitrile (50 ml). The mixture was refluxed overnight. The reaction mixture was cooled to room temperature, filtered under suction and rinsed with ether. The filtrate was dried over anhydrous magnesium sulfate and filtered and concentrated under reduced pressure. The products were isolated as such or purified by flash chromatography, depending on their purity by HPLC.

The chemical characteristics were as follows:

2,4,6-Tri(9-O-cinchoninyl)pyrimidine (AP-1). mp 260-262° C., IR: 2938, 2876, 1576, 1514, 1452, 1375, 1168, 1060 cm−1; 1H NMR δ 8.85 (d, J=4.5 Hz, 2H), 8.61 (d, J=3.9 Hz, 1H), 8.22 (d, J=8.4 Hz, 2H), 8.17 (d, J=8.4 Hz, 2H), 8.08 (d, J=8.7 Hz, 1H), 7.94 (d, J=8.4 Hz, 1H), 7.76 (t, J=7.2 Hz, 2H), 7.68 (t, J=7.5 Hz, 1H), 7.64 (t, J=7.5 Hz, 2H), 7.47 (t, J=7.5 Hz, 1H), 7.31 (d, J=4.5 Hz, 2H), 6.80 (d, J=4.5 Hz, 1H), 6.52 (d, J=6.3 Hz, 2H), 6.15 (d, J=4.8 Hz, 1H), 5.92-5.73 (m, 3H), 5.78 (s, 1H), 5.10-4.89 (m, 6H), 3.19 (q, J=7.2 Hz, 2H), 2.99 (q, J=4.8 Hz, 1H), 2.62 (q, J=5.4 Hz, 12H), 1.77-1.56 (m, 6H), 1.47-1.36 (m, 12H); 13C NMR δ 171.0, 162.5, 149.7, 149.6, 148.2, 148.1, 145.4, 145.1, 140.4, 140.1, 130.3, 130.2, 128.8, 128.7, 126.3, 126.2, 125.8, 125.1, 123.5, 123.2, 118.5, 118.0, 114.5, 85.5, 77.9, 76.2, 59.8, 59.3, 50.0, 49.7, 48.9, 40.0, 39.7, 38.3, 28.3, 28.1, 27.9, 26.3, 23.3, 22.0, 19.3, 13.9. mass spectrum (MALDI-TOF) 957 (calcd 957), [α]D+48.8° (c1.0, MeOH).

2,4,6-Tri(9-O-cinchonidinyl)pyrimidine (AP-2). 1H. NMR δ 8.85 (d, J=4.8 Hz, 2H), 8.63 (d, J=4.2 Hz, 1H), 8.27 (d, =8.4 Hz, 2H), 8.16 (dd, J=8.4, 0.9 Hz, 2H), 8.08 (d, J=8.4 Hz, 1H), 7.97 (d, J=7.8 Hz, 1H), 7.76 (td, J=7.2, 1.2 Hz, 2H), 7.70 (t, J=8.4 Hz, 1H), 7.65 (td, J=7.2, 0.9 Hz, 2H), 7.55 (t, J=8.4 Hz, 1H), 7.31 (d, J=4.2 Hz, 2H), 6.84 (d, J=4.5 Hz, 1H), 6.50 (d, J=6.0 Hz, 2H), (s, 1H), 5.80 (s, 1H), 5.78-5.63 (m, 3H), 4.97-4.91 (m, 6H), 3.28 (q, 1=9.0, Hz, 2H), 3.14 (m, 1H), 2.95 (dd, J=13.8, 10.2 Hz, 4 II), 2.66 (q, J=6.9, Hz, 2H), 2.50-2.34 (m, 6H), 2.19 (m, 3H), 1.82 (in, 3H), 1.70 (m, 6H), 1.37 (in, 6H); 13C NMR δ 171.1, 162.6, 149.8, 149.7, 148.3, 148.2, 145.3, 145.1, 141.4, 130.3, 128.9, 126.6, 126.5, 125.7, 125.2, 123.6, 123.2, 118.7, 118.1, 114.2, 114.1, 85.4, 77.9, 76.4, 59.9, 59.6, 56.8, 56.6, 42.6, 42.3, 39.7, 39.6, 27.7, 27.54, 27.49, 27.4, 23.8, 22.4.

2,4,6-Tri(9-O-quininyl)pyrimidine (AP-3). UV; 206, 240, 336 nm, 1H NMR δ 8.70 (d, J=4.5 Hz, 2H), 8.52 (d, J=4.5 Hz, 1H), 8.04 (d, J=9.6 Hz, 2H), 7.96 (d, J=9.3 Hz, 1H), 7.38 (d, J=8.1 Hz, 2H), 7.36 (s, 2H), 7.30 (dd, J=9.3, 2.7 Hz, 1H), 7.23 (d, J=4.2 Hz, 2H), 7.12 (s, 1H), 6.85 (d, J=4.5 Hz, 1H), 6.41 (d, =5.7 Hz, 2H), 6.00 (s, 1H), 5.83 (s, 1H), 5.79-5.60 (m, 3H), 4.98-4.88 (iii, 6H), 3.90 (s, (3H), 3.70 (s, 3H), 3.31 (q, =7.2 Hz, 2H), 3.12 (m, 1H), 3.00 (dd, =13.2, 10.2 Hz, 4H), 2.80-2.77 (m, 2H), 2.53-2.44 (m, 6H), 2.23-2.18 (m, 6H). 1.73-1.62 (m, 6H), 1.44 (m, 6H); 13C NMR δ 171.2, 162.9, 157.5, 157.4, 147.2, 147.0, 144.4, 144.2, 143.3, 143.2, 141.4, 131.6, 131.5, 126.4, 125.8, 121.5, 121.4, 118.9, 118.2, 114.2, 101.7, 101.3, 85.6, 78.9, 77.0, 59.2, 58.9, 56.8, 56.6, 55.6, 55.4, 42.6, 42.4, 39.6, 37.7, 27.6, 27.5, 27.3, 23.4, 22.4, 18.9, 13.7, 12.0. Mass spectrum (MALDI-TOF): 1052 (calculated 1047), HPLC: Rt: 22 min, LiChrospher 100 CN column (5 μm), solvent: H2O (0.1% TEA+ 0.1% TFA):CH3CN:55:45, flow rate: injection volume: 5 μL 2,4,6-Tri (9-O-quinidinyl)pyrimidine (AP-4). UV: 200, 240, 336 nm, I1H NMR δ 8.70 (d, J=4.5 Hz, 2H), 8.52 (d, 1=4.2 Hz, 1H), 8.04 (d, J=9.3 Hz, 2H), 7.92 (d, J=9.3 Hz, 1H), 7.36 (dd, J=9.3, 2.7 Hz, 2H), 7.25 (d, J=4.5 Hz, 2H), 7.21 (d, J=2.7 Hz, 1 II), 7.17 (d, J=2.1 Hz, 2H), 6.90 (d, J=4.2 Hz, 1H), 6.84 (s, 1H), 6.37 (d, J=4.2 Hz, 2H), 6.00-5.75 (m, 5H), 5.05-4.88 (m, 6H), 3.82 (s, 6H), 3.52 (s, 3H), 3.22 (q, J=4.5 Hz, 2H), 3.01 (m, 1 II), 2.83-2.65 (m, 12H), 2.24-2.11 (m, 3H), 1.85 (m, 6H), 1.73-1.62 (in 3H), 1.46-1.36 (m, 6 II): 13C NMR δ 171.1, 163.3, 157.4, 157.1, 147.2, 147.1, 144.3, 144.1, 143.1, 143.0, 140.2, 131.6, 131.3, 126.0, 125.6, 121.7, 121.5, 118.5, 118.4, 114.8, 114.5, 101.4, 100.9, 85.8, 79.3, 77.7, 58.8, 58.6, 55.5, 55.3, 50.0, 49.2, 48.8, 37.5, 37.7, 28.3, 28.0, 26.3, 22.2, 21.8, 18.9, 13.7. Mass spectrum (MALDI-TOF): 1049 calcd 1047. HPLC; Rt: 19.3 min, LiChrospher 100 CN column (5 μm), Solvent: H2O (0.1% TFA+0.1% TEA):CH3CN (50:50), flow rate observation wavelength: 200 nm, injection volume 5 μL.

2,4,6-Tri (9-O-dihydrocinchoninyl)pyrimidine (AP-5). 1H NMR δ 8.84 (d, J=4.5 Hz, 2H), 8.61 (d, J=4.5 Hz, 1 II), 8.22 (d, J 8.7 Hz, 2H), 8.16 (d, J=8.7 Hz, 2H), 8.08 (d, J=8.7 Hz, 1. H), 7.97 (d, J=7.8 Hz, 1. H), 7.76 (t, J=7.2 Hz, 2H), 7.69 (t, J=7.5 Hz, 1H), 7.62 (t, J=7.8 Hz, 2H), 7.48 (t, J=7.8 Hz, 1H), 7.28 (d, J=4.2 Hz, 2H), 6.83 (d, J=4.5 Hz, 1H), 6.45 (d, J=6.6 Hz, 2H), 6.12 (d, =4.5 Hz, 1H), 5.76 (d, J=0.6 Hz, 1H), 3.17 (dt, J=6.9, 8.4 Hz, 2H), 2.99 (dt, J=4.8, 9.0 Hz, 1H), 2.60 (q, J=9.0 Hz, 9H), 2.43-2.27 (m, 3H), 1.71-1.64 (m, 6H), 1.43-1.23 (m, 18H), 0.88 (t, =6.9 Hz, 3H), 0.81 (t, J=7.5 Hz, 6H); 13C NMR δ 171.0, 162.6, 149.7, 149.6, 148.2, 148.1, 145.6, 145.2, 130.2, 128.8, 128.7, 126.3, 125.8, 125.1, 123.6, 123.3, 118.7, 118.0, 85.3, 78.1, 76.4, 59.9, 59.4, 50.6, 50.5, 50.1, 49.8, 37.2, 27.1, 25.6, 25.5, 25.0, 24.8, 23.1, 23.0, 21.7, 19.1, 19.0, 13.3, 12.2, 12.0. Mass spectrum (MALDI-TOF): 965.8 calcd. 964.3, HPLC; Rt 16.0 min, LiChrospher 1.00 CN column (5 μm), Solvent: H2O (0.1% TFA+0.1% TEA):CH3CN (40:60), flow rate: 1 ml/min, observation wavelength: 202 nm, injection volume 5 μL.

2,4,6-Tri (9-O-dihydrocinchonidinyl)pyrimidine (AP-6). mp: 147-154° C., IR: 2956, 2870, 1588, 1434, 1389, 1169, 910, 760 cm−1; 1H NMR δ 8.85 (d, J 4.5 Hz, 2H), 8.64 (d, J=4.5 Hz, 1H), 8.28 (d, J=8.1 Hz, 2H), 8.1.6 (d, J=8.4 Hz, 3H), 8.08 (d, J=8.7 Hz, 1H), 7.76 (td, J=8.1, 0.9 Hz, 2H), 7.70 (t, =7.5 Hz, 1H), 7.65 (td, J=6.9, 1.2 Hz, 2H), 7.54 (t, J=9.9 Hz, 1. H), 7.31 (d., J=4.2 Hz, 2H), 6.87 (ci, J=4.8 Hz, 1H), 6.50 (d, J=6.3 Hz, 2H), 6.21 (s, 1H), 5.79 (s, 1H), 3.26 (m, 2H), 3.14 (m, 1H. 2.92 (dd., J=12.9, 9.9 Hz, 2H), 2.66 (m, 2H), 2.37 (m, 2H), 2.35-2.1.9 (m, 3H), 1.85 (m, 6H), 1.41-1.19 (m, 18H), 0.79 (t, J=7.2 Hz, 9H); 13C NMR δ 171.1, 162.6, 149.8, 149.7, 148.3, 148.2, 145.3, 145.2, 140.7, 130.2, 128.9, 126.5, 126.4, 125.7, 125.2, 123.6, 123.3, 118.7, 118.2, 11.4.3, 85.3, 78.0, 59.8, 59.5, 58.4, 58.2, 42.6, 42.4, 37.7, 37.2, 28.2, 28.0, 27.5, 27.4, 25.3, 25.2, 23.5, 22.3, 12.3, 12.0._\-lass (MALDI-TOF) 964.9 (M+2) (Coded 962.5); HPLC: Rt: 16.1 mi, Normal Phase LiChrospher 100 CN column (5 μm), Solvent: H2O (0.1% TFA+0.1% TEA): CH3CN (50:50), flow rate: 1 ml/min, observation wavelength: 228 nm, 5 μL injection volume.

2,4,6-Tri (9-O-dihydroquininyl)pyrimidine (AP-7). 1H NMR δ 8.84 (d, J=4.5 Hz, 2H), 8.61 (d, J=4.5 Hz, 1H), 8.22 (d, J=8.7 Hz, 2H), 8.16 (d., J=8.7 Hz, 2H), 8.08 (d, J=8.7 Hz, 1H), 7.97 (d, J=7.8 Hz, 1H), 7.76 (t, J=7.2 Hz, 2H), 7.69 (t, J=7.5 Hz, 1H), 7.62 (t, J=7.8 Hz, 2H), 7.48 (t, J=7.8 Hz, 1H), 7.28 (d, J=4.2 Hz, 2H), 6.83 (d, J=4.5 Hz, 1H), 6.45 (d, J=6.6 Hz, 2H), 6.12 (d, J=4.5 Hz, 1H), 5.76 (d, J=0.6 Hz, 1H), 3.9 (s, 9H), 3.17 (q, J=8.4, 6.9 Hz, 2H), 2.99 (q, J=9.0, 4.8 Hz, 1H), 2.60 (q, =9.3, 9.0 Hz, 9H), 2.43-2.27 (m, 3H), 1.71-1.64 (m, 6H), 1.43-1.23 (m, 18H), 0.88 (t, J=6.9 Hz, 3H), 0.81 (t, J=7.5 Hz, 6H); 13C NMR δ 171.1, 162.6, 158.0, 157.8, 147.3, 146.9, 144.4, 144.2, 131.6, 131.4, 126.1, 125.7, 122.3, 121.7, 119.0, 118.1, 101.6, 101.0, 85.9, 58.8, 58.5, 58.0, 56.2, 43.2, 42.7, 36.7, 36.3, 27.4, 27.2, 25.0, 22.3, 1.1.9, 11.8.

2,4,6-Tri (9-O-dihydroquinidinyl)pyrimidine (AP-8). mp 113-120° C., IR: 2934, 2871, 1588, 1433, 1377, 1170, 912, 733 cm−1; 1H NMR δ 8.69 (d., J=4.2 Hz, 2H), 8.51 (d, J 4.5 Hz, 1H), 8.03 (d, J=9.6 Hz, 2H), 7.92 (d, J=9.3 Hz, 1H), 7.36 (dd., J=9.3, 2.7 Hz, 3H), 7.23 (d, J=4.2 Hz, 2H), 7.21 (s, 2H), 6.88 (d, J=4.5 Hz, 2H), 6.34 (d, J=4.5 Hz, 2H), 5.84 (s, 2H), 3.83 (s, 6H), 3.53 (s, 3H), 3.20 (q, J=5.1 Hz, 2H), 3.00 (q. J=4.2 Hz, 1H), 2.82-2.54 (in, 12H), 1.97-1.16 (m, 24H), 0.87 (t, J=6.9 Hz, 6H), 0.79 (t, J=6.9 Hz, 3H); 13C NMR δ 171.2, 163.3, 157.4, 157.1, 147.2, 147.0, 144.4, 144.1, 143.3, 143.2, 131.5, 131.2, 126.1, 125.7, 121.7, 121.5, 118.6, 118.4, 101.5, 101.0, 85.5, 79.4, 77.8, 59.0, 58.8, 55.8, 55.5, 55.3, 50.7, 50.6, 50.3, 50.2, 37.2, 27.1, 27.0, 25.8, 25.2, 24.6, 22.1, 21.7, 12.1, 12.0. Mass (MALDI-TOF) 1054 (M+1), Calcd. 1053, HPLC: Rt: 19.3 min, Normal Phase LiChrospher 100 CN Column (5 μm), Solvent: H2O (0.1% TEA+ 0.1% TEA):CH3CN 50:50, flow rate hill/min., observation wavelength: 228 nm, 5 μL injection volume.

Scheme 1a

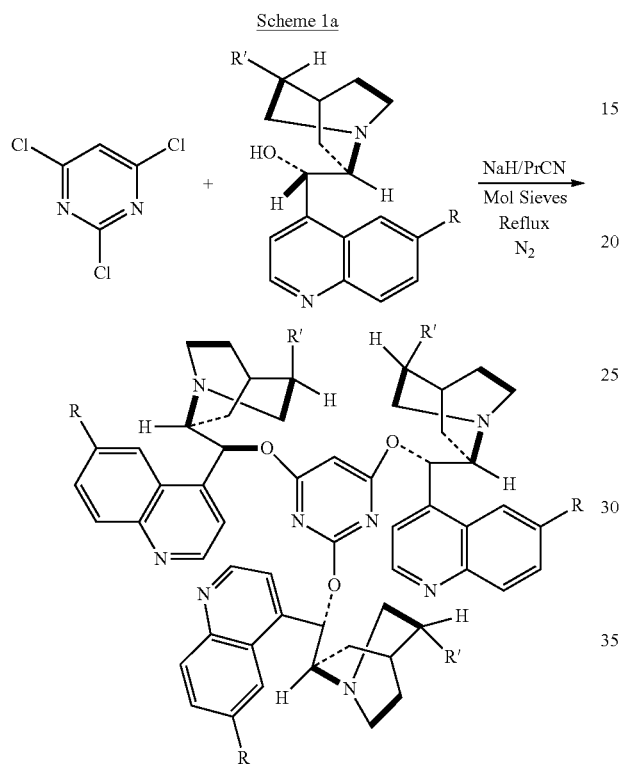

| R | R' | Cinchona alkaloid | Product |
|---|---|---|---|
| H | CH=CH$_2$ | Cinchonine | AP-1 |
| OCH$_3$ | CH=CH$_2$ | Quinicline | AP-4 |
| H | CH$_2$CH$_3$ | Hydro cinchonine | AP-5 |
| OCH$_3$ | CH$_2$CH$_3$ | Hydro Quinicline | AP-8 |

Scheme 1b

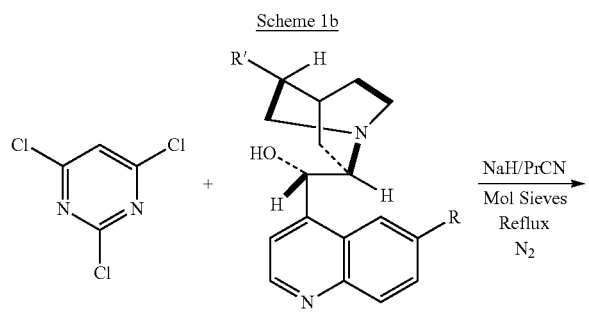

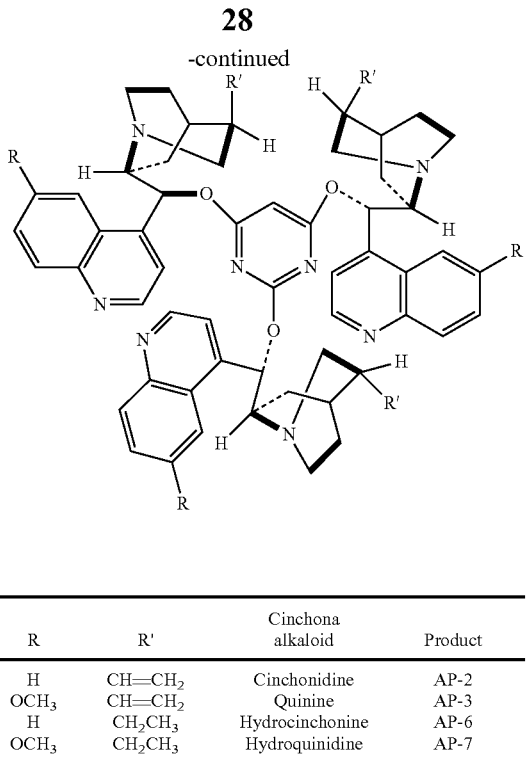

| R | R' | Cinchona alkaloid | Product |
|---|---|---|---|
| H | CH=CH$_2$ | Cinchonidine | AP-2 |
| OCH$_3$ | CH=CH$_2$ | Quinine | AP-3 |
| H | CH$_2$CH$_3$ | Hydrocinchonine | AP-6 |
| OCH$_3$ | CH$_2$CH$_3$ | Hydroquinidine | AP-7 |

Example 2. In Vitro Anti-Cancer Activity of the Novel Cinchona Alkaloid-Trisubstituted Pyrimidines Methods Cell Lines Human B-lineage acute lymphoblastic leukemia (ALL) cell line NALM-6 and T-lineage ALL/lymphoma cell line MOLT-3 were obtained from American Type Culture Collection (Manassas, Va.). Cell lines were propagated in RPMI 1640 supplemented with 10% FCS, 4 mM glutamine, 100 units/ml penicillin G, and 100 mg/ml streptomycin sulfate. All tissue culture reagents were obtained from Life Technologies Inc. (Life Technologies, Inc., Gaithersburg, Md.). Cell lines were cultivated for a minimum of two passages after thawing prior to experimentation.

MTT Assays

The cytotoxicity of the compounds were tested against human ALL cell lines using MTT assays (Roche Molecular Biochemicals, Indianapolis, Ind.), as described previously R. K. Narla et al., 1998, Clin Cancer Res 4:1405-14). Briefly, exponentially growing tumor cells were seeded into a 96-well plate at a density of $4 \times 10^4$ cells/well and incubated in medium containing the cinchona alkaloid compounds at concentrations ranging from 0.7 to 100 μM for 48 h at 37° C. in a humidified 5% CO$_2$ atmosphere. To each well, 10 μL of MTT (final concentration, 0.5 mg/ml) was added, and the plates were incubated at 37° C. for 4 h to allow MTT to form formazan crystals by reacting with metabolically active cells. The formazan crystals were solubilized overnight at 37° C. in a solution containing 10% SDS and 0.01 M HCl. The absorbance of each well was measured in a microplate reader (Labsystems) at 540 nm and a reference wavelength of 690 nm. To translate the $A_{540}$ values into the number of live cells in each well, the $A_{540}$ values were compared to those on standard $A_{540}$ versus cell number curves generated for each cell line. The percentage of survival was calculated using the formula: % survival=[Live cell number (test)/Live cell number (control)]×100. The $IC_{50}$ values were calculated by nonlinear regression analysis using the graphed Prism Software version 2.0 (GraphPad Software, Inc., San Diego, Calif.).

Results

The novel cinchona alkaloids AP-1-AP-8 exhibited potent cytotoxicity against leukemia cells lines with low micromolar $IC_{50}$ values (Mean±SE against NALM-6: 4.5±1.1 µM; Mean±SE against MOLT-3: 5.7±1.1 µM) (Table 1).

Example 2. Novel Cinchona Alkaloid AP-5 Causes Apoptosis in Chemotherapy-Resistant Cancer Cells from Leukemia Patients Methods The ability of anti-cancer drugs to cause apoptosis of leukemia and lymphoma cells derived from patients was shown to be predictive of the effectiveness of the same drugs in clinical settings (F. M. Uckun, et al., 2011, British Journal of Haematology, 153:741-752). We examined the ability AP-5 to cause apoptotic death in freshly obtained primary cancer cells from Ficoll-Hypaque separated, highly enriched populations of primary leukemia/lymphoma cells isolated from bone marrow (BM, N=13) or peripheral blood (PB, N=13) specimens of 26 patients with hematological malignancies, 3 patients with rare forms of leukemia (one each with prolymphocytic leukemia [PLL], plasma cell leukemia [PCL], large granular cell leukemia [LGL]), one patient with chronic myeloid leukemia in blast crisis (CML-BC), including 8 patients with chronic lymphocytic leukemia (CLL)/well differentiated lymphocytic lymphoma (WDLL), one patient with acute myeloid leukemia (AML), 11 patients with B-lineage acute lymphoblastic leukemia (ALL) and 2 patients with T-lineage ALL (FIG. 1). Cells were treated with standard chemotherapeutic agents at various concentrations provided in RPMI-1640 medium supplemented with 10% fetal bovine serum (FBS) and incubated at 37° C. for 24 hr. Dexamethasone (DEQ.) was used. at 50 µg/ml, Adriamycin (ADR) at 10 µg/ml, vincristine (VCR), gemcitabine (GEM), fludarabine (FLU), methotrexate (MTX), etoposide (ETO), cytarabine (ARA-C) and cladribine (2-CDA) at 25 µg/ml. The cells were washed with serum-free RPMI-1640 medium and then processed for apoptosis assays. All patient specimens were used under the exemption category (45 CFR Part 46.101; Category #4: Existing Data, Records Review, and Secondary Use of Pathologic Specimens) following the guidelines of the local Institutional Committee on the Use of Human Subjects in Research for secondary use of pathological or surgical tissue in accordance with US Department of Health and Human Services guidelines.

TABLE 1

In Vitro Cytotoxicity of Cinchona Alkaloid-Trisubstituted Pyrimidines Against Human Leukemia Cells as Measured by MTT Assays

| Compound | $IC_{50}$ against NALM-6 (µM) | $IC_{50}$ against MOLT-3 (µM) |
| --- | --- | --- |
| AP-1 | 3.4 | 6.7 |
| AP-2 | 11.4 | 5.8 |
| AP-3 | 3.6 | 4.5 |
| AP-4 | 2.8 | 3.1 |
| AP-5 | 1.7 | N.D |
| AP-6 | 6.0 | 11.4 |
| AP-7 | 3.3 | 3.5 |
| AP-8 | 3.7 | 5.2 |
| Average (Mean ± SE) | 4.5 ± 1.1 | 5.7 ± 1.1 |

Apoptotic death was monitored using multiparameter flow cytometry, as previously reported (F. M. Uckun et at, 2006, Brit Journal of Hematol. 135:500-8; F. M. Uckun et al., 2011, Brit Journal of hematol. 153:741-52; F. M. Uckun et al., 2015, J. Clin. Invest. 125:1006-18). Exposure of phosphatidylserine to the outer leaflet of the leukemic cell membrane was measured using fluorescein isothiocyanate (FITC)-conjugated annexin V, the natural ligand of phosphatidylserine (R&D Systems, Minneapolis, Minn., USA). Cells were labelled with annexin V-FITC using the Annexin V-FITC apoptosis detection kit (R&D Systems, Catolog no. TA-5532) according to the manufacturer's recommendations. Cells were co-stained with phycoerythrin (PE)-labelled anti-CD19 (for B-lineage ALL and CLL/WDLL), anti-CD7 (for T-lineage ALL, PLL and LGL), anti-CD33 (for AML), anti-CD38 (for PCL) or anti-CD34 (for CML-BC) monoclonal antibodies for 30 min in the dark at a dilution of 1:200 before staining with Annexin V-FITC. The labelled cells were analyzed using a FACS Vantage flow cytometer (Becton Dickinson, Mountain view, CA, USA). One-sample T-tests were performed to assess the significance of the % apoptosis using AP-5 versus % apoptosis for combined values from the other drugs for each patient. Two-sample T-tests with correction for unequal variance were performed. comparing the mean % apoptosis for AP-5 versus each of the nine standard chemotherapy drugs, and the mean % apoptosis for all the drugs combined for all patients versus AP-5 for all patients.

Results

Figure 2:
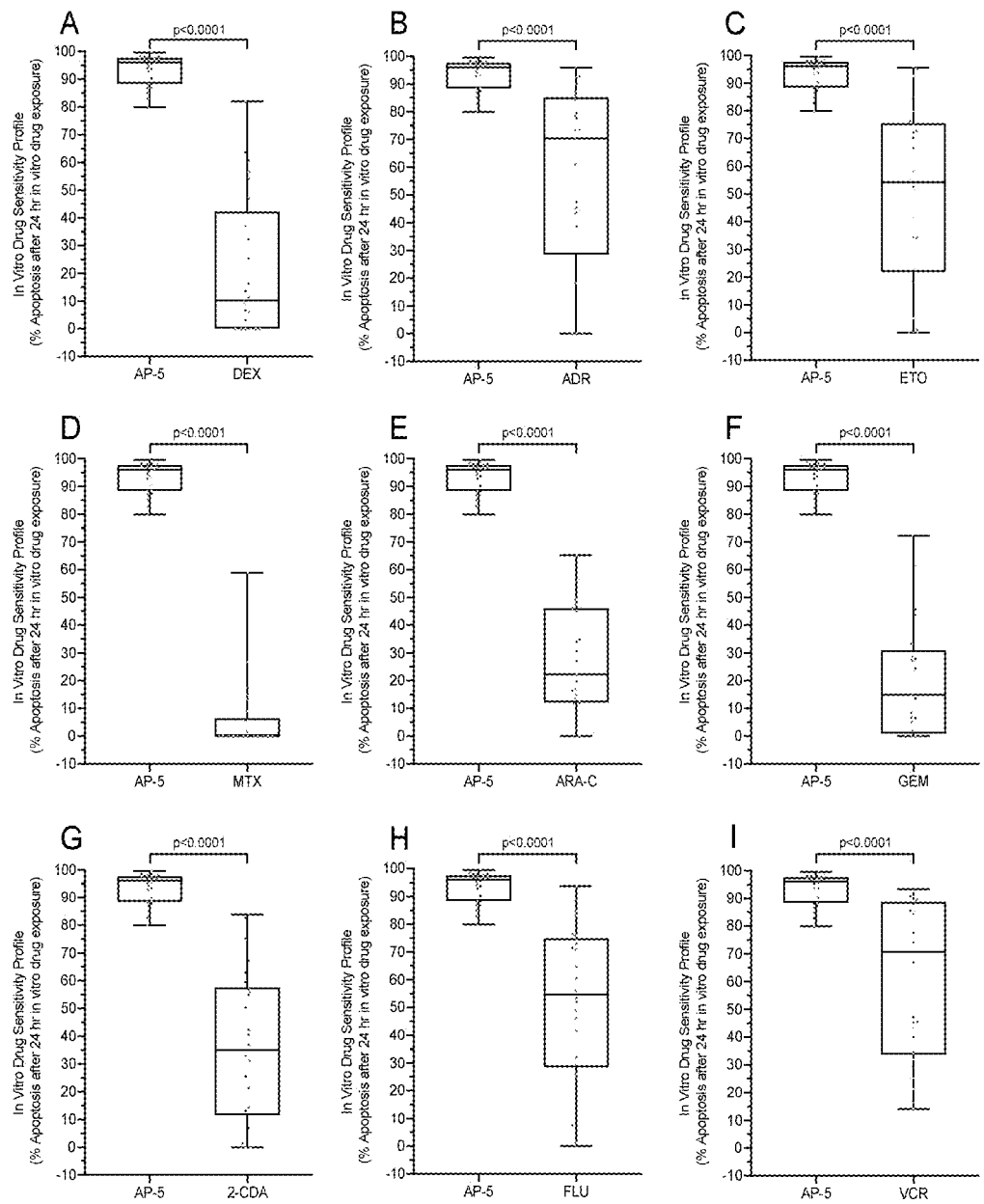
FIG. 2. This figure demonstrates that AP-5 is more potent than the standard leukemia drugs tested side by side. The depicted Whisker plots represent the median and values (Min to Max. all data points are shown) for % apoptosis in primary leukemia cells from 26 patients induced by AP-5 versus 9 different chemotherapy drugs. Statistical significance of the observed differences in the magnitude of apoptosis is shown by the depicted superscripts above the plots were computed using the independent samples T-test (**** $p<0.0001$).
Figure 3:
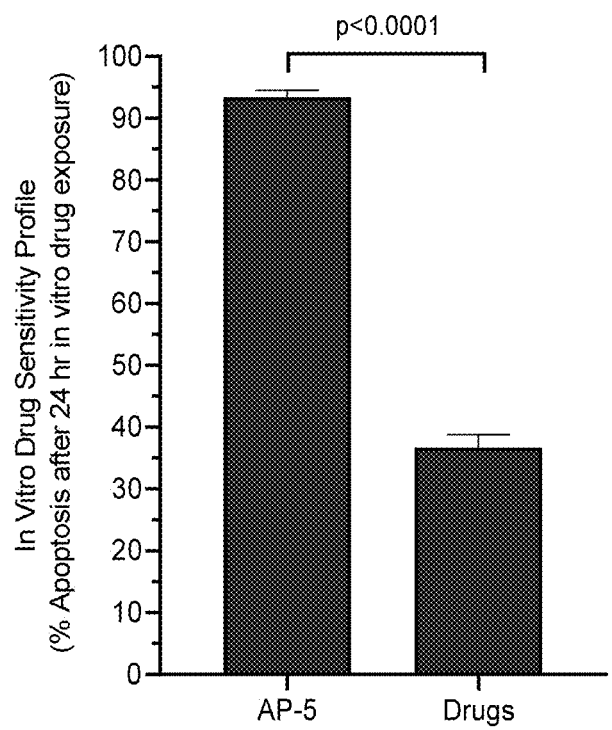
FIG. 3. This figure compares the potency of AP-5 vs. standard anti-leukemia drugs. The depicted bars represent the mean and standard error values for the % Apoptosis in primary leukemia cells from 26 patients achieved after 24 hour in vitro exposure to AP-5 (cumulative number of data points: 26) or any of the 9 drugs tested (cumulative number of data points: 228). Statistical significance between the two groups (AP-5 versus combined values from the other drugs) is shown by the depicted superscripts above the plots were computed using the independent samples T-test (**** $p<0.0001$).

AP-5 induced apoptosis in 79.9-99.6% of primary leukemia/lymphoma cells (Mean±SE=93.5±1.1%) and it was substantially more potent than any of the 9 standard chemotherapy drugs tested side by side (FIG. 1, FIG. 2). Whereas the median percentage of apoptosis was 32% for chemotherapy drugs, it was 96.1% for AP-5 (FIG. 3). The depicted bars in FIG. 1 represent the mean and standard error values for the % Apoptosis in primary leukemia/lymphoma cells from 26 patients achieved after 24 hour in vitro exposure to each of the drugs tested. Statistical significance between the two groups is shown by the depicted superscripts above the plots were computed using the independent samples T-test (**** $p<0.0001$).

FIG. 2 demonstrates that AP-5 is more potent than the other anti-leukemia drugs tested side by side. The depicted Whisker plots represent the median and values (Min to Max. all data points are shown) for % apoptosis in primary leukemia/lymphoma cells from 26 patients induced by AP-5 versus 9 different chemotherapy drugs. Statistical significance of the observed differences in the magnitude of apoptosis is shown by the depicted superscripts above the plots were computed using the independent samples T-test (** $p<0.0001$). FIG. 3 compares the potency of AP-5 vs. standard anti-leukemia drugs. The depicted bars represent the mean and standard error values for the % Apoptosis in primary leukemia cells from 26 patients achieved after 24 hour in vitro exposure to AP-5 (cumulative number of data points: 26) or any of the 9 drugs tested (cumulative number of data points: 228). Statistical significance between the two groups (AP-5 versus combined values from the other drugs) is shown by the depicted superscripts above the plots were computed using the independent samples T-test (** $p<0.0001$).

Example 3. In Vitro Potency of Novel Cinchona Alkaloid AP-5 Against Leukemia-Initiating ALL Xenograft Cells ("Leukemia Stem Cells")

Methods

Patient derived xenograft mouse models have predictive value for clinical responses (Xu C, Li X, Liu P, Li M and Luo F: Patient-derived xenograft mouse models: A high fidelity tool for individualized medicine (Review). Oncol Lett 17: 3-10, 2019). Xenograft clones isolated from spleens of NOD/SCID mice that developed overt leukemia after inoculation with primary leukemia cells from a B-lineage ALL patient were treated for 24 hours at 37° C. with one of two concentrations of AP-5 (1 µM or 3 µM in phosphate buffered saline [PBS] with 2% DMSO) or vehicle (PBS with 2% DMSO) and then reinjected into NOD/SCID mice (Control group: 9 mice; AP-5 groups: 8 mice per concentration level). Mice were monitored for signs of leukemia, and all mice in a given experiment were sacrificed when any mouse developed morbidity. The animal research in mice was conducted according to approved local IACUC protocols. All animal care procedures conformed to the *Guide for the Care and Use of Laboratory Animals* (National Research Council, National Academy Press, Washington D.C., USA. Revised 1996). Leukemia cells isolated from deidentified patient specimens were used in the described experiments. The secondary use of leukemia cells for subsequent laboratory studies did not meet the definition of human subject research per 45 CFR 46.102 (d and f), since it did not include identifiable private information, and the corresponding research protocol was approved by local IRB.

Results

Figure 4:
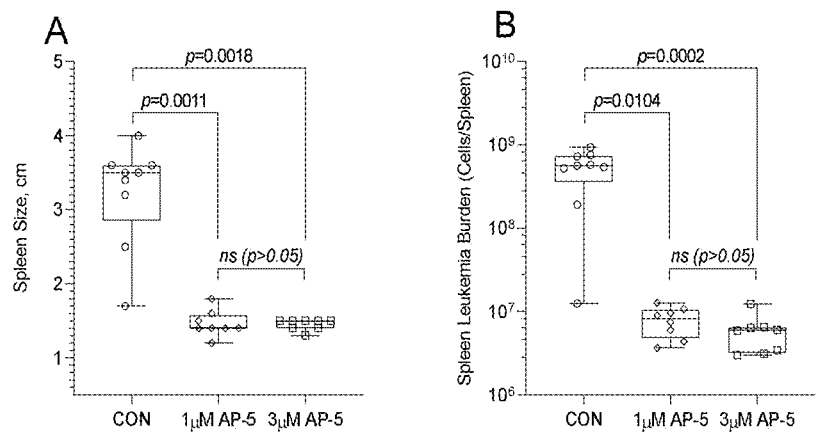
FIG. 4 illustrates that AP-5 abrogates the ability of leukemia-initiating ALL xenograft cells to cause leukemia in NOD/SCID mice. The depicted Whisker plots represent the median and values (Min to Max. Shown all points) for spleen size (Panel A), and spleen leukemia burden (Panel B). Kruskall Wallis and Dunn's multiple comparisons test were used for comparing the results among different groups ($p<0.05$). Statistical significance between groups is shown by the depicted p-values. Also depicted as Panel C is a descriptive data summary.

Eight of the 9 control mice challenged with vehicle-treated xenograft cells developed leukemia between 81 and 85 days. All remaining mice were also sacrificed at 85 days. The spleen size and spleen leukemia burden were compared using previously published procedures (F. M. Uckun et al., 2015, J Clin Invest. 125:1006-18). Necropsy revealed massive splenomegaly, measuring 2.5-4.0 cm at the time of death in 8 of 9 control mice inoculated with vehicle-treated xenograft cells. The nucleated spleen cell count in these leukemic mice ranged from $192\times10^6$ to $940\times10^6$ (median: $576\times10^6$). The mean±SE values for all 9 control mice was 3.2±0.2 cm for the spleen size and $536.39\pm94.45\times10^6$ cells for the spleen leukemia burden (FIG. 4). By comparison, the spleens of mice inoculated with xenograft cells treated with AP-5 at a concentration of 1 µM (mean±SE=1.5±0.1 cm) (P=0.0011) or 3 µM (mean±SE=1.5±0.0 cm) (P=0.0018) were much smaller and contained substantially fewer cells (1 µM group: $7.95\pm1.11\times10^6$ cells/P=0.0104; 3 µM group: $5.84\pm1.07\times10^6$ cells/P=0.00002). Thus, at a low micromolar concentration, AP-5—most likely via apoptotic destruction—was capable of abrogating the ability of the putative leukemic stem cell subpopulation of BPL xenograft cells to initiate leukemia in immunodeficient NOD/SCID mice. FIG. 4 illustrates that AP-5 abrogates the ability of leukemia-initiating ALL xenograft cells to cause leukemia in NOD/SCID mice. The depicted Whisker plots in FIG. 4 represent the median and values (Min to Max. all data points are shown) for spleen size (A), and spleen leukemia burden (B). Kruskall Wallis and Dunn's multiple comparisons test were used for comparing the results among different groups (p<0.05). Statistical significance between groups is shown by the depicted p-values.

Example 4. Novel Cinchona Alkaloid AP-5 Causes Apoptotic Destruction of Human Solid Tumor Cell Lines Methods Cell lines. BT-20 (ATCC HTB-19), a triple negative breast cancer cell line, PC-3 (ATCC CRL-1435) a CRPC cell line (small cell endocrine carcinoma) derived from a Stage IV prostate cancer patient with bone metastases were obtained from American Type Culture Collection (ATCC) (Manassas, Va.). Cancer cell lines were maintained in RPMI 1640 supplemented with 10% fetal bovine serum. For sub-culturing, medium was removed from the flasks containing a confluent layer of cells, and fresh 0.25% trypsin was added for 1-2 min. Trypsin was removed, and cultures were incubated for 5-10 min at 37° C. until cells detached. Fresh medium was then added, and cells were aspirated and dispensed into new flasks.

Immuno-cytochemistry and Confocal Laser Scanning Microscopy. Cells were treated with 100 nM AP-5 in vehicle (PBS with 2% DMSO) or vehicle in culture medium for 48 hours. Tubulin expression was examined by immunofluorescence using a monoclonal antibody against α-tubulin (Sigma Chemical Co.) at a dilution of 1:1000 and an anti-mouse IgG conjugated to FITC (green florescence). Cells were washed in PBS and counterstained with the DNA-specific dye TOTO-3 (blue fluorescence) (Molecular Probes Inc., Eugene, Oreg.) for 10 min at a dilution of 1:1000. Cells were washed again with PBS, and the coverslips were mounted with Vectashield (Vector Laboratories). Cells were examined by laser scanning confocal microscopy using a Bio-Rad MRC-1024 Laser Scanning Confocal Microscope equipped with a Kr/Ar laser (Bio-Rad, Hercules, Calif., USA) mounted on a Nikon Eclipse E800 upright microscope with high numerical aperture objectives (Nikon, Melville, N.Y., USA), as described (F. M. Uckun, et al., 2010, Proc. Natl. Acad. Sci. USA 107: 2902-7; F. M. Uckun, et al., 2010, British Journal of Haematology, 149: 508-17; F. M. Uckun, et al., 2013, Blood. 121:4348-54).

Results

Figure 5:
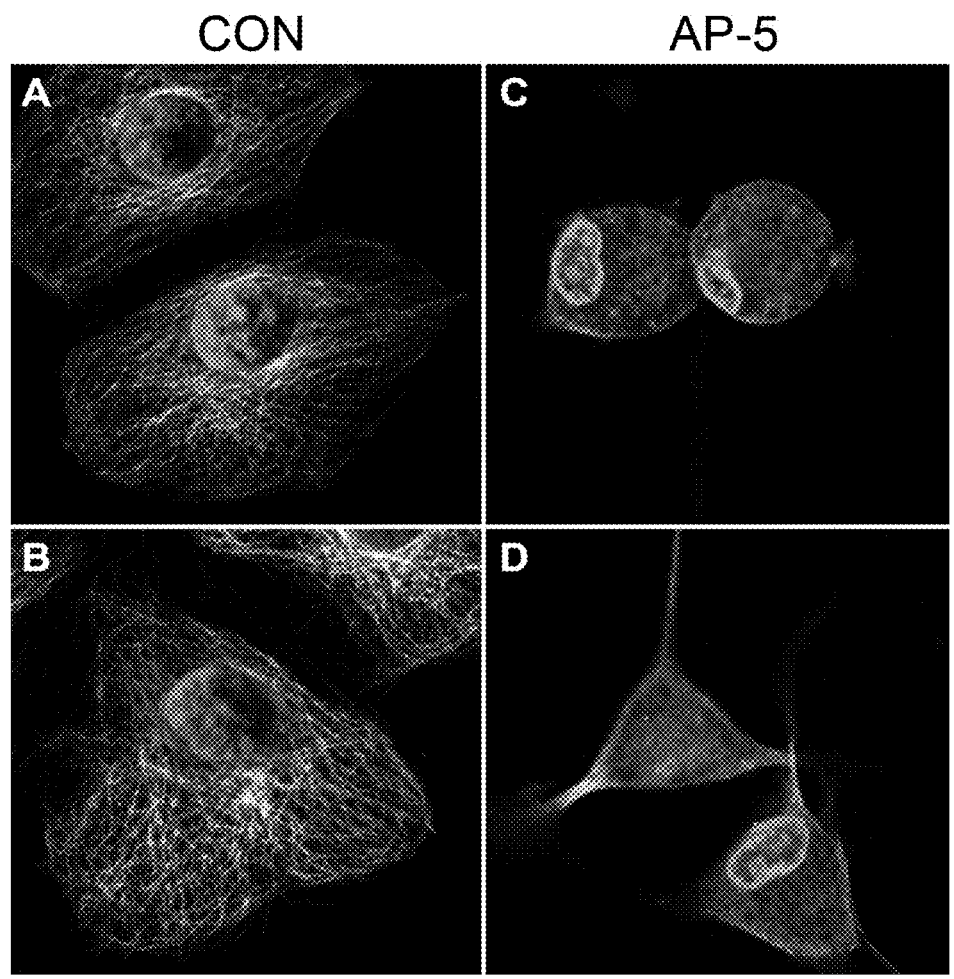
FIG. 5 illustrates the cytotoxic activity of AP-5 Against the TNBC Cell Line, BT-20. Cells were treated with 100 nM AP-5 or vehicle alone (CON) in FBS-supplemented DMEM for 48 hours and then examined by confocal imaging. Whereas vehicle-treated control (CON) cells maintained their viability, virtually all of the BT-20 cells treated with AP-5 showed signs of advanced apoptosis, including shrinkage and fragmentation of the nuclei, loss of cytoplasmic, and nuclear integrity and loss of the tubulin organization in the cytoplasm and cell membrane.
Figure 6:
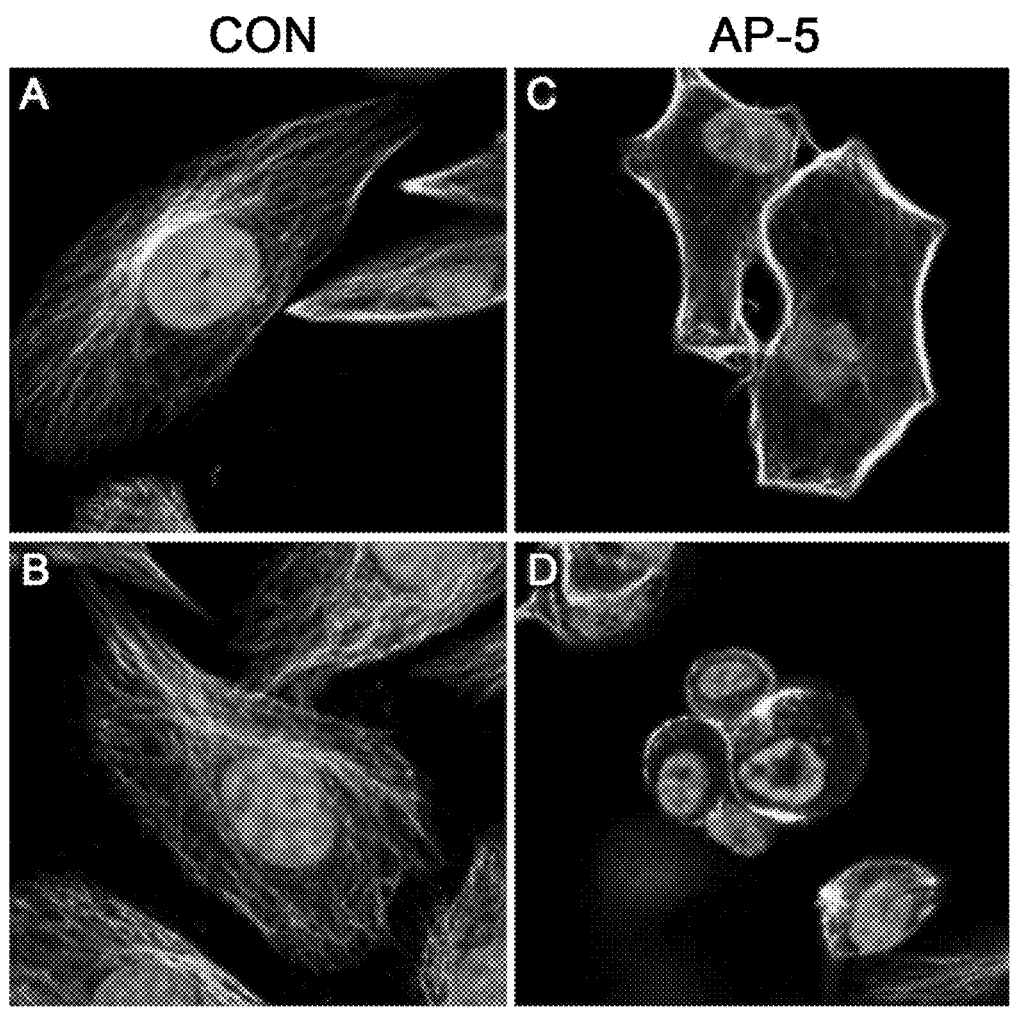
FIG. 6 illustrates the cytotoxic activity of AP-5 Against the CRPC cell line PC-3. Cells were treated with 100 nM AP-5 or vehicle alone (CON) in FBS-supplemented DMEM for 48 hours and then examined by confocal imaging. Whereas vehicle-treated control (CON) cells maintained their viability, virtually all of the PC-3 cells treated with AP-5 showed signs of advanced apoptosis, including shrinkage and fragmentation of the nuclei, loss of cytoplasmic, and nuclear integrity and loss of the tubulin organization in the cytoplasm and cell membrane.

We evaluated the cytotoxic activity of AP-5 against BT-20 and PC-3 cells using confocal laser scanning microscopy. FIG. 5 and FIG. 6 depict the confocal images of BT-20 and PC-3 cells, respectively, after 48 hours of culture following treatment with 100 nM AP-5 or vehicle alone. Whereas vehicle-treated control (CON) cells maintained their viability, virtually all of the BT-20 or PC-3 cells treated with AP-5 showed signs of advanced apoptosis, including shrinkage and fragmentation of the nuclei, loss of cytoplasmic, and nuclear integrity and loss of the tubulin organization in the cytoplasm and cell membrane. Specifically, FIG. 5 shows the cytotoxic activity of AP-5 Against the TNBC Cell Line, BT-20. FIG. 6 illustrates the cytotoxic activity of AP-5 Against the CRPC cell line PC-3.

Example 5. Novel Cinchona Alkaloid AP-1 Exhibits Significant In Vivo Antitumor Activity and Delays Tumor Progression in a SCID Mouse Xenograft Model of Human Glioblastoma Multiforme (GBM)

Methods

Cell Lines. Human brain tumor cell line U87 (ATCC HTB-14) was obtained from American Type Culture Collection (Rockville, Md.) and maintained as a continuous cell line in DMEM supplemented with 10% fetal calf serum (FCS), 4 mm glutamine, 100 units/ml penicillin G, and 100 mg/ml streptomycin sulfate. All of the tissue culture reagents were obtained from Life Technologies, Inc. Inc. (Gaithersburg, Md.).

Mice. Female CB.17 SCID mice were obtained from Taconic (Germantown, N.Y.) and housed in a specific-pathogen-free room located in a secure indoor facility with controlled temperature, humidity, and noise levels. Mice were housed in micro-isolator cages and fed with autoclaved rodent chow. Water was also autoclaved and supplemented with trimethoprim/sulfomethoxazol 3 days a week. The animal protocol used in this study was approved by the local Institutional Animal Care and Use Committee (IACUC), and all of the animal care procedures conformed to the Guide for the Care and Use of Laboratory Animals (National Research Council, National Academy Press, Washington D.C. 1996).

SCID Mouse Xenograft Model of Human Glioblastoma Multiforme (GBM). The predictive value of the mouse xenograft models for clinical effectiveness of anti-cancer drugs has been confirmed for several drugs (Richmond A, Su. Y. Mouse xenograft models vs GEM models for human cancer therapeutics. *Dis Model Mech.* 2008; 1(2-3):78-82. doi:10.1242/dmm.000976). CB.17 SCID mice (8 wk. old, female) were inoculated subcutaneously with $1 \times 10^6$ U87 human GBM cells ($1 \times 10^6$/inoculum, volume: 200 µL) in the right hind leg, as described (R. K. Narla et al., 2001, Clin Cancer Res. 7:2124-33). Mice were treated daily with intraperitoneal injections of vehicle (50 µL DMSO) or AP-1 (125 µg~5 mg/kg/day in 50 µL DMSO) according to a 5 days on 2 days off schedule for 4 consecutive weeks. Tumor growth was determined by the measurement of visible tumors with a caliper in three dimensions three days a week and expressed as tumor volume in cubic millimeters ($mm^3$). Tumor volumes were calculated using the formula for the volume of a prolate spheroid, V=4/3×3.14×length/2×width/2×depth/2.

Results

Figure 7:
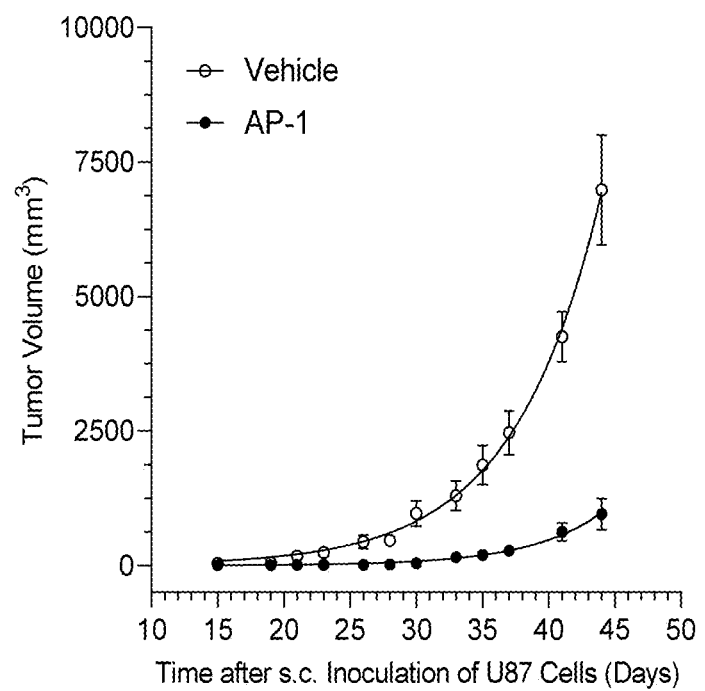
FIG. 7 demonstrates that AP-1 exhibits significant in vivo antitumor activity and delays tumor progression in a CB.17 SCID mouse xenograft model of human glioblastoma multiforme (GBM). Depicted are the tumor growth curves for vehicle-treated control mice (N=9) and AP-1 treated test mice (N=10). The depicted points represent the mean and standard error for the tumor volume measured in tumors from all mice in each group. Tumor growth curves were statistically created using the exponential growth equation in the nonlinear regression method. P-value [AP-1 vs. Vehicle] <0.0001.

Vehicle treated control CB.17 SCID mice (N=9) developed rapidly growing tumors after s.c. inoculation of $1 \times 10^6$ U87 human GBM cells. AP-1 significantly slowed down the tumor progression when administered i.p. in single daily injections (5 mg/kg/dose) given 5 days per week for 4 weeks beginning the day after s.c. inoculation of the tumor cells (FIG. 7). FIG. 7 shows the tumor growth curves for vehicle-treated control mice (N=9) and AP-1 treated test mice (N=10). The depicted points represent the mean and standard error for the tumor volume measured in tumors from all mice in each group. Tumor growth curves were statistically created using the exponential growth equation in the non-linear regression method. P-value [AP-1 vs. Vehicle] <0.0001.

Figure 8:
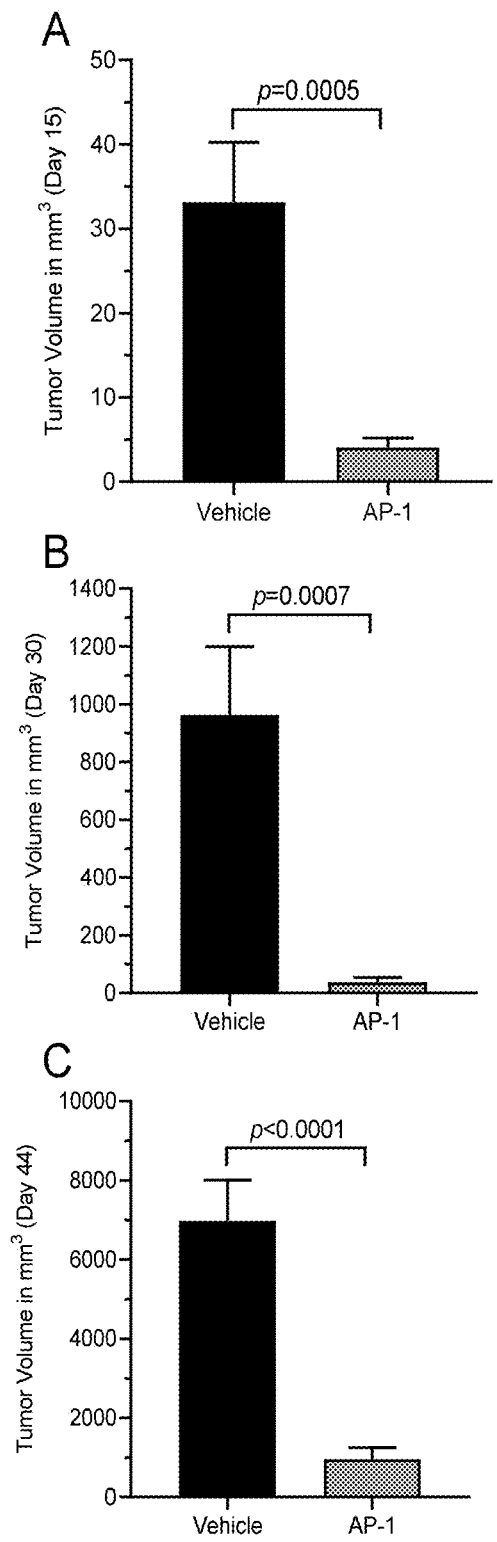
FIG. 8 further illustrates that AP-1 exhibits significant in vivo antitumor activity and delays tumor progression in a CB.17 SCID mouse xenograft model of human glioblastoma multiforme (GBM). The depicted bars represent the mean and standard error for the tumor volume on day 15 (Panel A), day 30 (Panel B), and day 44 (Panel C). Statistical significance between the two groups is shown by the depicted p-values above the plots were computed using independent samples T-test ($p<0.05$).

The depicted bars in FIG. 8 represent the mean and standard error for the tumor volume on day 15 (A), day 30 (B), and day 44 (C). Statistical significance between the two groups is shown by the depicted p-values above the plots were computed using independent samples T-tests (p<0.05).

Tumor volumes in AP-1 treated mice remained substantially smaller than the tumor volumes in vehicle treated control mice at each of the time points examined. At 15 days after the inoculation of tumor cells, the average size of the U87 tumor xenografts in vehicle-treated control SCID mice was 33.1±7.1 $mm^3$, whereas the average size of the U87 tumors in AP-1-treated SCID mice was only 4.1±1.1 $mm^3$ (P=0.0005) (FIG. 8A). Similarly, the average size of U87 tumors in vehicle-treated control SCID mice at 30 days after tumor cell inoculation was 963.3±235.8 $mm^3$, whereas at that time the average size of U87 tumors in AP-1-treated SCID mice was 37.8±16.2 (P=0.0007) (FIG. 8B). On day 44, the tumor sizes were 6982.5±1022.0 $mm^3$ in vehicle-treated control mice and 956.0±291.3 $mm^3$ in AP-1 treated mice (P<0.0001) (FIG. 8C).

Example 6

Novel Cinchona Alkaloid AP-1 Exhibits Significant In Vivo Antitumor Activity and Delays Tumor Progression in a SCID Mouse Xenograft Model of Human Malignant Melanoma.

Methods

Cell Lines. Human melanoma cell line M24-MET (ATCC CRL-12270) was obtained from American Type Culture Collection (Rockville, Md.) and maintained as a continuous cell line in DMEM supplemented with 10% fetal calf serum (FCS), 4 mm glutamine, 100 units/ml penicillin G, and 100 mg/ml streptomycin sulfate. All of the tissue culture reagents were obtained from Life Technologies, Inc. Inc. (Gaithersburg, Md.).

Mice. Female CB.17 SCID mice were obtained from Taconic (Germantown, N.Y.) and housed in a specific-pathogen-free room located in a secure indoor facility with controlled temperature, humidity, and noise levels. Mice were housed in micro-isolator cages and fed with autoclaved rodent chow. Water was also autoclaved and supplemented with trimethoprim/sulfamethoxazol 3 days a week. The animal protocol used in this study was approved by the local Institutional Animal Care and Use Committee (IACUC), and all of the animal care procedures conformed to the Guide for the Care and Use of Laboratory Animals (National Research Council, National Academy Press, Washington D.C. 1996).

SCID Mouse Model of Human Malignant Melanoma. The predictive value of the mouse xenograft models for clinical effectiveness of anti-cancer drugs has been confirmed for several drugs (Richmond A, Su Y. Mouse xenograft models vs GEM models for human cancer therapeutics. *Dis Model Mech.* 2008; 1(2-3):78-82. 0.000976). CB.17 SCID mice (8 wk. old, female) were inoculated subcutaneously with $1 \times 10^6$ M24-MET human melanoma cells ($1 \times 10^6$/inoculum, volume: 200 µL) in the right flank. Mice were treated twice daily with intraperitoneal injections of vehicle (50 µL DMSO) (N=9) or AP-1 (125 µg~5 mg/kg in 50 µL DMSO) (N=5) according to a 5 days on 2 days off schedule. Treatments were initiated 7 days after inoculation of M24-MET cells. The size of subcutaneous tumors were measured on day 14 and day 16 to evaluate the ability of AP-1 to inhibit tumor growth in this SCID mouse xenograft model of melanoma. Tumor volumes were calculated using the formula for the volume of a prolate spheroid, V=4/3×3.14×length/2×width/2×depth/2.

Results

Figure 9:
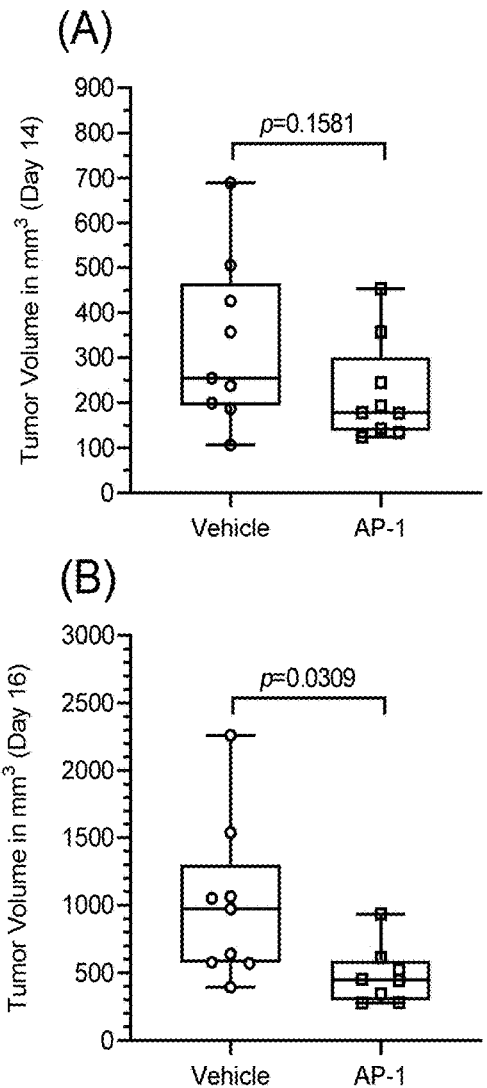
FIG. 9 demonstrates that demonstrates that AP-1 exhibits significant in vivo antitumor activity and delays tumor progression in a CB.17 SCID mouse xenograft model of human malignant melanoma. The depicted Whisker plots represent the median and values (Min to Max, all data points are shown) for the tumor volumes in each group on day 14 (Panel A; 9 mice in each group), and day 16 (Panel B; 9 control mice and 8 test mice). Statistical significance between the two groups is shown by the depicted p-values above the plots were computed using independent samples T-test ($p<0.05$). On day 16, the average tumor volume of AP-1 treated test mice was significantly smaller than the average tumor volume of vehicle treated control mice (484.3±76.5 mm3 vs. 1008.0±195.2 mm3, P=0.0309).

Vehicle treated control CB.17 SCID mice (N=9) developed rapidly growing tumors after s.c. inoculation of $1 \times 10^6$ M24-MET human melanoma cells. AP-1 significantly slowed down the tumor progression. The depicted Whisker plots in FIG. 9 represent the median and values (Min to Max. Shown all points) for the tumor volumes in each group on day 14 (FIG. 9A; 9 mice in each group), and day 16 (FIG. 9B; 9 control mice and 8 test mice). Statistical significance between the two groups is shown by the depicted p-values above the plots were computed using independent samples T-test (p<0.05). On day 16, the average tumor volume of AP-1 treated test mice was significantly smaller than the average tumor volume of vehicle treated control mice (484.3±76.5 mm3 vs. 1008.0±195.2 mm3, P=0.0309) (FIG. 9B).

Example 7. Novel Cinchona Alkaloid AP-8 Exhibits Significant In Vivo Antitumor Activity and Delays Tumor Progression in a SCID Mouse Xenograft Model of Human Prostate Cancer Methods Cell Lines. Human prostate cancer cell line PC3 (ATCC CRL-1435) was obtained from American Type Culture Collection (Rockville, Md.) and maintained as a continuous cell line in DMEM supplemented with 10% fetal calf serum (FCS), 4 mm glutamine, 100 units/ml penicillin G, and 100 mg/ml streptomycin sulfate. All of the tissue culture reagents were obtained from Life Technologies, Inc. Inc. (Gaithersburg, Md.).

Mice. Female CB.17 SCID mice were obtained from Taconic (Germantown, N.Y.) and housed in a specific-pathogen-free room located in a secure indoor facility with controlled temperature, humidity, and noise levels. Mice were housed in micro-isolator cages and fed with autoclaved rodent chow. Water was also autoclaved and supplemented with trimethoprim/sulfamethoxazol 3 days a week. The animal protocol used in this study was approved by the Drug Discovery Enterprises Animal Care and Use Committee (IACUC), and all of the animal care procedures conformed to the Guide for the Care and Use of Laboratory Animals (National Research Council, National Academy Press, Washington D.C. 1996).

SCID Mouse Model of Human Prostate Cancer. The predictive value of the mouse xenograft models for clinical effectiveness of anti-cancer drugs has been confirmed for several drugs (Richmond A. Su Y. Mouse xenograft models vs GEM models for human cancer therapeutics. *Dis Model Mech.* 2008; 1(2-3):78-82. doi:10.1242/dmm.000976). CB.17 SCID mice (8 wk old, female) were inoculated subcutaneously with $1 \times 10^6$ PC3 human prostate cancer cells ($1 \times 10^6$/inoculum, volume: 200 µL) in the right flank. Mice were treated twice daily with intraperitoneal injections of vehicle (50 µL DMSO) (N=10) or AP-1 (50 µg~2 mg/kg in 50 µL DMSO) (N=9) according to a 5 days on 2 days off schedule. Treatments were initiated 7 days after inoculation of PC-3 cells. The size of subcutaneous tumors were measured on day 16 and day 18 to evaluate the ability of AP-8 to inhibit tumor growth in this SCID mouse xenograft model of prostate cancer. Tumor volumes were calculated using the formula for the volume of a prolate spheroid, V=4/3×3.14×length/2×width/2×depth/2.

Results

Figure 10:
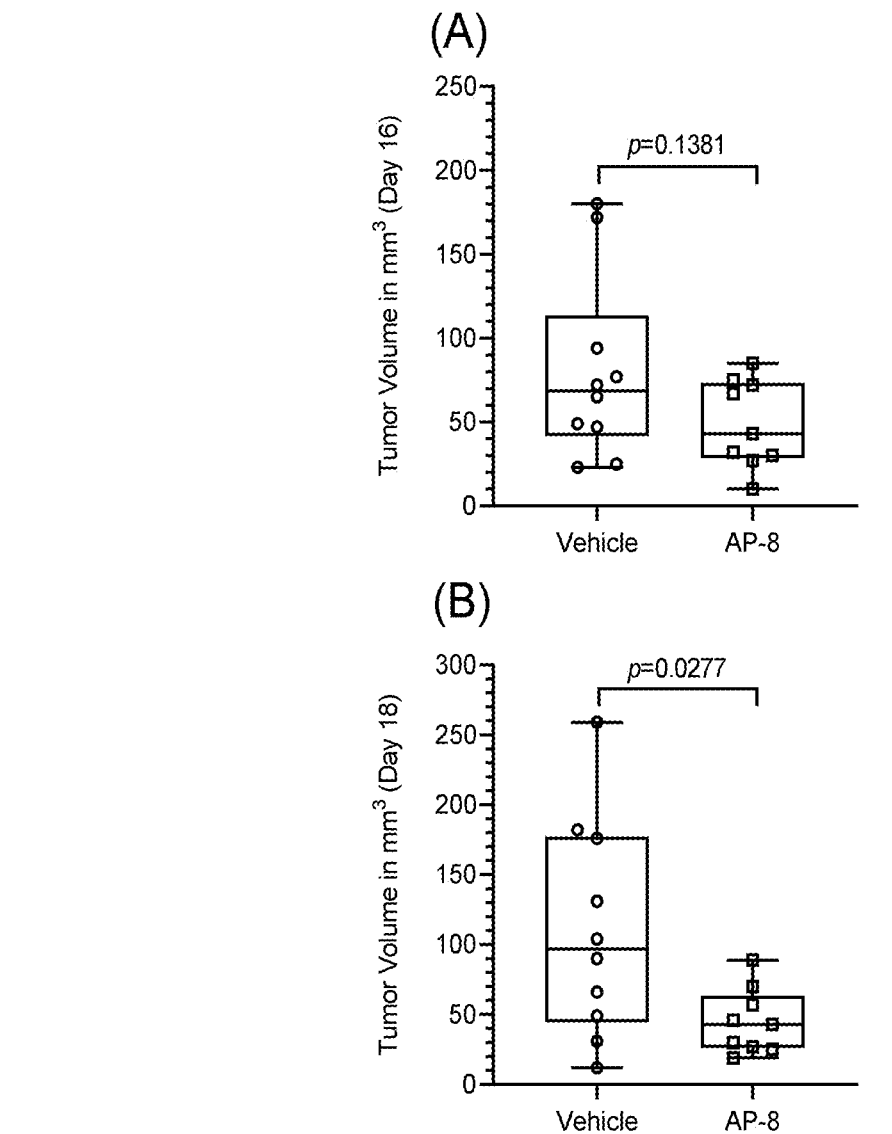
FIG. 10 demonstrates that demonstrates that AP-8 exhibits significant in vivo antitumor activity and delays tumor progression in a CB.17 SCID mouse xenograft model of human prostate cancer. The depicted Whisker plots represent the median and values (Min to Max. all points are shown) for the tumor volumes in each group on day 16 (Panel A; 10 control mice and 9 test mice), and day 18 (Panel B; 10 control mice and 9 test mice). Statistical significance between the two groups is shown by the depicted p-values above the plots were computed using independent samples T-test ($p<0.05$). On day 18, the average tumor volume of AP-8 treated test mice was significantly smaller than the average tumor volume of vehicle treated control mice (45.1±7.8 mm3 vs. 110.0±24.5 mm3, P=0.0277). Also depicted is a descriptive data summary table (Panel C).

Vehicle treated control CB.17 SCID mice (N=10) developed rapidly growing tumors after s.c. inoculation of $1 \times 10^6$ PC3 human prostate cancer cells. AP-8 significantly slowed down the tumor progression. The depicted Whisker plots in FIG. 10 represent the median and values (Min to Max. all data points are shown) for the tumor volumes in each group on day 16 (A; 10 control mice and 9 test mice), and day 18 (B; 10 control mice and 9 test mice). Statistical significance between the two groups is shown by the depicted p-values above the plots were computed using independent samples T-test (p<0.05). On day 18, the average tumor volume of AP-8 treated test mice was significantly smaller than the average tumor volume of vehicle treated control mice (45.1±7.8 mm$^3$ vs. 110.0±24.5 mm$^3$, P=0.0277).

Example 8. AP-1 and AP-8 Exhibit Potent Anti-Cancer Activity in a Syngeneic Mouse Model of K-Ras Mutant Non-Small Cell Lung Cancer (NSCLC)

Methods

Lewis Lung Carcinoma Cells (LL2) were purchased from ATCC. These murine NSCLC cells derived from C57BL/6 mice have a heterozygous Kras$^{G12C}$ mutation (H. Y. Li et al., 2017, Cancer Immunol. Res. 5:767-77; B. Deskin et al., 2020, Translational Oncol. 13:135-45). Eight-9 weeks old, male C57/BL6 mice were inoculated with 1×106 LL2 cells in 200 µL PBS that were injected subcutaneously in the right flank. Treatments were initiated immediately after inoculation with LL/2 cells. Control mice were treated with intraperitoneal injections of 50 µL vehicle (DMSO), whereas test mice were treated with either AP-1 or AP-8 at the specified dose levels. Treatments were administered twice daily, 5 days per week for a total of 2 weeks. The clinical predictive value of this mouse model is well established (Kellar A, Egan C, Morris D. Preclinical Murine Models for Lung Cancer: Clinical Trial Applications. Biomed Research International Volume 2015|Article ID 621324|https://doi.org/10.1155/2015/621324).

Results

AP-1 is Active Against NSCLC

Figure 11:
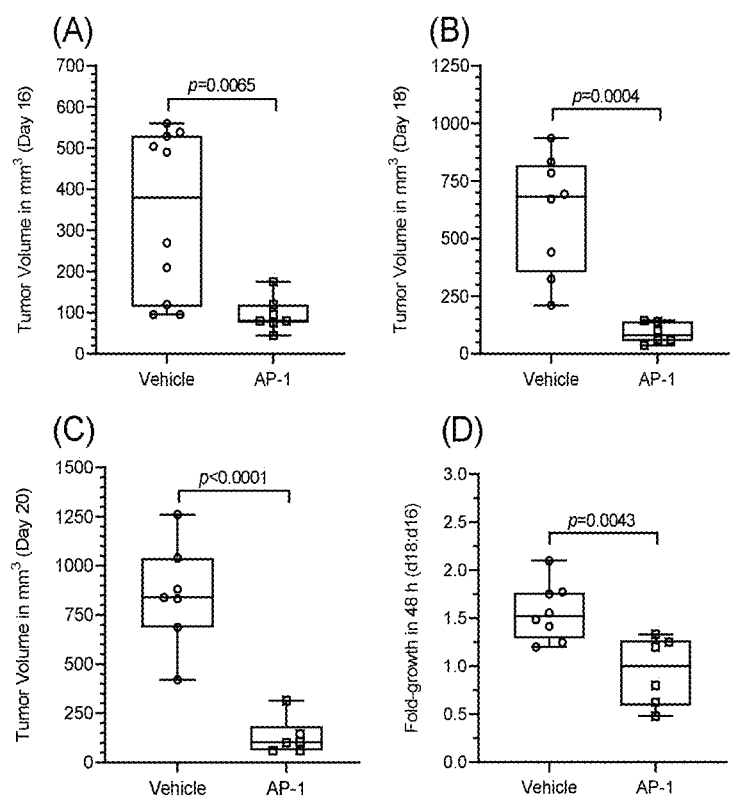
FIG. 11 demonstrates that AP-1 exhibits potent anti-cancer activity in a syngeneic mouse model of K-Ras mutant non-small cell lung cancer (NSCLC). The tumor volumes were measured on day 16 (Panel A), day 18 (Panel B), and day 20 (Panel C) measured in vehicle-treated control mice vs. AP-1 treated test mice. The average tumor volume in mice treated with AP-1 injections remained significantly smaller than the average tumor volume in vehicle-treated control mice. The depicted Whisker plots represent the median and values (Min to Max. Shown all points) for the tumor volume on day 16 (A), day 18 (B) and day 20 (C), and fold-growth in 48 hours (D; day 18 size: day 16 size) measured in tumors from mice in each group. AP-1 significantly reduced the rapid growth rate of the LL2 tumors as demonstrated by its pronounced effect on fold-growth in 48 hours between day 16 and day 18. Statistical significance between the two groups is shown by the depicted p-values above the plots were computed using independent samples T-tests.

In the 1$^{st}$ experiment, mice were treated twice daily with intraperitoneal injections of vehicle (50 µL DMSO) (N=10) or AP-1 (125 µg~5 mg/kg in 50 µL DMSO) (N=7) according to a 5 days on 2 days off weekly schedule for 4 weeks. Mice were monitored daily until tumors became visible on and tumor growth rates were compared between day 16 and day 20 by measuring the size of the tumors with a caliper in three dimensions. Tumor size was expressed as tumor volume in cubic millimeters (mm3). Tumor volumes were calculated using the formula for the volume of a prolate spheroid, V=4/3×3.14×length/2×width/2×depth/2. As shown in FIG. 11 (6.2), the average tumor volume in mice treated with AP-1 injections remained significantly smaller than the average tumor volume in vehicle-treated control mice. The depicted Whisker plots represent the median and values (Min to Max. Shown all points) for the tumor volume on day 16 (FIG. 11A), day 18 (FIG. 11 FIG. 11B) and day 20 (C), and fold-growth in 48 hours (FIG. 11D; day 18 size: day 16 size) measured in tumors from mice in each group. AP-1 significantly reduced the rapid growth rate of the LL2 tumors as demonstrated by its pronounced effect on fold-growth in 48 hours between day 16 and day 18. Statistical significance between the two groups is shown by the depicted p-values above the plots were computed using an independent samples T-test.

Figure 12:
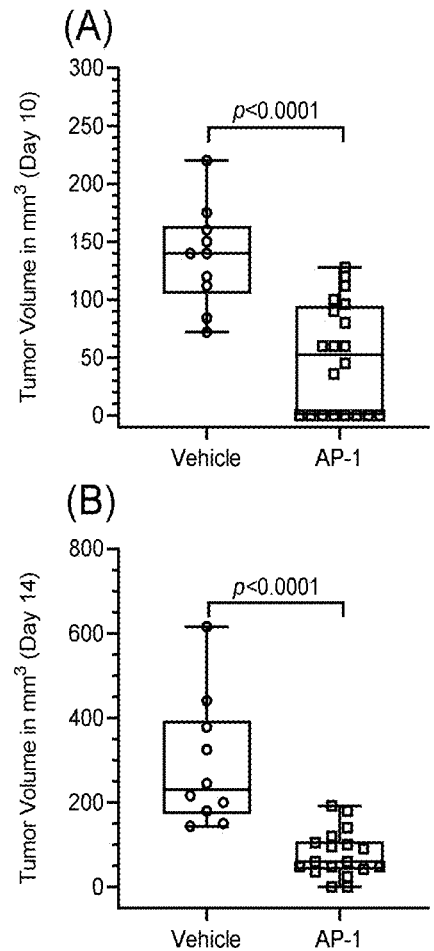
FIG. 12 further demonstrates that AP-1 exhibits potent anti-cancer activity in a syngeneic mouse model of K-Ras mutant non-small cell lung cancer (NSCLC). The depicted Whisker plots represent the median and values (Min to Max. all data points are shown) for the tumor volumes measured on day 10 (Panel A), and day 14 (Panel B) in vehicle-treated control mice vs. AP-1 treated test mice in the 2nd experiment. Also depicted is a descriptive data summary table (Panel C). The ability of AP-1 to arrest the tumor growth in each of the treated mice is demonstrated by the clear separation of the range of the tumor volumes for the AP-1 vs. Vehicle treatment groups as depicted in the summary data table and Whisper plots of day 10 ($P<0.0001$) and day 14 ($P<0.0001$) tumor volumes of individual mice. The average tumor volume in mice treated with AP-1 injections remained significantly smaller than the average tumor volume in vehicle-treated control mice. Statistical significance between the two groups is shown by the depicted P-values above the plots were computed using an independent samples T-test.

Similarly, in the 2$^{nd}$ experiment, C57BL/6 mice were inoculated subcutaneously with LL2 cells (1×10$^6$/inoculum, volume: 200 µL) in the right flank. Mice were treated twice daily with intraperitoneal injections of vehicle (50 µL DMSO) (N=10) or AP-1 (100 µg~4 mg/kg in 50 µL DMSO) (N=20) according to a 5 days on 2 days off weekly schedule for 2 weeks. Mice were monitored daily until tumors became visible on day 10. Tumor growth was assessed on day 10 and day 14 by measuring the size of the tumors with a caliper in three dimensions. Tumor size was expressed as tumor volume in cubic millimeters (mm³). Tumor volumes were calculated using the formula for the volume of a prolate spheroid, V=4/3×3.14×length/2×width/2×depth/2. The ability of AP-1 to arrest the tumor growth in each of the treated mice is demonstrated by the clear separation of the range of the tumor volumes for the AP-1 vs. Vehicle treatment groups as depicted in the summary data table and Whisker plots of day 10 (Panel A, P<0.0001) and day 14 (Panel B, P<0.0001) tumor volumes of individual mice in FIG. 12. The average tumor volume in mice treated with AP-1 injections remained significantly smaller than the average tumor volume in vehicle-treated control mice. Statistical significance between the two groups is shown by the depicted P-values above the plots were computed using an independent samples T-test.

Figure 14:
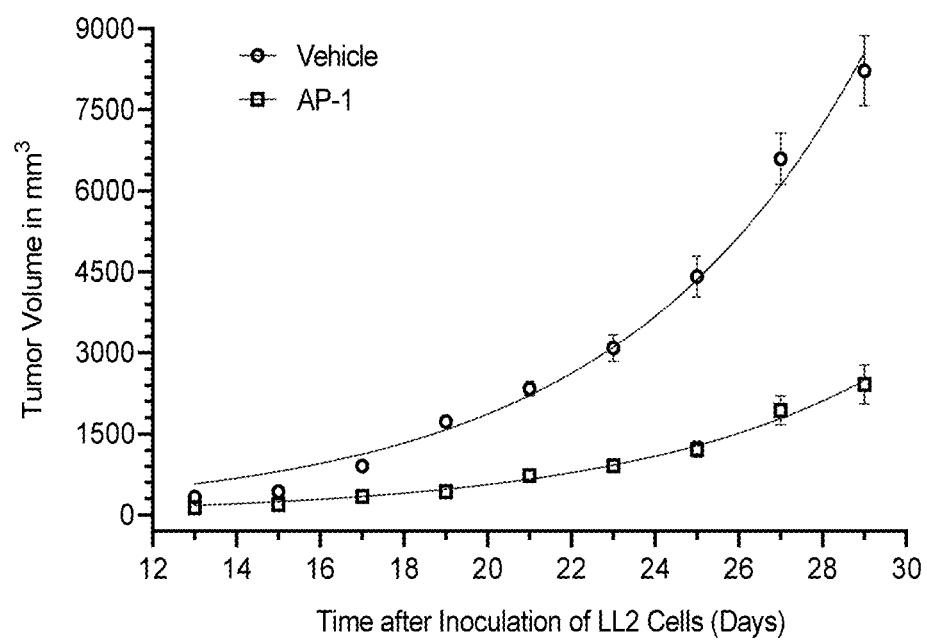
FIG. 14 demonstrates that AP-1 exhibits potent anti-cancer activity in a syngeneic mouse model of K-Ras mutant non-small cell lung cancer (NSCLC). Depicted are the corresponding tumor growth curves for the $3^{rd}$ experiment data shown in FIG. 13 that were generated the exponential growth equation in the nonlinear regression method to show the rate of change in tumor volumes. The depicted points represent the mean and standard error for the tumor volumes measured for each group—(P-value <0.0001 for AP-1 vs. Vehicle).

In the 3$^{rd}$ experiment, mice were treated twice daily with intraperitoneal injections of vehicle (50 μL DMSO) (N=10) or AP-1 (125 μg~5 mg/kg in 50 μL DMSO) (N=18) according to a 5 days on 2 days off weekly schedule for 4 weeks. Mice were monitored daily until tumors became visible on day 13. Tumor growth was re-assessed every other day between day 13 and day 29 by measuring the size of the tumors with a caliper in three dimensions. Tumor size was expressed as tumor volume in cubic millimeters (mm³). Tumor volumes were calculated using the formula for the volume of a prolate spheroid, V=4/3×3.14×length/2×width/2×depth/2. As shown in FIG. 13 and its descriptive summary data table, the average tumor volume in mice treated with AP-1 injections remained significantly smaller than the average tumor volume in vehicle-treated control mice. A two-way analysis of variance (ANOVA) model was used with Geisser-Greenhouse correction to evaluate the statistical significance of the overall effect of drug treatment across all time points and demonstrated a pronounced overall inhibitory effect of AP-1 on tumor growth. The P-value for each time point was computed using Sidak's multiple comparisons test and confirmed the statistical significance of the differences in the average tumor volume for each time point (*p<0.05; p<0.01; *p<0.001; ****p<0.0001). The corresponding tumor growth curves that were generated the exponential growth equation in the nonlinear regression method to show the rate of change in tumor volumes are depicted in FIG. 14. The depicted points represent the mean and standard error for the tumor volumes measured for each group —(P-value <0.0001 for AP-1 vs. Vehicle).

Figure 15:
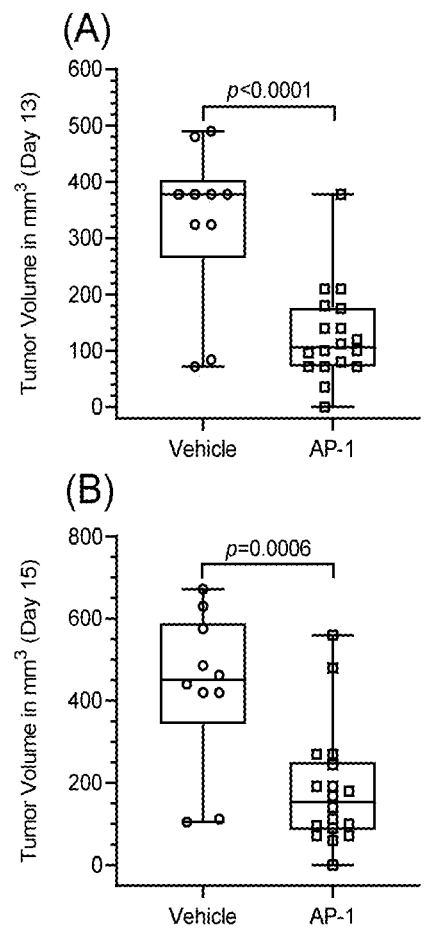
FIG. 15 further demonstrates that AP-1 exhibits potent anti-cancer activity in a syngeneic mouse model of K-Ras mutant non-small cell lung cancer (NSCLC). The ability of AP-1 to arrest the tumor growth in each of the treated mice in the $3^{rd}$ experiment is demonstrated by the clear and statistically significant separation of the range of the tumor volumes for the AP-1 vs. Vehicle treatment groups as depicted in the Whisper plots of day 13 (P<0.0001) and day 15 (P=0.0006) tumor volumes of individual mice. The depicted Whisker plots represent the median and values (Min to Max. Shown all points) for the tumor volume on day 13 (A) and day 15 (B) measured in tumors from mice in each group. Statistical significance between the two groups is shown by the depicted P-values above the plots were computed using an independent samples T-test.

The ability of AP-1 to arrest the tumor growth in each of the treated mice is demonstrated by the clear and statistically significant separation of the range of the tumor volumes for the AP-1 vs. Vehicle treatment groups as depicted in the Whisper plots of day 13 (P<0.0001) and day 15 (P=0.0006) tumor volumes of individual mice in FIG. 15. The depicted Whisker plots in FIG. 15. represent the median and values (Min to Max. Shown all points) for the tumor volume on day 13 (Panel A) and day 15 (Panel B) measured in tumors from mice in each group. Statistical significance between the two groups is shown by the depicted P-values above the plots were computed using an independent samples T-test.

AP-8 is Active Against NSCLC

Figure 16:
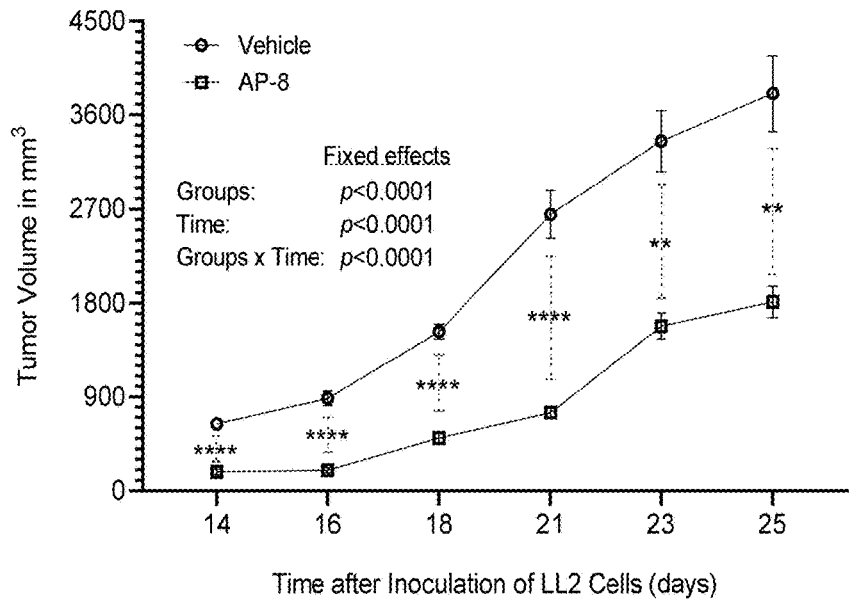
FIG. 16 demonstrates that AP-8 exhibits potent anti-cancer activity in a syngeneic mouse model of K-Ras mutant non-small cell lung cancer (NSCLC). As evidenced by the depicted tumor growth curves and the descriptive summary data table, the average tumor volume in mice treated with AP-8 injections remained significantly smaller than the average tumor volume in vehicle-treated control mice. A two-way analysis of variance (ANOVA) model was used with Geisser-Greenhouse correction to evaluate the statistical significance of the overall effect of drug treatment across all time points and demonstrated a pronounced overall inhibitory effect of AP-8 on tumor growth. The P-value for each time point was computed using Sidak's multiple comparisons test and confirmed the statistical significance of the differences in the average tumor volume for each time point (*p<0.05; p<0.01; *p<0.001; ****p<0.0001).
Figure 17:
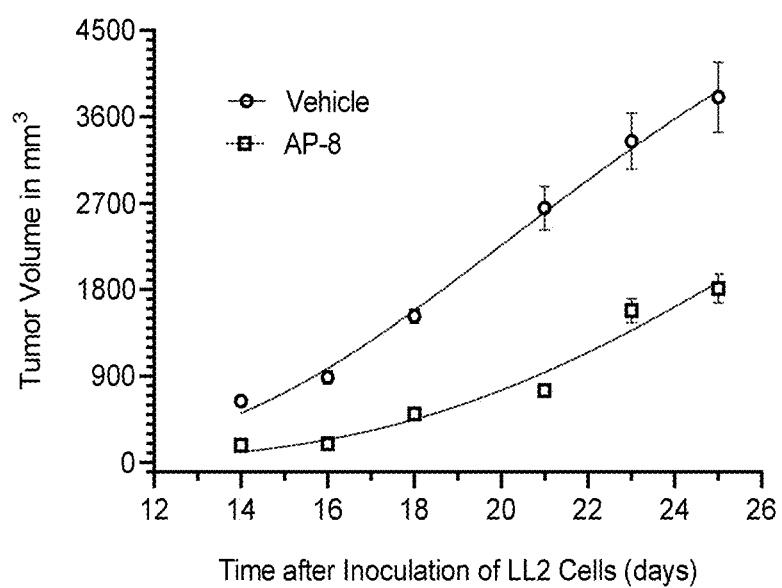
FIG. 17 demonstrates that AP-8 exhibits potent anti-cancer activity in a syngeneic mouse model of K-Ras mutant non-small cell lung cancer (NSCLC). Depicted are the corresponding tumor growth curves for the data shown in FIG. 16 that were generated the exponential growth equation in the nonlinear regression method to show the rate of change in tumor volumes. The depicted points represent the mean and standard error for the tumor volumes measured for each group—(P-value <0.0001 for AP-8 vs. Vehicle).
Figure 18:
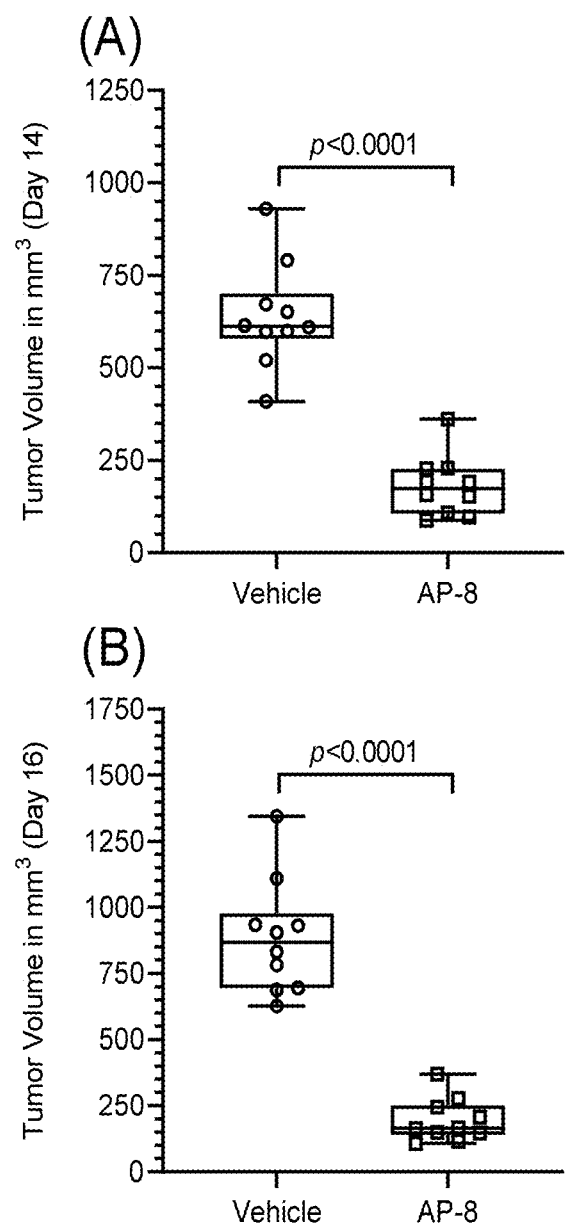
FIG. 18 further demonstrates that AP-8 exhibits potent anti-cancer activity in a syngeneic mouse model of K-Ras mutant non-small cell lung cancer (NSCLC). The ability of AP-8 to arrest the tumor growth in each of the treated mice is demonstrated by the clear and statistically significant separation of the range of the tumor volumes for the AP-8 vs. Vehicle treatment groups as depicted in the Whisper plots of day 14 (P<0.0001) and day 16 (P<0.0001) tumor volumes of individual mice. The depicted Whisker plots represent the median and values (Min to Max. all data points are shown) for the tumor volume on day 14 (Panel A) and day 16 (Panel B) measured in tumors from mice in each group. Statistical significance between the two groups is shown by the depicted P-values above the plots were computed using an independent samples T-test.

Mice were treated twice daily with intraperitoneal injections of vehicle (50 μL DMSO) (N=10) or AP-1 (50 μg~2 mg/kg in 50 μL DMSO) (N=10) according to a 5 days on 2 days off weekly schedule for 4 weeks. Mice were monitored daily until tumors became visible and measurable on day 14. Tumor growth was re-assessed every other day between day 14 and day 25 by measuring the size of the tumors with a caliper in three dimensions. Tumor size was expressed as tumor volume in cubic millimeters (mm3). Tumor volumes were calculated using the formula for the volume of a prolate spheroid, V=4/3×3.14×length/2×width/2×depth/2. As shown in FIG. 16, the average tumor volume in mice treated with AP-8 injections remained significantly smaller than the average tumor volume in vehicle-treated control mice. The corresponding tumor growth curves that were generated using the exponential growth equation in the nonlinear regression method to show the rate of change in tumor volumes are depicted in FIG. 17 (P-value <0.0001 for AP-8 vs. Vehicle). A two-way analysis of variance (ANOVA) model was used with Geisser-Greenhouse correction to evaluate the statistical significance of the overall effect of drug treatment across all time points and demonstrated a pronounced overall inhibitory effect of AP-8 on tumor growth. The P-value for each time point was computed using Sidak's multiple comparisons test and confirmed the statistical significance of the differences in the average tumor volume for each time point (*p<0.05; p<0.01; *p<0.001; ****p<0.0001) (FIG. 16). The ability of AP-8 to arrest the tumor growth in each of the treated mice is demonstrated by the clear separation of the range of the tumor volumes for the AP-8 vs. Vehicle treatment groups as depicted in the Whisker plots of day 14 and day 16 tumor volumes of individual mice (P<0.0001, FIG. 18). Statistical significance between the two groups is shown by the depicted p-values above the plots were computed using an independent samples T-test.

Example 9: AP-8 (2,4,6-Tri (9-O-dihydroquinidinyl)pyrimidine) Exhibits Potent Anti-Cancer Activity Against Chemotherapy-Resistant Aggressive Breast Cancer in MMTV/Neu Transgenic Mice Methods The predictive value of genetically engineered mouse (GEM) models to predict the clinical effectiveness of anti-cancer drugs is well established (Richmond A, Su Y. Mouse xenograft models vs GEM models for human cancer therapeutics. *Dis Model Mech.* 2008; 1(2-3):78-82. doi:10.1241-2/dmm.0.000976). We used the transgenic mouse model of HER2+ chemotherapy-resistant breast cancer to examine the in vivo anti-cancer activity of AP-8. Overexpression of the wild type Neu in the mammary glands of transgenic mice induces metastatic breast cancer. Accordingly, in the MMTV/Neu transgenic strain, the wild-type neu is overexpressed in the mammary gland under the control of the MMTV long terminal repeat. This animal model has been used to analyze the efficacy of new therapeutic approaches to prevent or treat Her2/neu overexpressing malignancies (Uckun, Dibirdik). MMTV/Neu transgenic mice [FVB/N-TgN(MMTV/neu)202MUL; Jackson Laboratory, Bar Harbor, Me.] were bred to produce multiple litters in a controlled SPF environment (12 h light/12 h-dark photoperiod, 22±1° C., 60±10% relative humidity). All mice were housed in microisolator cages (Lab Products, Inc., Maywood, N.Y., USA) containing autoclaved bedding in a controlled specific pathogen-free (SPF) environment (12 h light/12 h-dark photoperiod, 22±1° C., 60±10% relative humidity). Animal studies were approved by the institutional Animal Care and Use Committee of Drug Discovery Enterprises and all animal care procedures conformed to the Guide for the Care and Use of Laboratory Animals of the National Research Council. The genotype of mice was confirmed by multiplex polymerase chain reaction (PCR) tests as previously reported (F. M. Uckun et al., 2007, Bioorganic Med. Chem. 15:800-14; I. Dibirdik et al., 2010, J Nanomed and Nanotechnol. 1:001-4).

Neu transgenic mice carrying one or more tumors were randomly placed in the study. For the evaluation of tumor kinetics, tumor-bearing mice were randomly assigned to either vehicle control or treatment groups. Tumor growth was determined by the measurement of tumors with a caliper in three dimensions three days a week and expressed as tumor volume in cubic millimeters ($mm^3$). Tumor volumes were calculated using the formula for the volume of a prolate spheroid, $V=4/3 \times 3.14 \times length/2 \times width/2 \times depth/2$. Due to the large heterogeneity in transgenic tumor volumes on day 0, tumor growth for each mouse was normalized to the starting volume for that particular tumor. Therefore, each mouse also served as its own control, and the tumor growth curves were generated to show the rate of change in tumor volumes.

AP-8 (50 µg~2 mg/kg in 50 µL DMSO as vehicle) (10 mice, 12 target mammary tumors, Initial average tumor volume=787±125 $mm^3$) was administered by twice daily intraperitoneal injections on 5 consecutive days per week. Paclitaxel (10 mice, 13 target mammary tumors, Initial average tumor volume=554±79 $mm^3$) was administered intraperitoneally on days 1, 3, and 5 of each week at a dose level of 6.7 mg/kg (~200 $mg/m^2$). Gemcitabine (13 mice, 18 target mammary tumors, Initial average tumor volume=549±60 $mm^3$) was administered intraperitoneally on days 1 and 8 every 4 weeks at a dose level of 33.7 mg/kg (~1 $g/m^2$). Control mice (8 mice, 10 mammary tumors, Initial average tumor volume=293±61 $mm^3$) were treated by twice daily intraperitoneal injections of vehicle alone (50 µL DMSO) on 5 consecutive days per week. The initial tumor volumes of vehicle-treated control mice were smaller than the initial tumor volumes of mice treated with AP-8 or the standard chemotherapy drugs. AP-8 treated test mice had the largest initial pretreatment tumor volumes than the mice in any of the other 3 treatment groups.

Results

Figure 19:
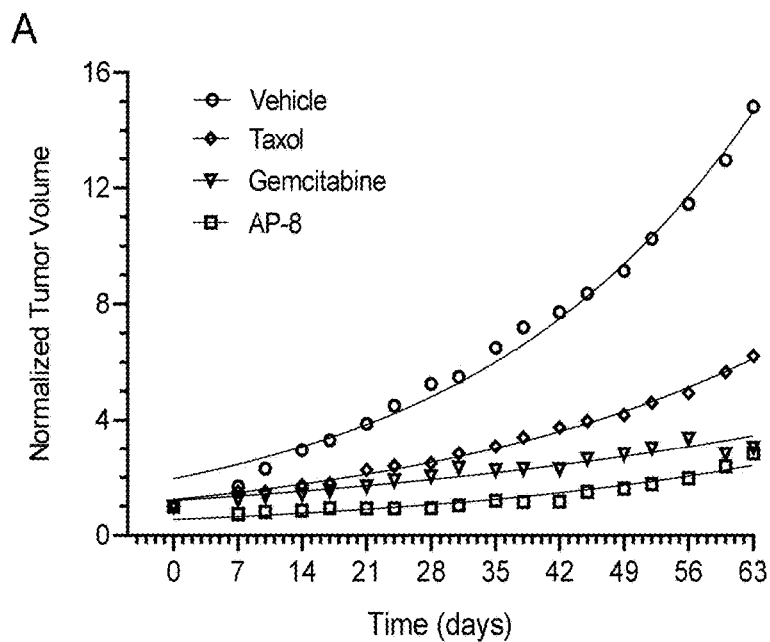
FIG. 19 demonstrates that AP-8 exhibits potent in vivo anti-cancer activity and markedly delays tumor progression in MMTV/neu transgenic mice with established mammary tumors. [Panel A] Depicted are tumor growth curves for mice treated with AP-8 vs. Vehicle alone, Paclitaxel (Taxol), or Gemcitabine. 9-week tumor growth curves were generated using the exponential growth equation and the nonlinear regression method. Each datapoint represents the mean value for the measured tumor volume at the depicted time-point. The P-value for the comparison of the tumor growth curves for AP-1 vs. Vehicle was <0.0001. [Panel B] Normalized tumor volumes (mean±SE values) are presented for Weeks 2, 4, and 8 after initiation of therapy. Statistical significance in the pairwise comparison of the groups is shown with a superscript * p<0.05;  p<0.01;  p<0.001; **** p<0.0001 compared as Vehicle group or #P<0.05; ##P<0.01 compared as AP-8 group. The P-values were computed using an independent T-test.

FIG. 19, Panel A depicts tumor growth curves for mice treated with AP-8 vs. Vehicle alone, Paclitaxel (Taxol), or Gemcitabine. 9-week tumor growth curves were generated using the exponential growth equation and the nonlinear regression method. Each datapoint represents the mean value for the measured tumor volume at the depicted timepoint. The P-value for the comparison of the tumor growth curves for AP-1 vs. Vehicle was <0.0001. In FIG. 19, Panel B, the normalized tumor volumes (mean±SE values) are presented for Weeks 2, 4, and 8 after initiation of therapy. Statistical significance in the pairwise comparison of the groups is shown with a superscript * p<0.05;  p<0.01;  p<0.001; ****p<0.0001 compared as Vehicle group or #P<0.05; ##P<0.01 compared as AP-8 group. The P-values were computed using an independent T-test.

As evidenced in FIG. 19, the tumors of vehicle-treated control mice rapidly grew 14.8-fold within the 9-week observation period. AP-8 caused shrinkage of the tumor, completely arrested the tumor growth for 4 weeks, and markedly delayed the tumor progression between 4 weeks and 9 weeks. Neither paclitaxel nor gemcitabine at the clinically applicable dose levels used in these experiments induced tumor shrinkage and they were less effective than AP-8 in preventing tumor progression. Considering the fact that the AP-8 treated test mice had the largest initial pretreatment tumor volumes than the mice in any of the other 3 treatment groups, the observed superiority of AP-8 in comparison to the other treatments in the MMTV/neu transgenic mouse model of HER2+ aggressive breast cancer provides compelling proof of concept that AP-8 has clinical impact potential as a novel treatment against aggressive breast cancer.

Abbreviations

H: hydrogen; Me: Methyl; Et: Ethyl; Pr: Propyl; Bu: Butyl; tBu: tertiary butyl; Ph: Phenyl; $PhCH_2$: Benzyl; OH: hydroxy; OMe: Methoxy; OEt: ethoxy; OPr: propyl oxy; OBu: Butoxy, OtBu: tertiary butoxy; OPh: phenoxy; $OCH_2Ph$: Benzyl oxy; F: Fluorene; Cl: Chlorine; Br: Bromine; I: Iodine; COOH: Carboxyl; COOMe: methyl carboxy; COOEt: ethyl carboxy, $CH=CH_2$, ethene.

Linkers Chosen from the Following List:

2,3,5,6-tetrafluoro pyridine; 2,4-dichloro-5-bromo-pyridine, 2,4,6-trifluoro-3,5-dichloropyridine; 2,4,6-trifluoro-5-chloropyrimidine; 2,3,5,6-tetrafluoro 4-methyl pyridine ; 2,3,4,5,6 penta halo pyridine; 2,3,5,6 tetra chloro pyrazine; 3,4,5,6 tetrachloro pyridazine; 2,4,5,6 tetrachloro pyrimidine; Tri or tetra Halo substituted pyridazine, pyrazine and pyrimidines in general.

REFERENCE CITED

Numerous publications have been cited in the text of this specification. Each such publication is expressly incorporated herein by reference for all purposes, as if fully set forth.

Patents

1. P. Boratynski and J. Skarzewski, Polish Potent PL215 451B1 issued on Dec. 31, 2013. "Epoxy derivatives of the cinchona alkaloids and process for the preparation of the epoxy derivatives of cinchona alkaloids", 2013.
2. L. Celewicz, K. Kacprzak, P. Ruszkowski, U.S. Pat. No. 9,301,956B2 issued on Apr. 5, 2016, "Application of cinchona alkaloid derivatives as cytotoxic compounds". 2016. PCT Pub. No.: WO2015/041551, Pub. Date: Mar. 26, 2015
3. L. Celewicz, K. Kacprzak, P. Ruszkowski, Canadian Patent #2891633 issued on Mar. 26, 2015 "Application of Cinchona Alkaloid derivatives as cytotoxic compounds". 2015.
4. P. A. Genne and H. Ibrahim, U.S. Pat. No. 6,528,524 issued Mar. 4, 2003. Pharmaceutical compositions containing cinchonine dichlorohydrate; PCT Pub. No. WO98/56383, PCT Pub. Date: Dec. 17, 1998
5. B. D. Chauffert, P. A. Genne, G. G. Lyon. All of France; Roland-Yves Mauvernay. Lausanne, Switzerland; U.S. Pat. No. 5,635,515 issued Jun. 3, 1997; "Therapeutic Agents for the treatment of multidrug resistance of cancers". 1997.
6. M. Padval, P. Elliott, U.S. Pat. No. 112,199 issued May 26, 2005. "Therapeutic Regimens for administering drug combinations"0.2005.
7. I. Yutaka, M. Yasushi, F. Yoshiro, M. Osaka, European Patent #1 477 488A1 issued on Nov. 17, 2004. "Novel Optically active compounds, methods for kinetic optical resolution of carboxylic acid derivatives and catalysts therefor", 2004.

Journal Publications

1. J. A. Baldwin, M. D. McLeod. The Sharpless asymmetric amino dihydroxylation. J. Chem Soc. Perkin Trans. 2002; 1, 2733-2746.

2. P. J. Boratynski, Dimeric Cinchona alkaloids. Comprehensive Review. Mol Divers 2015; 19, 385-422
3. R. T. Brown and D. Curless, Stereospecific synthesis of erythron cinchona alkaloids from secologanin, Tetrahedron Letters. 1986; 27(49), 6005-6008.
4. K. K. Chavez, S. V. Garimella, S. Lipkowitz. Triple negative breast cancer cell lines: one tool in the search for better treatment of triple negative breast cancer. Breast Dis. 2010; 32(1-2),35-48. doi:10.3233/BD-2010-0307
5. S. R. Chemler. Phenanthroindolizidines and phenanthroquinolizidines: Promising alkaloids for anti-cancer therapy. Curr Bioact Compd 2009; 5(1), 2-19.
6. Cuendet M, Pezuto J M. Antitumor Alkaloids in Clinical Use or in Clinical Trials. [In] Modern Alkaloids: Structure, Isolation, Synthesis and Biology. 2007; pp. 25-52. Eds.: E. Fattorusso, O. Taglialatela-Scafati. Print ISBN: 9783527315215|Online ISBN:9783527621071|DOI: 10.1002/9783527621071. First published: 24 Oct. 2007. Wiley Online Library.
7. C. Fitzmaurice et al., *Global, Regional, and National Cancer Incidence, Mortality, Years of Life Lost, Years Lived With Disability, and Disability-Adjusted Life-Years for 29 Cancer Groups, 1990 to 2017: A Systematic Analysis for the Global Burden of Disease Study*. JAMA Oncol. 2019 Sep. 27; 5(12):1749-68. doi: 10.1001/jamaoncol.2019.2996.
8. M. Ihara, N. Taniguchi, K. Noguchi, K. Fukumoto, Total synthesis of hydrocinchonidine and hydrocinchonine via photo-oxygenation of an indole derivative, J. Chem. Soc. Perkin Trans. 1988; 1, 1277-1281.
9. H. C. Kolb, M. S. Van Nieuwenhze, K. B. Sharpless. Catalytic asymmetric dihydroxylation. Chem. Rev. 2004; 94, 2483-2547.
10. A. Lee, F. C. Lee Medical oncology management of advanced hepatocellular carcinoma 2019: a reality check. Front Med. 2020 June; 14(3):273-283. doi: 10.1007/s11684-019-0728-2.
11. S Y Lee, Y H Rhee, S J Jeong, H J Lee, *Hydrocinchonine, cinchonine, and quinidine potentiate paclitaxel-induced cytotoxicity and apoptosis via multidrug resistance reversal in MES-SA/DX5 uterine*. Environmental Toxicology. 2011; 26, 424-431.
12. A. R. Martirosyan, R Rahim-Bata, A B Freeman, *Differentiation-inducing quinolines as experimental breast cancer agents in the MCF-7 human breast cancer cell model*. Biochemical Pharmacology 2004; 68, 1729-1738.
13. N. M. Mattock and W. Peters. The experimental Chemotherapy of leishmaniasis" Annals of Tropical Medicine and Parasitology 1975; 69(4), 449-462.
14. D. E. Myers, S. Yiv, S. Qazi, H. Ma, I. Cely, A. Shahidzadeh, M. Arellano, E. Finestone, P. S. Gaynon, A. Termuhlen, J. Cheng, F. M. Uckun FM. *CD19-antigen specific nanoscale liposomal formulation of a SYK P-site inhibitor causes apoptotic destruction of human B-precursor leukemia cells*. Integr Biol (Camb). 2014 Jul. 21; 6(8):766-80. doi: 10.1039/c4ib00095a.
15. H. Rafei, H. M. Kantarjian, E. J. Jabbour. *Targeted therapy paves the way for the cure of acute lymphoblastic leukaemia*. Br J Haematol. 2020 January; 188(2):207-223. doi: 10.1111/bjh.16207. Epub 2019 Sep. 30.
16. K. V. Raju, P. Kharel, R. Pandey, R. Garje, A. B. Chandra, Review of Indications of FDA-Approved Immune Checkpoint Inhibitors per NCCN Guidelines with the Level of Evidence. Cancers 2020; 12(3), 738; https://doi.org/10.3390/cancers12030738
17. Rosenkranz V, Winke. Induction of apoptosis by alkaloids, non-protein amino acids and cardiac glycosides in human promyelocytic HL-60 cells. Z. Naturforsch. 2007; 62c, 458-466.
18. Rosenkranz V, Winke. Alkaloids Induce Programmed Cell Death in Bloodstream Forms of Trypanosomes (*Trypanosoma b. brucei*). Molecules 2008; 13, 2462-2473.
19. S. Schläger, B. Dräger. Exploiting plant alkaloids. Curr Opin Biotechnol (2016) 37, 155-64.
20. T. K. Sahin, O. H. Aktepe., F. M. Uckun, S. Yalcin. Anti-Prostate Cancer Activity of a Nanoformulation of the SYK Tyrosine Kinase Inhibitor C61. Anti-Cancer Drugs 2020; February 8. doi: 10.1097/CAD.0000000000000910. [Epub ahead of print]
21. E Solary, L Mannone, D Moreau, D Caillot, *Phase I study of cinchonine, a multidrug resistance reversing agent, combined with the CHVP regimen in relapsed and refractory lymphoproliferative*. Leukemia 2000; 14, 2085-2094.
22. H. Tao, L. Zuo L, H. Xu, C. Li, G. Qiao, M. Guo, X. Lin. Alkaloids as Anticancer Agents: A Review of Chinese Patents in Recent 5 Years. Recent Patents on Anticancer Drug Discovery 2020; 15, 2-13.
23. F. M. Uckun S. Qazi, H. Ma, L. Tuel-Ahlgren, Z. Ozer. STAT3 is a substrate of SYK tyrosine kinase in B-lineage leukemia/lymphoma cells exposed to oxidative stress. Proc. Natl. Acad. Sci. USA. 2010; 107(7): 2902-7.
24. F. M. Uckun, R. O. Ek, S. T. Jan, C. L. Chen, S. Qazi. Targeting SYK Kinase-Dependent Anti-Apoptotic Resistance Pathway in B-lineage Acute Lymphoblastic Leukemia (ALL) Cells with a Potent SYK Inhibitory Pentapeptide Mimic. British Journal of Haematology 2010; 149(4), 508-17.
25. F. M. Uckun, S. Qazi, I. Cely, K. Sahin, A. Shahidzadeh, I. Ozercan, Q. Yin, P. Gaynon, A. Termuhlen, J. Cheng, S. Yiv. *Nanoscale liposomal formulation of a SYK P-site inhibitor against B-precursor leukemia*. Blood. 2013 May 23; 121(21):4348-54. doi: 10.1182/blood-2012-11-470633. Epub 2013 Apr. 8. PMID: 23568490
26. F. M. Uckun, D. E. Myers, J. Cheng, S. Qazi. *Liposomal Nanoparticles of a Spleen Tyrosine Kinase P-Site Inhibitor Amplify the Potency of Low Dose Total Body Irradiation Against Aggressive B-Precursor Leukemia and Yield Superior Survival Outcomes in Mice*. EBioMedicine. 2015 Apr. 11; 2(6):554-62. doi: 10.1016/j.ebiom.2015.04.005.
27. F. M. Uckun, S. Qazi, Z. Ozer, A. L. Garner, J. Pitt, H. Ma, K. D. Janda. Inducing apoptosis in chemotherapy-resistant B-lineage acute lymphoblastic leukaemia cells by targeting HSPA5, a master regulator of the anti-apoptotic unfolded protein response signalling network. British Journal of Haematology. 2011; 153(6),741-752
28. F. M. Uckun, D. E. Myers, S. Qazi, Z. Ozer, R. Rose, O. J. D'Cruz, H. Ma. Recombinant human CD19L-sTRAIL effectively targets B cell precursor acute lymphoblastic leukemia. J Clin Invest. 2015 Mar. 2; 125(3):1006-18. doi: 10.1172/JCI76610.
29. F. M. Uckun, S. Qazi, T. Demirer, R. E. Champlin. *Contemporary patient-tailored treatment strategies against high risk and relapsed or refractory multiple myeloma*. EBioMedicine. 2019; January; 39:612-620. doi: 10.1016/j.ebiom.2018.12.004.

30. F. M. Uckun, S. Qazi, L. Hwang, V. N. Trieu. *Recurrent or Refractory High-Grade Gliomas Treated by Convection-Enhanced Delivery of a TGF@2-Targeting RNA Therapeutic: A Post-Hoc Analysis with Long-Term Follow-Up*. Cancers (Basel) 2019; 1(12). pii: E1892. doi: 10.3390/cancers11121892

31. R. K. Vaddepally, P. Kharel, R. Pandey, R. Garje, A. B. Chandra. Review of Indications of FDA-Approved Immune Checkpoint; Inhibitors per NCCN Guidelines with the Level of Evidence. Cancers 2020, 12, 738.

32. R. K. Narla, X. P. Liu, D. E. Myers, F. M. Uckun. 4-(3'-Bromo-4'hydroxylphenyl)-amino-6,7-dimethoxy-quinazoline. a novel quinazoline derivative with potent cytotoxic activity against human glioblastoma cells. Clin. Cancer Res., 4: 1405-1414, 1998.

33. F. M. Uckun FM, P. Goodman, H. Ma, I. Dibirdik, S. Qazi. CD22 exon 12 deletion as a novel pathogenic mechanism of human B-precursor leukemia. Proc Natl Acad Sci USA. 2010; 107(39):16852-16857. doi: 10.1073/pnas.1007896107.

34. F. M. Uckun, et al. Serine phosphorylation by SYK is critical for nuclear localization and transcription factor function of Ikaros. Proc Natl Acad Sci USA. 2012; 109(44):18072-18077. doi: 10.1073/pnas.1209828109.

35. F. M. Uckun, S. Morar, S. Qazi. Vinorelbine-Based Salvage Chemotherapy for Therapy-Refractory Aggressive Leukemias. Brit J Haematol. 2006; 135(4): 500-508

36. R. K. Narla, C. L. Chen, Y. Dong, F. M. Uckun. In vivo antitumor activity of bis(4,7-dimethyl-1,10-phenanthroline) sulfatooxovanadium(IV) (METVAN [VO(SO4)(Me2-Phen)2]). Clin Cancer Res. 2001; 7(7): 2124-2133

37. H. Y. Li, M. McSharry, B. Bullock, T. T. Nguyen, J. Kwak et al. The Tumor Microenvironment Regulates Sensitivity of Murine Lung Tumors to PD-1/PD-L1 Antibody Blockade. Cancer Immunol Res. 2017 September; 5(9):767-777. doi: 10.1158/2326-6066.CIR-16-0365. Epub 2017 Aug. 17. PMID: 28819064; PMCID: PMC5787226.

38. B. Deskin, Q. Yin, Y. Zhuang, S. Saito, B. Shan, J. A. Lasky. Inhibition of HDAC6 Attenuates Tumor Growth of Non-Small Cell Lung Cancer. *Translational Oncology* 2020; 13(2):135-145.

39. I. Dibirdik, S. Yiv, S. Qazi S, F. M. Uckun. In vivo anti-cancer activity of a liposomal nanoparticle construct of multifunctional tyrosine kinase inhibitor 4-(4'-hydroxyphenyl)-amino-6,7-dimethoxyquinazoline. Journal of Nanomedicine & Nanotechnology 2010; 1(1): 001-004

40. F. M. Uckun et al. Anti-breast cancer activity of LFM-A13, a potent inhibitor of Polo-like kinase (PLK). Bioorg Med Chem. 2007; 15(2): 800-814

41. Kellar A, Egan C, Morris D. Preclinical Murine Models for Lung Cancer: Clinical Trial Applications. Biomed Research International Volume 2015 I Article ID 621324 I https://doi.org/10.1155/2015/621324).

42. Richmond A. Su Y. Mouse xenograft models vs GEM models for human cancer therapeutics. *Dis Model Mech.* 2008; 1(2-3):78-82. doi:10.1242/dmm.00976

43. Xu C, Li X, Liu P, Li M and Luo F: Patient-derived xenograft mouse models: A high fidelity tool for individualized medicine (Review). Oncol Lett 17: 3-10, 2019

44. Ayyanar Siva, Eagambaram Murugan. A New Trimeric Cinchona Alkaloid as a Chiral Phase-Transfer Catalyst for the Synthesis of Asymmetric a-Amino Acids. Synthesis 2005; 17:2927-2933. https://www.thieme-connect.de/media/synthesis/200517/lookinside/10.1055-s-2005-872170-1.jpg 45. Hyeung-geun Park, Byeong-seon Jeong, Mi-sook Yoo, Mi-kyoung Park, Hoon Huh, Sang-sup Jew. Trimeric Cinchona alkaloid phase-transfer catalyst: α,α',α"-tris[0 (9)-allylcinchonidinium]mesitylene tribromide, Tetrahedron Letters, Volume 42, Issue 28, 2001, Pages 4645-4648, ISSN 0040-4039, https://doi.org/10.1016/S0040-4039(01)00809-7.

46. Shohei Takata, Yuta Endo, Mohammad Shahid Ullah and Shinichi Itsuno Synthesis of cinchona alkaloid sulfonamide polymers as sustainable catalysts for the enantioselective desymmetrization of cyclic anhydrides. RSC Adv., 2016, 6, 72300-72305. https://doi.org/10.1039/C6RA14535C 47. Masud Parvez, Naoki Haraguchi, Shinichi Itsuno. Synthesis of Cinchona Alkaloid-Derived Chiral Polymers by Mizoroki-Heck Polymerization and Their Application to Asymmetric Catalysis. Macromolecules 2014, 47, 6, 1922-1928. Publication Date: Mar. 11, 2014. https://doi.org/10.1021/ma5001018

48. Marcelli, T. (2007). Cinchona-derived organocatalysts for asymmetric carbon-carbon bond formation. UvA-DARE (Digital Academic Repository). https://pure.uva.nl/ws/files/4416997/52576_marcelli_thesis.pdf

What is claimed is:

1. A compound having the structure of Formula I or II, or a pharmaceutically acceptable salt of Formula I or Formula II, the compound of Formula I comprising three alkaloid moieties substituted with R and R' and bound to pyrimidine as a linker, and the compound of Formula II comprising three alkaloid moieties substituted with R and R' and bound to L:

Formula I

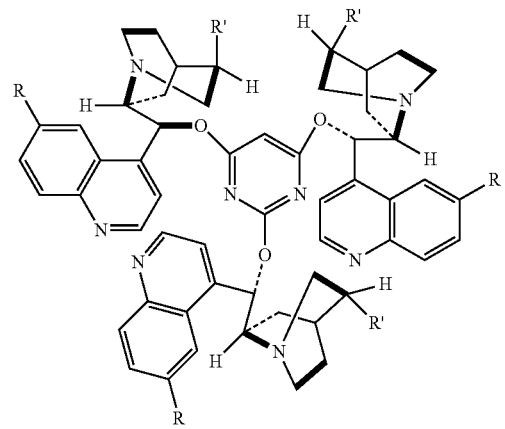

Formula II

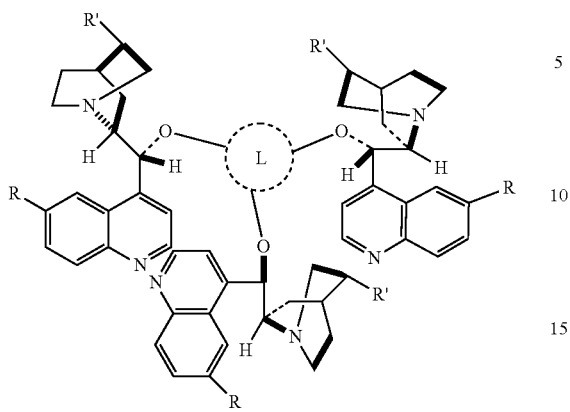

wherein each R is, independent of R', independently selected from the group consisting of H, Me, Et, Pr, Bu, tBu, Ph, PhCH$_2$, OH, OMe, OEt, OPr, OBu, OtBu, OPh, OCH$_2$Ph; each R' is, independent of R, independently selected from the group consisting of CH=CH$_2$, Me, Et, Pr, Bu, tBu, Ph, PhCH$_2$, OH, OMe, OEt, OPr, OBu, OtBu, OPh, or OCH$_2$Ph; and L represents a linker moiety selected from pyrazine, pyridazine, pyrimidine, and phthalazine.

2. A compound of claim 1, wherein R is H or OMe and R' is CH=CH$_2$.

3. The compound of claim 1 comprising the structure of Formula II having a tri-substituted cinchona alkaloid, wherein the linker moiety L is chosen independently from any one of the following:

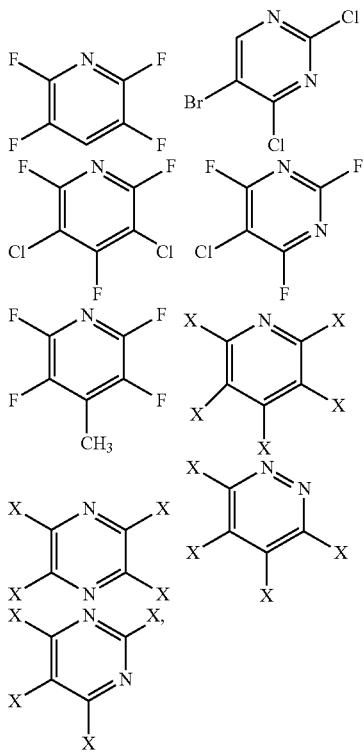

where X is chosen from F, Cl, Br, and I.

4. The compound of claim 1, wherein the compound is 2,4,6-Tri(9-O-cinchoninyl) pyrimidine (AP-1)

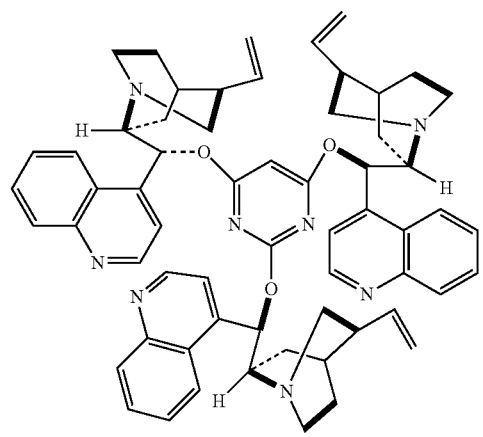

or a pharmaceutically acceptable salt thereof.

5. The compound of claim 1, wherein the compound is 2,4,6-Tri(9-O-cinchonidinyl)pyrimidine (AP-2)

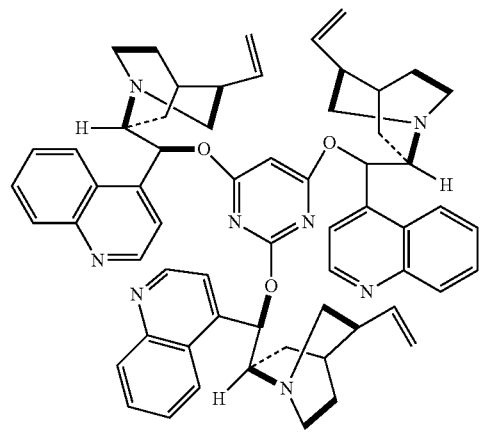

or a pharmaceutically acceptable salt thereof.

6. The compound of claim 1, wherein the compound is 2,4,6-Tri(9-O-quininyl)pyrimidine (AP-3)

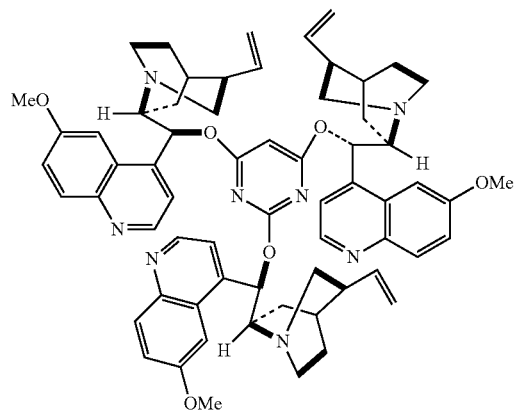

or a pharmaceutically acceptable salt thereof.

7. The compound of claim 1, wherein the compound is 2,4,6-Tri (9-O-quinidinyl)pyrimidine (AP-4)

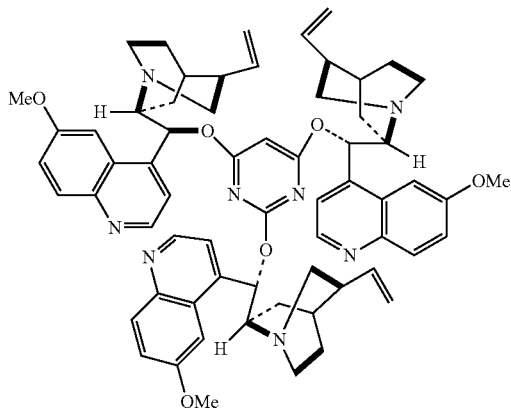

or a pharmaceutically acceptable salt thereof.

8. The compound of claim 1, wherein the compound is 2,4,6-Tri (9-O-dihydrocinchoninyl)pyrimidine (AP-5)

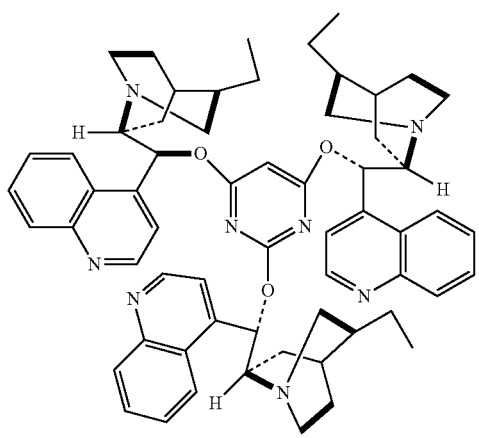

or a pharmaceutically acceptable salt thereof.

9. The compound of claim 1, wherein the compound is 2,4,6-Tri (9-O-dihydrocinchonidinyl)pyrimidine (AP-6)

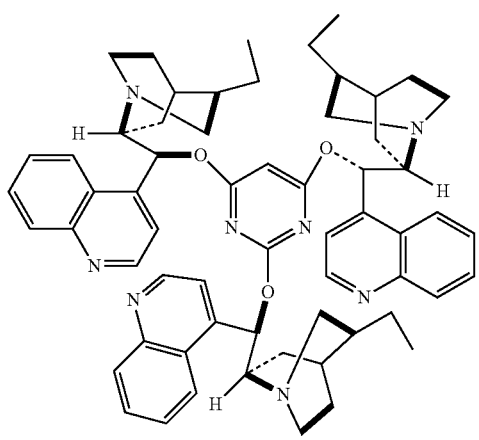

or a pharmaceutically acceptable salt thereof.

10. The compound of claim 1, wherein the compound is 2,4,6-Tri (9-O-dihydroquininyl)pyrimidine (AP-7)

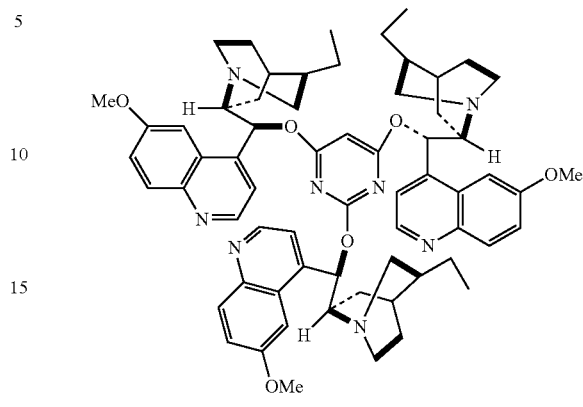

or a pharmaceutically acceptable salt thereof.

11. The compound of claim 1, wherein the compound is 2,4,6-Tri (9-O-dihydroquinidinyl)pyrimidine (AP-8)

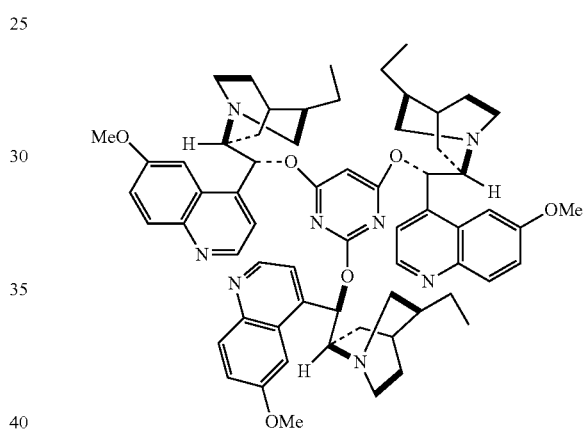

or a pharmaceutically acceptable salt thereof.

12. A pharmaceutical composition comprising effective therapeutic amount of a compound of claim 1 and a pharmaceutically acceptable carrier.

13. The pharmaceutical composition of claim 12, wherein the pharmaceutically acceptable carrier is selected from the group consisting of liposomes, fusion proteins, target-specific ligands or monoclonal antibodies.

14. A method for treating cancer in a mammal comprising administering to the mammal in need of such treatment an effective amount of a compound of claim 1 or a pharmaceutically acceptable salt thereof, or a pharmaceutical composition thereof, wherein the cancer is breast cancer, prostate cancer, glioblastoma multiforme, non-small cell lung cancer, leukemia, or lymphoma.

15. The method of claim 14, wherein the mammal is a human cancer patient.

16. A method for treating cells comprising contacting said cells with an effective amount of a compound of claim 1, a pharmaceutically acceptable salt thereof, or a pharmaceutical composition thereof, wherein the cells are leukemia cells, lymphoma cells, breast cancer cells, prostate cancer cells, or brain tumor cells.

17. The method of claim 16, wherein the method of is a method of inducing apoptosis or inhibition of growth of the cells, and said effective amount is an effective apoptosis-inducing or proliferation-inhibiting amount of the compound, the pharmaceutically acceptable salt thereof, or the pharmaceutical composition thereof.

18. The method of claim 16, wherein the method is for inhibiting the growth of the cells, and said effective amount is an effective inhibitory dose of the compound, the pharmaceutically acceptable salt thereof, or the pharmaceutical composition thereof.

* * * * *